United States Patent
Gemba

(10) Patent No.: US 9,617,547 B2
(45) Date of Patent: Apr. 11, 2017

(54) CHIRAL NUCLEIC ACID ADJUVANT

(71) Applicants: Shin Nippon Biomedical Laboratories, Ltd., Kagoshima-shi (JP); WaVe Life Sciences Japan, Kagoshima-shi (JP)

(72) Inventor: Takefumi Gemba, Kagoshima (JP)

(73) Assignees: Shin Nippon Biomedical Laboratories, Ltd., Kagoshima-shi (JP); WAVE LIFE SCIENCES JAPAN, Kagoshima-shi (JP)

( * ) Notice: Subject to any disclaimer, the term of this patent is extended or adjusted under 35 U.S.C. 154(b) by 0 days.

(21) Appl. No.: 14/414,551

(22) PCT Filed: Jul. 12, 2013

(86) PCT No.: PCT/JP2013/069107
§ 371 (c)(1),
(2) Date: Jan. 13, 2015

(87) PCT Pub. No.: WO2014/010718
PCT Pub. Date: Jan. 16, 2014

(65) Prior Publication Data
US 2015/0166999 A1    Jun. 18, 2015

Related U.S. Application Data

(60) Provisional application No. 61/671,654, filed on Jul. 13, 2012.

(51) Int. Cl.
*C12N 15/117* (2010.01)
*A61K 39/00* (2006.01)
*A61K 39/39* (2006.01)

(52) U.S. Cl.
CPC .......... *C12N 15/117* (2013.01); *A61K 39/39* (2013.01); *A61K 2039/55561* (2013.01); *C12N 2310/17* (2013.01); *C12N 2310/315* (2013.01)

(58) Field of Classification Search
None
See application file for complete search history.

(56) References Cited

U.S. PATENT DOCUMENTS

| | | |
|---|---|---|
| 2,878,264 A | 3/1959 | Lunsford |
| 3,135,766 A | 6/1964 | Gould |
| 3,484,473 A | 12/1969 | Buckman et al. |
| 3,687,808 A | 8/1972 | Merigan et al. |
| 3,745,162 A | 7/1973 | Helsley |
| 4,022,791 A | 5/1977 | Welch, Jr. |
| 4,113,869 A | 9/1978 | Gardner |
| 4,415,732 A | 11/1983 | Caruthers et al. |
| 4,458,066 A | 7/1984 | Caruthers et al. |
| 4,500,707 A | 2/1985 | Caruthers et al. |
| 4,542,142 A | 9/1985 | Martel et al. |
| 4,659,774 A | 4/1987 | Webb et al. |
| 4,663,328 A | 5/1987 | Lafon |
| 4,668,777 A | 5/1987 | Caruthers et al. |
| 4,725,677 A | 2/1988 | Koster et al. |
| 4,735,949 A | 4/1988 | Domagala et al. |
| 4,840,956 A | 6/1989 | Domagala et al. |
| 4,845,205 A | 7/1989 | Huynh Dinh et al. |
| 4,923,901 A | 5/1990 | Koester et al. |
| 4,973,679 A | 11/1990 | Caruthers et al. |
| 4,981,957 A | 1/1991 | Lebleu et al. |
| 5,047,524 A | 9/1991 | Andrus et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| 5,141,813 A | 8/1992 | Nelson |
| 5,151,510 A | 9/1992 | Stec et al. |
| 5,175,273 A | 12/1992 | Bischofberger et al. |
| 5,200,553 A | 4/1993 | Nudelman et al. |

(Continued)

FOREIGN PATENT DOCUMENTS

| DE | 1144279 B | 2/1963 |
|---|---|---|
| DE | 01934150 A1 | 1/1970 |

(Continued)

OTHER PUBLICATIONS

Tam, Journal of Hematotherapy & Stem Cell Research 12:467-471 (2003).*
International Search Report of PCT/JP2013/069107, 6 pages (Oct. 1, 2013).
Kim, D. et al., Immunostimulation and anti-DNA antibody production by backbone modified CpG-DNA, Biochemical and Biophysical Research Communicationes, 379: 362-367 (2009).
Krieg, A.M. et al., P-chirality-dependent immune activation by phosphorothioate CpG oligodeoxynucleotides, Oligonucleotides, 13(6): 491-499 (2003).
Molenkamp, B.G. et al., Local Administration of PF-3512676 CpG-B Instigates Tumor-Specific CD8+ T-Cell Reactivity in Melanoma Patients , Clin. Cancer Res., 14(14): 4532-4542 (2008).
Adams, S.P. et al., Hindered dialkylamino nucleoside phosphite reagents in the synthesis of two DNA 51-mers, Journal of the American Chemical Society, 105(3): 661-663 (1983).

(Continued)

*Primary Examiner* — Nita M Minnifield
(74) *Attorney, Agent, or Firm* — Choate, Hall & Stewart—LLP; Brenda Herschbach Jarrell

(57) ABSTRACT

Problem
The purpose of the present invention is to provide: a stereo isomer of a novel CpG oligonucleotide, which has excellent stability; and a CpG oligonucleotide which has a capability of producing interferon-α (IFNα).
Solution
The present invention relates to an oligonucleotide which contains two to four sequences each represented by the formula 5'-$X_1X_2$CpG$X_3X_4$-3' (formula (I)) and has a length of 14 to 32 nucleotides. In formula (I), CpG represents a non-methylated CpG residue having a phosphate skeleton modification, $X_1X_2$ represents any one of AA, AT, GA and GT, and $X_3X_4$ represents any one of TT, AT, AC and CG. The oligonucleotide has at least one phosphate skeleton modification at an S-form stereoisomer located at a site other than the CpG.

7 Claims, 2 Drawing Sheets

(56) References Cited

U.S. PATENT DOCUMENTS

| | | |
|---|---|---|
| 5,212,295 A | 5/1993 | Cook |
| 5,262,530 A | 11/1993 | Andrus et al. |
| 5,292,875 A | 3/1994 | Stec et al. |
| 5,319,080 A | 6/1994 | Leumann |
| 5,359,044 A | 10/1994 | Cook et al. |
| 5,367,066 A | 11/1994 | Urdea et al. |
| 5,432,272 A | 7/1995 | Benner |
| 5,457,187 A | 10/1995 | Gmeiner et al. |
| 5,457,191 A | 10/1995 | Cook et al. |
| 5,459,255 A | 10/1995 | Cook et al. |
| 5,484,908 A | 1/1996 | Froehler et al. |
| 5,502,177 A | 3/1996 | Matteucci et al. |
| 5,506,212 A | 4/1996 | Hoke et al. |
| 5,512,668 A | 4/1996 | Stec et al. |
| 5,521,302 A | 5/1996 | Cook |
| 5,525,711 A | 6/1996 | Hawkins et al. |
| 5,552,540 A | 9/1996 | Haralambidis |
| 5,576,302 A | 11/1996 | Cook et al. |
| 5,587,361 A | 12/1996 | Cook et al. |
| 5,587,469 A | 12/1996 | Cook et al. |
| 5,594,121 A | 1/1997 | Froehler et al. |
| 5,596,091 A | 1/1997 | Switzer |
| 5,599,797 A | 2/1997 | Cook et al. |
| 5,607,923 A | 3/1997 | Cook et al. |
| 5,614,617 A | 3/1997 | Cook et al. |
| 5,620,963 A | 4/1997 | Cook et al. |
| 5,635,488 A | 6/1997 | Cook et al. |
| 5,643,889 A | 7/1997 | Suhadolnik et al. |
| 5,643,989 A | 7/1997 | Van De Grampel et al. |
| 5,646,267 A | 7/1997 | Stec et al. |
| 5,654,284 A | 8/1997 | Cook et al. |
| 5,661,134 A | 8/1997 | Cook et al. |
| 5,681,940 A | 10/1997 | Wang et al. |
| 5,681,941 A | 10/1997 | Cook et al. |
| 5,708,161 A | 1/1998 | Reese |
| 5,712,378 A | 1/1998 | Wang |
| 5,734,041 A | 3/1998 | Just et al. |
| 5,750,692 A | 5/1998 | Cook et al. |
| 5,795,765 A | 8/1998 | Izu et al. |
| 5,824,503 A | 10/1998 | Kurome et al. |
| 5,851,840 A | 12/1998 | Sluka et al. |
| 5,852,188 A | 12/1998 | Cook |
| 5,856,465 A | 1/1999 | Stec et al. |
| 5,883,237 A | 3/1999 | Stec et al. |
| 5,898,031 A | 4/1999 | Crooke |
| 5,908,772 A | 6/1999 | Mitta et al. |
| 5,914,396 A | 6/1999 | Cook et al. |
| 5,932,450 A | 8/1999 | Dattagupta et al. |
| 5,936,080 A | 8/1999 | Stec et al. |
| 5,976,855 A | 11/1999 | Svendsen et al. |
| 5,998,602 A | 12/1999 | Torrence et al. |
| 6,004,813 A | 12/1999 | Serlupi-Crescenzi et al. |
| 6,015,886 A | 1/2000 | Dale et al. |
| 6,015,887 A | 1/2000 | Teng |
| 6,017,700 A | 1/2000 | Horn et al. |
| 6,031,092 A | 2/2000 | Just et al. |
| 6,056,973 A | 5/2000 | Allen et al. |
| 6,057,371 A | 5/2000 | Glennon |
| 6,066,500 A | 5/2000 | Bennett et al. |
| 6,080,543 A | 6/2000 | Engel et al. |
| 6,107,094 A | 8/2000 | Crooke |
| 6,124,445 A | 9/2000 | Imbach et al. |
| 6,140,096 A | 10/2000 | Kofod et al. |
| 6,146,829 A | 11/2000 | Cook et al. |
| 6,147,200 A | 11/2000 | Manoharan et al. |
| 6,159,728 A | 12/2000 | Stockley et al. |
| 6,160,109 A | 12/2000 | Just et al. |
| 6,166,197 A | 12/2000 | Cook et al. |
| 6,191,266 B1 | 2/2001 | Wang |
| 6,207,646 B1 | 3/2001 | Krieg et al. |
| 6,214,805 B1 | 4/2001 | Torrence et al. |
| 6,222,025 B1 | 4/2001 | Cook et al. |
| 6,235,887 B1 | 5/2001 | Froehler et al. |
| 6,239,116 B1 | 5/2001 | Krieg et al. |
| 6,239,265 B1 | 5/2001 | Cook |
| 6,242,589 B1 | 6/2001 | Cook et al. |
| 6,248,519 B1 | 6/2001 | Engel et al. |
| 6,265,172 B1 | 7/2001 | St. Clair et al. |
| 6,270,968 B1 | 8/2001 | Dalboge et al. |
| 6,271,004 B1 | 8/2001 | Warthoe |
| 6,300,069 B1 | 10/2001 | Missel et al. |
| 6,306,627 B1 | 10/2001 | Decker |
| 6,316,024 B1 | 11/2001 | Allen et al. |
| 6,316,626 B1 | 11/2001 | Swayze et al. |
| 6,322,985 B1 | 11/2001 | Kashi et al. |
| 6,326,199 B1 | 12/2001 | Cook et al. |
| 6,339,066 B1 | 1/2002 | Bennett et al. |
| 6,344,356 B1 | 2/2002 | Stemmer |
| 6,369,209 B1 | 4/2002 | Manoharan et al. |
| 6,369,237 B1 | 4/2002 | Verdine et al. |
| 6,380,368 B1 | 4/2002 | Froehler et al. |
| 6,383,808 B1 | 5/2002 | Monia et al. |
| 6,407,223 B1 | 6/2002 | Stec et al. |
| 6,440,943 B1 | 8/2002 | Cook et al. |
| 6,451,524 B1 | 9/2002 | Ecker |
| 6,455,308 B1 | 9/2002 | Freier |
| 6,468,983 B2 | 10/2002 | Silverman et al. |
| 6,500,945 B2 | 12/2002 | Cook |
| 6,506,594 B1 | 1/2003 | Barany et al. |
| 6,506,894 B1 | 1/2003 | Reese et al. |
| 6,528,262 B1 | 3/2003 | Gilad et al. |
| 6,528,640 B1 | 3/2003 | Beigelman et al. |
| 6,538,126 B1 | 3/2003 | Cho et al. |
| 6,559,279 B1 | 5/2003 | Manoharan et al. |
| 6,562,960 B1 | 5/2003 | Baxter et al. |
| 6,582,936 B1 | 6/2003 | Serafini et al. |
| 6,608,186 B1 | 8/2003 | Miculka et al. |
| 6,610,837 B1 | 8/2003 | Guzaev et al. |
| 6,613,873 B1 | 9/2003 | Buchardt et al. |
| 6,617,438 B1 | 9/2003 | Beigelman et al. |
| 6,632,600 B1 | 10/2003 | Short |
| 6,639,062 B2 | 10/2003 | Manoharan et al. |
| 6,649,750 B1 | 11/2003 | Capaldi et al. |
| 6,682,889 B1 | 1/2004 | Wang et al. |
| 6,699,979 B2 | 3/2004 | Cook |
| 6,737,520 B2 | 5/2004 | Manoharan et al. |
| 6,762,281 B2 | 7/2004 | Manoharan et al. |
| 6,767,739 B2 | 7/2004 | Crooke et al. |
| 6,809,195 B1 | 10/2004 | Sanghvi et al. |
| 6,811,975 B2 | 11/2004 | Cook et al. |
| 6,861,518 B2 | 3/2005 | Just et al. |
| 6,867,294 B1 | 3/2005 | Sanghvi et al. |
| 6,933,146 B2 | 8/2005 | Helliwell et al. |
| 6,933,288 B2 | 8/2005 | Migawa et al. |
| 6,936,432 B2 | 8/2005 | Gopalan et al. |
| 6,949,520 B1 * | 9/2005 | Hartmann ............ A61K 38/21 |
| | | 424/85.7 |
| 6,977,245 B2 * | 12/2005 | Klinman ............ A61K 31/7088 |
| | | 514/44 R |
| 6,995,259 B1 | 2/2006 | Vargeese et al. |
| 7,015,315 B1 | 3/2006 | Cook et al. |
| 7,018,793 B1 | 3/2006 | Short |
| 7,019,127 B2 | 3/2006 | Reese et al. |
| 7,022,833 B2 | 4/2006 | Reese |
| 7,045,610 B2 | 5/2006 | Dempcy et al. |
| 7,049,122 B2 | 5/2006 | Chang et al. |
| 7,067,497 B2 | 6/2006 | Hanecak et al. |
| 7,101,993 B1 | 9/2006 | Cook et al. |
| 7,119,184 B2 | 10/2006 | Manoharan et al. |
| RE39,464 E | 1/2007 | Cook et al. |
| 7,160,920 B2 | 1/2007 | Garvey et al. |
| 7,205,399 B2 | 4/2007 | Vargeese et al. |
| 7,214,491 B2 | 5/2007 | Yadav et al. |
| 7,227,014 B2 | 6/2007 | Crooke et al. |
| 7,259,150 B2 | 8/2007 | Crooke et al. |
| 7,264,932 B2 | 9/2007 | Latham et al. |
| 7,271,156 B2 * | 9/2007 | Krieg ................ A61K 31/7088 |
| | | 424/408 |
| 7,288,376 B2 | 10/2007 | Sarma et al. |
| 7,303,895 B1 | 12/2007 | O'Regan et al. |
| 7,304,081 B2 | 12/2007 | Yao et al. |
| 7,354,909 B2 * | 4/2008 | Klinman ............ A61K 39/39 |
| | | 514/44 R |
| 7,381,527 B2 | 6/2008 | Sarma et al. |

(56) References Cited

U.S. PATENT DOCUMENTS

| | | | |
|---|---|---|---|
| 7,399,845 B2 | 7/2008 | Seth et al. | |
| 7,407,943 B2 | 8/2008 | Crooke et al. | |
| 7,410,975 B2* | 8/2008 | Lipford | A61K 31/122 514/266.2 |
| 7,414,116 B2 | 8/2008 | Milton et al. | |
| 7,425,545 B2 | 9/2008 | Crooke et al. | |
| 7,427,672 B2 | 9/2008 | Imanishi et al. | |
| 7,432,249 B2 | 10/2008 | Crooke | |
| 7,432,250 B2 | 10/2008 | Crooke | |
| 7,495,088 B1 | 2/2009 | Brakel et al. | |
| 7,501,091 B2 | 3/2009 | Munoz et al. | |
| 7,507,808 B2 | 3/2009 | Dobie | |
| 7,511,131 B2 | 3/2009 | Crooke et al. | |
| 7,517,520 B2 | 4/2009 | Manolova et al. | |
| 7,534,879 B2 | 5/2009 | van Deutekom | |
| 7,537,767 B2 | 5/2009 | Bachmann et al. | |
| 7,547,684 B2 | 6/2009 | Seth et al. | |
| 7,585,847 B2* | 9/2009 | Bratzler | A61K 31/138 424/130.1 |
| 7,598,031 B2 | 10/2009 | Liew | |
| 7,598,227 B2 | 10/2009 | Crooke et al. | |
| 7,629,321 B2 | 12/2009 | Crooke | |
| 7,662,558 B2 | 2/2010 | Liew | |
| 7,666,854 B2 | 2/2010 | Seth et al. | |
| 7,666,888 B2 | 2/2010 | Bartberger et al. | |
| 7,683,036 B2 | 3/2010 | Esau et al. | |
| 7,695,902 B2 | 4/2010 | Crooke | |
| 7,696,345 B2 | 4/2010 | Allerson et al. | |
| 7,718,623 B2* | 5/2010 | Kitagawa | A61K 39/39 424/184.1 |
| 7,723,508 B2 | 5/2010 | Crooke et al. | |
| 7,732,590 B2 | 6/2010 | Bhanot et al. | |
| 7,732,660 B2 | 6/2010 | Helliwell et al. | |
| 7,741,305 B2 | 6/2010 | Crooke et al. | |
| 7,749,700 B2 | 7/2010 | Baird et al. | |
| 7,750,131 B2 | 7/2010 | Seth et al. | |
| 7,750,141 B2 | 7/2010 | Crooke et al. | |
| 7,750,731 B2 | 7/2010 | Poulsen et al. | |
| 7,759,318 B1 | 7/2010 | Perera et al. | |
| 7,776,344 B2* | 8/2010 | Hartmann | A61K 38/21 424/278.1 |
| 7,776,874 B2 | 8/2010 | Yao et al. | |
| 7,777,023 B2 | 8/2010 | Vargeese et al. | |
| 7,803,930 B2 | 9/2010 | Crooke et al. | |
| 7,812,003 B2 | 10/2010 | Safe et al. | |
| 7,838,287 B2 | 11/2010 | Goldsmith et al. | |
| 7,863,252 B2 | 1/2011 | Crooke et al. | |
| 7,884,086 B2 | 2/2011 | Bennett et al. | |
| 7,884,117 B2 | 2/2011 | Zhang et al. | |
| 7,888,324 B2 | 2/2011 | Crooke et al. | |
| 7,893,039 B2 | 2/2011 | Swayze et al. | |
| 7,919,472 B2 | 4/2011 | Monia et al. | |
| 7,947,658 B2 | 5/2011 | Aronin et al. | |
| 7,951,934 B2 | 5/2011 | Freier | |
| 7,973,015 B2 | 7/2011 | van Ommen et al. | |
| 8,003,619 B2* | 8/2011 | Hartmann | A61K 39/00 514/44 A |
| 8,008,011 B2 | 8/2011 | Schmutz et al. | |
| 8,008,459 B2 | 8/2011 | Goldsmith et al. | |
| 8,039,235 B2 | 10/2011 | Lin et al. | |
| 8,058,288 B2 | 11/2011 | Yao et al. | |
| 8,067,173 B2 | 11/2011 | Liew | |
| 8,076,303 B2 | 12/2011 | Iyer et al. | |
| 8,084,437 B2 | 12/2011 | Freier et al. | |
| 8,084,600 B2 | 12/2011 | Natt et al. | |
| 8,088,582 B2 | 1/2012 | Sampath et al. | |
| 8,093,222 B2 | 1/2012 | Freier et al. | |
| 8,093,225 B2 | 1/2012 | Mamet | |
| 8,101,348 B2 | 1/2012 | Tuschl et al. | |
| 8,101,358 B2 | 1/2012 | Liew | |
| 8,101,585 B2 | 1/2012 | Yu et al. | |
| 8,101,743 B2 | 1/2012 | Brown-Driver et al. | |
| 8,106,025 B2 | 1/2012 | Bennett et al. | |
| 8,110,358 B2 | 2/2012 | Liew | |
| 8,110,558 B2 | 2/2012 | Bennett et al. | |
| 8,114,597 B2 | 2/2012 | Liew | |
| 8,124,745 B2 | 2/2012 | Allerson et al. | |
| 8,133,674 B2 | 3/2012 | Liew | |
| 8,133,675 B2 | 3/2012 | Liew | |
| 8,133,876 B2 | 3/2012 | Bennett et al. | |
| 8,138,328 B2 | 3/2012 | Crooke et al. | |
| 8,143,230 B2 | 3/2012 | Bhanot et al. | |
| 8,148,072 B2 | 4/2012 | Liew | |
| 8,158,598 B2 | 4/2012 | Bhanot et al. | |
| 8,178,506 B2 | 5/2012 | Lollo et al. | |
| 8,188,059 B2 | 5/2012 | Bhanot et al. | |
| 8,206,923 B2 | 6/2012 | Garza Gonzalez et al. | |
| 8,207,263 B2 | 6/2012 | Popot et al. | |
| 8,257,922 B2 | 9/2012 | Liew | |
| 8,258,289 B2 | 9/2012 | Bhanot et al. | |
| 8,383,660 B2 | 2/2013 | Chang et al. | |
| 8,415,465 B2 | 4/2013 | Freier | |
| 8,470,987 B2 | 6/2013 | Wada et al. | |
| 8,481,710 B2 | 7/2013 | Davidson et al. | |
| 8,501,414 B2 | 8/2013 | Danzer et al. | |
| 8,557,549 B2 | 10/2013 | Chang et al. | |
| 8,592,566 B2* | 11/2013 | Iwamura | A61K 31/711 424/189.1 |
| 8,632,963 B2 | 1/2014 | Shah et al. | |
| 8,633,206 B2 | 1/2014 | Promo et al. | |
| 8,647,742 B2 | 2/2014 | Dendukuri et al. | |
| 8,648,186 B2 | 2/2014 | Monteleone | |
| 8,669,058 B2 | 3/2014 | Liew | |
| 8,674,044 B2 | 3/2014 | Popot et al. | |
| 8,679,750 B2 | 3/2014 | Hayden et al. | |
| 8,680,063 B2 | 3/2014 | Aronin et al. | |
| 8,729,036 B2 | 5/2014 | Zamore et al. | |
| 8,735,417 B2 | 5/2014 | Altman et al. | |
| 8,750,507 B2 | 6/2014 | Roosta et al. | |
| 8,754,107 B2 | 6/2014 | George et al. | |
| 8,759,507 B2 | 6/2014 | Van Deutekom | |
| 8,809,516 B2 | 8/2014 | Manoharan et al. | |
| 8,822,671 B2 | 9/2014 | Shimizu et al. | |
| 8,859,755 B2 | 10/2014 | Wada et al. | |
| 8,877,435 B2 | 11/2014 | Helliwell et al. | |
| 8,883,969 B2 | 11/2014 | Ide et al. | |
| 8,952,145 B2 | 2/2015 | Freier | |
| 8,957,040 B2 | 2/2015 | Bennett et al. | |
| 8,957,042 B2 | 2/2015 | Safe et al. | |
| 8,975,389 B2 | 3/2015 | Manoharan et al. | |
| 8,987,222 B2 | 3/2015 | Aronin et al. | |
| 8,993,738 B2 | 3/2015 | Prakash et al. | |
| 9,006,198 B2 | 4/2015 | Bennett et al. | |
| 9,040,674 B2 | 5/2015 | Benson et al. | |
| 9,121,020 B2 | 9/2015 | Feinstein et al. | |
| 9,126,927 B2 | 9/2015 | Yao et al. | |
| 9,127,123 B2 | 9/2015 | Livingston et al. | |
| 9,260,716 B2 | 2/2016 | Davidson et al. | |
| 9,273,315 B2 | 3/2016 | Hung et al. | |
| 9,284,344 B2 | 3/2016 | Kim et al. | |
| 9,308,252 B2* | 4/2016 | Suckow | A61K 39/08 |
| 9,394,333 B2 | 7/2016 | Wada et al. | |
| 9,453,228 B2* | 9/2016 | Kandimalla | A61K 48/00 |
| 9,480,740 B2* | 11/2016 | Reed | A61K 39/00 |
| 2001/0055761 A1 | 12/2001 | Kanemoto et al. | |
| 2002/0013792 A1 | 1/2002 | Imielinski et al. | |
| 2002/0082227 A1 | 6/2002 | Henry | |
| 2002/0137921 A1 | 9/2002 | Cook | |
| 2003/0045705 A1 | 3/2003 | Cook et al. | |
| 2003/0049662 A1 | 3/2003 | Monia et al. | |
| 2003/0050261 A1 | 3/2003 | Krieg et al. | |
| 2003/0235845 A1 | 12/2003 | van Ommen et al. | |
| 2004/0063647 A1* | 4/2004 | Johnson | C07C 69/76 514/23 |
| 2004/0213780 A1 | 10/2004 | Krainc | |
| 2005/0042646 A1 | 2/2005 | Davidson et al. | |
| 2005/0059619 A1 | 3/2005 | Krieg et al. | |
| 2005/0096284 A1 | 5/2005 | McSwiggen | |
| 2005/0159375 A1 | 7/2005 | Srivastava et al. | |
| 2005/0169888 A1 | 8/2005 | Hartmann et al. | |
| 2005/0239102 A1 | 10/2005 | Verdine et al. | |
| 2005/0277133 A1 | 12/2005 | McSwiggen | |

(56) References Cited

U.S. PATENT DOCUMENTS

| | | | |
|---|---|---|---|
| 2005/0277609 A1* | 12/2005 | Krieg | A61K 31/00 514/44 A |
| 2006/0003962 A1 | 1/2006 | Ahluwalia et al. | |
| 2006/0035858 A1 | 2/2006 | Geary et al. | |
| 2006/0063730 A1 | 3/2006 | Monia et al. | |
| 2006/0099616 A1 | 5/2006 | van Ommen et al. | |
| 2006/0147952 A1 | 7/2006 | van Ommen et al. | |
| 2006/0211644 A1 | 9/2006 | Krieg et al. | |
| 2006/0257912 A1 | 11/2006 | Kaemmerer et al. | |
| 2007/0099860 A1 | 5/2007 | Sah et al. | |
| 2007/0149462 A1 | 6/2007 | Iyer et al. | |
| 2007/0161547 A1 | 7/2007 | Bhat et al. | |
| 2007/0161590 A1 | 7/2007 | Van Bilsen et al. | |
| 2007/0249589 A1 | 10/2007 | Aebi et al. | |
| 2007/0282097 A1 | 12/2007 | Ohgi et al. | |
| 2007/0287831 A1 | 12/2007 | Seth et al. | |
| 2007/0299027 A1 | 12/2007 | Hung et al. | |
| 2008/0015158 A1 | 1/2008 | Ichiro et al. | |
| 2008/0039418 A1 | 2/2008 | Freier | |
| 2008/0045473 A1 | 2/2008 | Uhlmann et al. | |
| 2008/0064867 A1 | 3/2008 | Leuck et al. | |
| 2008/0209581 A1 | 8/2008 | van Ommen et al. | |
| 2008/0221055 A1 | 9/2008 | Sah et al. | |
| 2008/0221303 A1 | 9/2008 | Katzhendler et al. | |
| 2008/0249291 A1 | 10/2008 | Kwon et al. | |
| 2008/0274989 A1 | 11/2008 | Davidson et al. | |
| 2009/0012120 A1 | 1/2009 | Borhan et al. | |
| 2009/0023675 A1 | 1/2009 | McSwiggen et al. | |
| 2009/0053148 A1* | 2/2009 | Kandimalla | A61K 31/711 424/45 |
| 2009/0053205 A1* | 2/2009 | Kandimalla | A61K 31/7105 424/130.1 |
| 2009/0060898 A1* | 3/2009 | Kandimalla | A61K 48/00 424/130.1 |
| 2009/0062224 A1 | 3/2009 | Kim et al. | |
| 2009/0093425 A1 | 4/2009 | Dowdy et al. | |
| 2009/0162316 A1 | 6/2009 | Verdine et al. | |
| 2009/0186410 A1 | 7/2009 | Aronin et al. | |
| 2009/0228998 A1 | 9/2009 | van Ommen et al. | |
| 2009/0263413 A1 | 10/2009 | Iwamura et al. | |
| 2009/0306176 A1 | 12/2009 | Schlingensiepen et al. | |
| 2010/0008981 A1 | 1/2010 | Kaemmerer et al. | |
| 2010/0038543 A1 | 2/2010 | Toda et al. | |
| 2010/0069472 A1 | 3/2010 | Hung et al. | |
| 2010/0120900 A1 | 5/2010 | van Bilsen et al. | |
| 2010/0215642 A1* | 8/2010 | Lan | C12N 15/117 424/130.1 |
| 2010/0273999 A1 | 10/2010 | Jung et al. | |
| 2010/0299768 A1 | 11/2010 | Perrin et al. | |
| 2010/0325746 A9 | 12/2010 | Kaemmerer et al. | |
| 2011/0009477 A1* | 1/2011 | Yu | A61K 31/711 514/44 R |
| 2011/0039334 A1 | 2/2011 | Bennett et al. | |
| 2011/0105587 A1 | 5/2011 | Fishcher et al. | |
| 2011/0111491 A1 | 5/2011 | Davidson et al. | |
| 2011/0136765 A1 | 6/2011 | Promo et al. | |
| 2011/0178284 A1 | 7/2011 | Wada et al. | |
| 2011/0201599 A1 | 8/2011 | Bahceci et al. | |
| 2011/0212520 A1 | 9/2011 | Davidson et al. | |
| 2011/0213010 A1 | 9/2011 | Hayden et al. | |
| 2011/0257251 A1 | 10/2011 | Gude-Rodriguez et al. | |
| 2011/0294124 A1 | 12/2011 | Wada et al. | |
| 2011/0294869 A1 | 12/2011 | Petersen | |
| 2012/0095076 A1 | 4/2012 | Sah et al. | |
| 2012/0136039 A1 | 5/2012 | Aronin et al. | |
| 2012/0208864 A1 | 8/2012 | Bhanot et al. | |
| 2012/0246747 A1 | 9/2012 | Tuschl et al. | |
| 2012/0252879 A1 | 10/2012 | Hung et al. | |
| 2012/0308609 A1* | 12/2012 | Gibbon | C07D 473/18 424/278.1 |
| 2012/0316224 A1 | 12/2012 | Verdine et al. | |
| 2013/0005794 A1 | 1/2013 | Kaemmerer et al. | |
| 2013/0046008 A1 | 2/2013 | Bennett et al. | |
| 2013/0072671 A1 | 3/2013 | Van Deutekom | |
| 2013/0178612 A1 | 7/2013 | Wada et al. | |
| 2013/0184450 A1 | 7/2013 | Wada et al. | |
| 2013/0189782 A1 | 7/2013 | Hung et al. | |
| 2013/0197061 A1 | 8/2013 | Hohjoh et al. | |
| 2013/0281684 A1 | 10/2013 | Freier | |
| 2013/0302806 A1 | 11/2013 | Van Deutekom | |
| 2014/0142160 A1 | 5/2014 | Lee et al. | |
| 2014/0163213 A1 | 6/2014 | Debelak et al. | |
| 2014/0194610 A1 | 7/2014 | Verdine et al. | |
| 2014/0213635 A1 | 7/2014 | Van Deutekom | |
| 2014/0275212 A1 | 9/2014 | van Deutekom | |
| 2014/0323707 A1 | 10/2014 | Seth et al. | |
| 2014/0350076 A1 | 11/2014 | van Deutekom | |
| 2014/0357698 A1 | 12/2014 | Van Deutekom et al. | |
| 2014/0357855 A1 | 12/2014 | Van Deutekom et al. | |
| 2014/0373188 A1 | 12/2014 | Zamore et al. | |
| 2014/0378527 A1 | 12/2014 | van Deutekom | |
| 2015/0051389 A1 | 2/2015 | Seth et al. | |
| 2015/0096064 A1 | 4/2015 | Tuschl et al. | |
| 2015/0166999 A1* | 6/2015 | Gemba | A61K 39/39 536/23.1 |
| 2015/0197540 A1 | 7/2015 | Shimizu et al. | |
| 2015/0211006 A1 | 7/2015 | Butler et al. | |
| 2015/0218559 A1 | 8/2015 | Van Deutekom et al. | |
| 2015/0275208 A1 | 10/2015 | Oestergaard et al. | |
| 2015/0307877 A1 | 10/2015 | Freier | |
| 2015/0322434 A1 | 11/2015 | van Deutekom | |
| 2015/0329859 A1 | 11/2015 | Bennett et al. | |
| 2015/0335708 A1 | 11/2015 | Froelich et al. | |
| 2015/0361424 A1 | 12/2015 | van Deutekom | |
| 2016/0017327 A1 | 1/2016 | Rudnicki et al. | |
| 2016/0138022 A1* | 5/2016 | Kandimalla | A61K 48/00 424/130.1 |
| 2016/0186178 A1* | 6/2016 | Radovic-Moreno | C12N 15/117 424/184.1 |
| 2016/0251653 A1 | 9/2016 | Davidson et al. | |
| 2016/0312217 A1 | 10/2016 | Hung et al. | |
| 2016/0331835 A1* | 11/2016 | Gemba | C12N 15/117 |
| 2016/0331836 A1* | 11/2016 | Gemba | A61K 31/7088 |
| 2016/0333349 A1* | 11/2016 | Gemba | A61K 48/00 |
| 2016/0347780 A1 | 12/2016 | Wada et al. | |
| 2016/0347784 A1 | 12/2016 | Verdine et al. | |

FOREIGN PATENT DOCUMENTS

| | | |
|---|---|---|
| DE | 133885 A1 | 1/1979 |
| EA | 008940 B1 | 10/2007 |
| EP | 0 002 322 A2 | 6/1979 |
| EP | 192521 A1 | 8/1986 |
| EP | 269258 A2 | 6/1988 |
| EP | 0506242 A1 | 9/1992 |
| EP | 0531447 A1 | 3/1993 |
| EP | 0604409 A1 | 7/1994 |
| EP | 0655088 A1 | 5/1995 |
| EP | 0779893 A2 | 6/1997 |
| EP | 0831854 A1 | 4/1998 |
| EP | 0973945 A1 | 1/2000 |
| EP | 1097162 A2 | 5/2001 |
| EP | 1100807 A1 | 5/2001 |
| EP | 1185305 | 3/2002 |
| EP | 1244682 A1 | 10/2002 |
| EP | 1311526 A1 | 5/2003 |
| EP | 1418179 A2 | 5/2004 |
| EP | 1499627 A2 | 1/2005 |
| EP | 1539188 A2 | 6/2005 |
| EP | 1556077 A2 | 7/2005 |
| EP | 1560840 A2 | 8/2005 |
| EP | 1562971 A2 | 8/2005 |
| EP | 1670810 A2 | 6/2006 |
| EP | 1670896 A2 | 6/2006 |
| EP | 1795536 A1 | 6/2007 |
| EP | 1957507 A2 | 8/2008 |
| EP | 1984381 A2 | 10/2008 |
| EP | 2021472 A2 | 2/2009 |
| EP | 2062980 A2 | 5/2009 |
| EP | 2066684 A2 | 6/2009 |
| EP | 2149571 A1 | 2/2010 |
| EP | 2161038 A1 | 3/2010 |
| EP | 2170917 A2 | 4/2010 |

(56) References Cited

FOREIGN PATENT DOCUMENTS

| | | |
|---|---|---|
| EP | 2173760 A2 | 4/2010 |
| EP | 2176280 A2 | 4/2010 |
| EP | 2282744 A1 | 2/2011 |
| EP | 2285819 A1 | 2/2011 |
| EP | 2316967 A1 | 5/2011 |
| EP | 2360166 A1 | 8/2011 |
| EP | 2399588 A1 | 12/2011 |
| EP | 2422819 A2 | 2/2012 |
| EP | 2428227 A1 | 3/2012 |
| EP | 2462153 A2 | 6/2012 |
| EP | 2479182 A1 | 7/2012 |
| EP | 14193887.8 | 11/2014 |
| EP | 14198167.0 | 12/2014 |
| EP | 15182401.8 | 8/2015 |
| EP | 15191074.2 | 10/2015 |
| EP | 15191075.9 | 10/2015 |
| EP | 15191076.7 | 10/2015 |
| EP | 2982758 A1 | 2/2016 |
| GB | 1448437 A | 9/1976 |
| GB | 2016273 A | 9/1979 |
| JP | 2001-503267 A | 3/2001 |
| JP | 2002-513763 A | 5/2002 |
| JP | 2002-514397 A | 5/2002 |
| JP | 2002-521489 A | 7/2002 |
| JP | 2003-510290 A | 3/2003 |
| JP | 2003/238586 A | 8/2003 |
| JP | 2006-508693 A | 3/2006 |
| JP | 2006-515277 A | 5/2006 |
| JP | 2008-531018 A | 8/2008 |
| JP | 2009-190983 A | 8/2009 |
| JP | 4348044 B2 | 10/2009 |
| JP | 04348077 B2 | 10/2009 |
| JP | 2010-504750 A | 2/2010 |
| JP | 2010/241836 A | 10/2010 |
| JP | 2010/265304 A | 11/2010 |
| JP | A03-074398 | 3/2011 |
| JP | 2011/088935 A | 5/2011 |
| JP | 2011/225598 A | 11/2011 |
| WO | WO-91/10671 A1 | 7/1991 |
| WO | WO-91/16331 A1 | 10/1991 |
| WO | WO-91/17755 A1 | 11/1991 |
| WO | WO-93/08296 A1 | 4/1993 |
| WO | WO-94/17093 A1 | 8/1994 |
| WO | WO-96/02555 A1 | 2/1996 |
| WO | WO-96/07392 A2 | 3/1996 |
| WO | WO-96/14329 A1 | 5/1996 |
| WO | WO-96/19572 A1 | 6/1996 |
| WO | WO-96/37504 A1 | 11/1996 |
| WO | WO-96/39413 A1 | 12/1996 |
| WO | WO-97/06183 A1 | 2/1997 |
| WO | WO-97/14710 A1 | 4/1997 |
| WO | WO-97/47637 A1 | 12/1997 |
| WO | WO-98/02582 A2 | 1/1998 |
| WO | WO-98/03542 A1 | 1/1998 |
| WO | WO-98/07734 A1 | 2/1998 |
| WO | WO-98/18810 A1 | 5/1998 |
| WO | WO-98/39334 A1 | 9/1998 |
| WO | WO-98/46794 A1 | 10/1998 |
| WO | WO-98/53801 A1 | 12/1998 |
| WO | WO-99/05160 A2 | 2/1999 |
| WO | WO-99/12034 A1 | 3/1999 |
| WO | WO-99/56755 A1 | 11/1999 |
| WO | WO-99/58118 A2 | 11/1999 |
| WO | WO-00/00499 A1 | 1/2000 |
| WO | WO-00/04034 A2 | 1/2000 |
| WO | WO-00/06588 A1 | 2/2000 |
| WO | WO-00/23444 A1 | 4/2000 |
| WO | WO-00/31110 A1 | 6/2000 |
| WO | WO-00/37658 A2 | 6/2000 |
| WO | WO-00/55179 A1 | 9/2000 |
| WO | WO-00/58329 A1 | 10/2000 |
| WO | WO-00/76554 A1 | 12/2000 |
| WO | WO-01/02415 A1 | 1/2001 |
| WO | WO-01/22990 A2 | 4/2001 |
| WO | WO-01/27126 A1 | 4/2001 |
| WO | WO-01/40515 A1 | 6/2001 |
| WO | WO-01/49701 A1 | 7/2001 |
| WO | WO-01/64702 A1 | 9/2001 |
| WO | WO-01/81303 A1 | 11/2001 |
| WO | WO-01/85751 A1 | 11/2001 |
| WO | WO-01/88198 A1 | 11/2001 |
| WO | WO-02/14340 A1 | 2/2002 |
| WO | WO-02/20544 A1 | 3/2002 |
| WO | WO-02/22635 A1 | 3/2002 |
| WO | WO-02/24906 A1 | 3/2002 |
| WO | WO 02/32450 * | 4/2002 |
| WO | WO-02/057425 A2 | 7/2002 |
| WO | WO-02/097134 A2 | 12/2002 |
| WO | WO-02/099317 A1 | 12/2002 |
| WO | WO-03/002065 A2 | 1/2003 |
| WO | WO-03/004602 A1 | 1/2003 |
| WO | WO-03/011887 A2 | 2/2003 |
| WO | WO-03/012057 A2 | 2/2003 |
| WO | WO-03/014306 A2 | 2/2003 |
| WO | WO-03/014307 A2 | 2/2003 |
| WO | WO-03/018600 A2 | 3/2003 |
| WO | WO-03/066633 A1 | 8/2003 |
| WO | WO-03/097662 A1 | 11/2003 |
| WO | WO-03/099840 A1 | 12/2003 |
| WO | WO-03/100017 A2 | 12/2003 |
| WO | WO-03/106477 A1 | 12/2003 |
| WO | WO-04/000351 A1 | 12/2003 |
| WO | WO-2004/007718 A2 | 1/2004 |
| WO | WO-2004/016805 A2 | 2/2004 |
| WO | WO-2004010956 A2 | 2/2004 |
| WO | WO-2004/024919 A1 | 3/2004 |
| WO | WO-2004/039829 A2 | 5/2004 |
| WO | WO-2004041889 A2 | 5/2004 |
| WO | WO-2004044134 A2 | 5/2004 |
| WO | WO-2004044136 A2 | 5/2004 |
| WO | WO-2004044141 A2 | 5/2004 |
| WO | WO-2004044181 A2 | 5/2004 |
| WO | WO-2004/048522 A2 | 6/2004 |
| WO | WO-2004055162 A2 | 7/2004 |
| WO | WO-2004/083432 A1 | 9/2004 |
| WO | WO-2004/083446 A2 | 9/2004 |
| WO | WO-2004/085454 A1 | 10/2004 |
| WO | WO-2004093783 A2 | 11/2004 |
| WO | WO-2005000201 A2 | 1/2005 |
| WO | WO-2005005599 A2 | 1/2005 |
| WO | WO-2005/014609 A2 | 2/2005 |
| WO | WO-2005013901 A2 | 2/2005 |
| WO | WO-2005/023828 A1 | 3/2005 |
| WO | WO-2005/028494 A1 | 3/2005 |
| WO | WO-2005019418 A2 | 3/2005 |
| WO | WO-2005023825 A2 | 3/2005 |
| WO | WO-2005023995 A2 | 3/2005 |
| WO | WO 2005/039630 * | 5/2005 |
| WO | WO-2005/042018 A2 | 5/2005 |
| WO | WO-2005/042716 A2 | 5/2005 |
| WO | WO-2005/070859 A1 | 8/2005 |
| WO | WO-2005/085272 A1 | 9/2005 |
| WO | WO-2005/092909 A1 | 10/2005 |
| WO | WO-2006020676 A2 | 2/2006 |
| WO | WO-2006/022323 A1 | 3/2006 |
| WO | WO-2006/029258 A2 | 3/2006 |
| WO | WO-2006/031267 A2 | 3/2006 |
| WO | WO-2006031461 A2 | 3/2006 |
| WO | WO-2006044531 A2 | 4/2006 |
| WO | WO-2006/049454 A1 | 5/2006 |
| WO | WO-2006/065751 A2 | 6/2006 |
| WO | WO-2006/066260 A2 | 6/2006 |
| WO | WO-2006/070284 A1 | 7/2006 |
| WO | WO-2006/080596 A1 | 8/2006 |
| WO | WO-2006/091915 A2 | 8/2006 |
| WO | WO-2006/117400 A2 | 11/2006 |
| WO | WO-2006/121960 A2 | 11/2006 |
| WO | WO-2007/002904 A2 | 1/2007 |
| WO | WO-2007/005941 A2 | 1/2007 |
| WO | WO-2007027775 A2 | 3/2007 |
| WO | WO-2007/041045 A2 | 4/2007 |
| WO | WO-2007/051045 A2 | 5/2007 |
| WO | WO-2007/059041 A2 | 5/2007 |
| WO | WO-2007/064291 A1 | 6/2007 |

(56) References Cited

FOREIGN PATENT DOCUMENTS

| | | |
|---|---|---|
| WO | WO-2007/070598 A2 | 6/2007 |
| WO | WO-2007064954 A2 | 6/2007 |
| WO | WO-2007/089584 A2 | 8/2007 |
| WO | WO-2007/089611 A2 | 8/2007 |
| WO | WO-2007/095316 A2 | 8/2007 |
| WO | WO-2007131232 A2 | 11/2007 |
| WO | WO-2007131237 A2 | 11/2007 |
| WO | WO-2007131238 A2 | 11/2007 |
| WO | WO-2007134014 A2 | 11/2007 |
| WO | WO-2007136988 A2 | 11/2007 |
| WO | WO-2007/139190 A1 | 12/2007 |
| WO | WO-2007143315 A2 | 12/2007 |
| WO | WO-2007143316 A2 | 12/2007 |
| WO | WO-2007143317 A2 | 12/2007 |
| WO | WO-2007146511 A2 | 12/2007 |
| WO | WO-2008/005562 A2 | 1/2008 |
| WO | WO-2008/008476 A2 | 1/2008 |
| WO | WO-2008/021136 A2 | 2/2008 |
| WO | WO-2008017081 A1 | 2/2008 |
| WO | WO-2008/049085 A1 | 4/2008 |
| WO | WO-2008/068638 A2 | 6/2008 |
| WO | WO-2008066776 A2 | 6/2008 |
| WO | WO-2008/098104 A1 | 8/2008 |
| WO | WO-2008118883 A1 | 10/2008 |
| WO | WO-2008139262 A2 | 11/2008 |
| WO | WO-2008/148801 A2 | 12/2008 |
| WO | WO-2008/151833 A2 | 12/2008 |
| WO | WO-2009/007855 A2 | 1/2009 |
| WO | WO-2009046141 A2 | 4/2009 |
| WO | WO-2009/086264 A1 | 7/2009 |
| WO | WO-2009/089689 A1 | 7/2009 |
| WO | WO-2009/098197 A1 | 8/2009 |
| WO | WO-2009117589 A1 | 9/2009 |
| WO | WO-2009/124238 A1 | 10/2009 |
| WO | WO-2009/135322 A1 | 11/2009 |
| WO | WO-2009143387 A2 | 11/2009 |
| WO | WO-2009143390 A2 | 11/2009 |
| WO | WO-2009143391 A2 | 11/2009 |
| WO | WO-2009143463 A2 | 11/2009 |
| WO | WO-2009/146123 A2 | 12/2009 |
| WO | WO-2009148605 A2 | 12/2009 |
| WO | WO-2010/003133 A2 | 1/2010 |
| WO | WO-2010/039543 A2 | 4/2010 |
| WO | WO-2010/042636 A2 | 4/2010 |
| WO | WO-2010036696 A1 | 4/2010 |
| WO | WO-2010036698 A1 | 4/2010 |
| WO | WO-2010048552 A2 | 4/2010 |
| WO | WO-2010/064146 A2 | 6/2010 |
| WO | WO-2010/072831 A1 | 7/2010 |
| WO | WO-2010/080953 A1 | 7/2010 |
| WO | WO-2010/091301 A1 | 8/2010 |
| WO | WO-2010/107838 A1 | 9/2010 |
| WO | WO-2010/118263 A1 | 10/2010 |
| WO | WO-2010/129853 A2 | 11/2010 |
| WO | WO-2010/141471 A2 | 12/2010 |
| WO | WO-2011/005761 A1 | 1/2011 |
| WO | WO-2011/015572 A1 | 2/2011 |
| WO | WO-2011/015573 A1 | 2/2011 |
| WO | WO-2011/017521 A2 | 2/2011 |
| WO | WO-2011/034072 A1 | 3/2011 |
| WO | WO-2011038288 A1 | 3/2011 |
| WO | WO-2011/045702 A1 | 4/2011 |
| WO | WO-2011085271 A2 | 7/2011 |
| WO | WO-2011/097643 A1 | 8/2011 |
| WO | WO-2011/097644 A2 | 8/2011 |
| WO | WO-2011/108682 A1 | 9/2011 |
| WO | WO-2011127175 A1 | 10/2011 |
| WO | WO-2011127307 A1 | 10/2011 |
| WO | WO-2011/139911 A2 | 11/2011 |
| WO | WO-2012/030683 A2 | 3/2012 |
| WO | WO-2012/039448 A1 | 3/2012 |
| WO | WO-2012/073857 A1 | 6/2012 |
| WO | WO-2012/151324 A1 | 11/2012 |
| WO | WO-2013/012758 A1 | 1/2013 |
| WO | WO-2014/010250 A1 | 1/2014 |
| WO | WO 2014/010718 A1 * | 1/2014 |
| WO | WO-2014/012081 A2 | 1/2014 |
| WO | WO-2014/025805 A1 | 2/2014 |
| WO | WO-2014/059356 A2 | 4/2014 |
| WO | WO-2014/179626 A2 | 11/2014 |
| WO | WO-2015/010135 A2 | 1/2015 |
| WO | WO-2015/051214 A1 | 4/2015 |
| WO | WO-2015/051366 A2 | 4/2015 |
| WO | WO-2015/070212 A1 | 5/2015 |
| WO | WO-2015/089511 A2 | 6/2015 |
| WO | WO-2015/107425 A2 | 7/2015 |
| WO | WO 2015/108046 A1 * | 7/2015 |
| WO | WO 2015/108047 A1 * | 7/2015 |
| WO | WO 2015/108047 A1 * | 7/2015 |
| WO | WO 2015/108048 A1 * | 7/2015 |
| WO | WO 2015/108048 A1 * | 7/2015 |
| WO | WO-2015/171932 A1 | 11/2015 |
| WO | WO-2015/179525 A1 | 11/2015 |
| WO | WO-2016/011226 A1 | 1/2016 |
| WO | WO-2016/020399 A1 | 2/2016 |
| WO | WO-2016/027168 A2 | 2/2016 |
| WO | WO-2016/037191 A1 | 3/2016 |
| WO | WO-2016/079181 A1 | 5/2016 |
| WO | WO-2016/079183 A1 | 5/2016 |
| WO | WO-2016/102664 A1 | 6/2016 |
| WO | WO-2016/130589 A2 | 8/2016 |
| WO | WO-2016/161374 A1 | 10/2016 |

OTHER PUBLICATIONS

Adarsh, et al., Organelle Specific Targeted Drug Delivery—A Review, International Journal of Research in Pharmaceutical and Biomedical Sciences, 2(3): 895-912 (2011).

Ager, D.J. The Peterson olefination reaction, Organic Reactions, 38: 1-223 (2004).

Agrawal, S. and Kandimalla, E.R., Antisense and/or Immunostimulatory Oligonucleotide THerapeutics, Current Cancer Drug Targets, Bentham Science, 1(3): 1 page. URL: <http:www.eurekaselect.com/65087/article> [Retrieved Apr. 3, 2016].

Agrawal, S. and Tang, J.Y., GEM 91—an antisense oligonucleotide phosphorothioate as a therapeutic agent for AIDS, Antisense Research and Development, 2(4):261-266 (1992).

Agrawal, S. et al., Mixed-backbone oligonucleotides as second generation antisense oligonucleotides: In vitro and in vivo studies, Proc. Natl. Acad. Sci. USA, 94: 2620-2625 (1997).

Aldaye, F.A. et al., Assembling materials with DNA as the guide, Science, 321(5897): 1795-1799 (2008).

Aldrich Chemical Co. Catalog, 2007-2008 Issue, only p. 1719 supplied: see first full entry at col. 1 (S-methyl methanethiosulfonate), Milwaukee, WI.

Almer et al., Synthesis of Stereochemically Homogeneous Oligoribonucleoside All-Rp-Phosphorothioates by Combining H-Phosphonate Chemistry and Enzymatic Digestion, J. Chem. Soc., Chem. Commun., 1459-1460 (1994).

Almer, et al. A New Approach to Stereospecific Synthesis of P-chiral Phosphorothioates. Preparation of Diastereomeric Dithymidy1-(3'-5') Phosphorothioates, Chem. Commun., (3): 290-1 (2004).

Almer, et al. Solid Support Synthesis of all-Rp-oligo(ribonucleoside phosphorothioate)s, Nucleic Acids Research 24(19): 3811-3820 (1996).

Almer, H. et al., Synthesis of Diribonucleoside Phosphorothioates via Sterospecific Sulfurization of H-Phosphonate Diesters, J. Org. Chem., 57(23): 6163-6169 (1992).

Altschul, S.F. et al., Basic local alignment search tool, Journal of Molecular Biology, 215(3):403-410 (1990).

Altschul, S.F. et al., Gapped Blast and PSI-Blast: a new generation of protein database search programs, Nucleic Acids Research, 25(17):3389-3402 (1997).

Alul, R.H. et al., Oxalyl-CPG: a labile support for synthesis of sensitive oligonucleotide, Nucleic Acids Research, 19(7):1527-1532 (1991).

Alvarez, K. et al., Photocleavable Protecting Groups as Nucleobase Protections Allowed the Solid-Phase Synthesis of Base-Sensitive SATE-Prooligonucleotides, Journal of Organic Chemistry, 64(17): 6319-6328(1999).

(56) References Cited

OTHER PUBLICATIONS

Amarzguioui et al., Tolerance for mutations and chemical modifications in a siRNA, Nucleic Acids Research 31(2): 589-595 (2003).
Arai, K. et al., Synthesis and properties of novel 2'-O-alkoxymethyl-modified nucleic acids, Bioorganic & Medicinal Chemistry Letters, 21(21): 6285-6287 (2011).
Aristarkhova, L.N. et al., Investigation in the field of thiosulfonic acids. 28. alkyl esters of cyclopentane- and cyclohexanethiosulfonic acids, Journal of Organic Chemistry of the USSR, 6: 2454-2458 (1970).
Athyros, V.G. et al., Antisense technology for the prevention or the treatment of cardiovascular disease: the next blockbuster?, Expert Opin. Investig. Drugs, 17(7): 969-72(2008).
Ausin, C. et al., Assesment of heat-sensitive thiophosphate protecting groups in the development of thermolytic DNA oligonucleotide prodrugs, Tetrahedron, 66(1):68-79 (2010).
Bachelin et al., Structure of a Stereoregular Phosphorothioate DNA/RNA duplex, Nat. Struct. Biol., 5(4): 271-276 (1998).
Baek, M-S. et al., In Vitro Metabolic Stabilities and Metabolism of 2'-O-(Methoxyethyl) Partially Modified Phosphorothioate Antisense Oligonucleotides in Preincubated Rat or Human Whole Liver Homogenates, Oligonucleotides, 20(6): 309-316 (2010).
Ballas, Z.K. et al., Induction of NK Activity in Murine and Human Cells by CpG Motifs in Oligodeoxynucleotides and Bacterial DNA, J. Immunoll., 57: 1840-1845 (1996).
Barber, I. et al., The Prooligonucleotides Approach I: Esterase-Mediated Reversibility of Dithymidine S-Alkyl Phosphorothiolates to Dithymidine Phosphorothioates, Bioorganic and Medicinal Chemistry Letters, 5(6):563-568 (1995).
Barber, I. et al., The Prooligonucleotides Approach II: Synthesis and stability studies of chimeric oligonucleotide models, Bioorganic and Medicinal Chemistry Letters, 5(14):1441-1444 (1995).
Barnes, P.J. and Peterson, S. Efficacy and Safety of Inhaled Corticosteroids in Asthma, Am. Rev. Respir. Dis., 148: SI-S26 (1993).
Battistini et al., Stereoselective Synthesis of Cyclic Dinucloetide Phosphorothioates, Tetrahedron, 49(5): 1115-1132 (1993).
Bayever, E. et al., Systematic administration of a phosphorothioate oligonucleotide with a sequence complementary to p53 for acute myelogenous leukemia and myelodysplastic syndrome: intial results of a phase I trial, Antisense Research Development, 3(4):383-390 (1993).
Beal, P.A. et al., Second Structural Motif for Recognition of DNA by Oligonucleotide-Directed Triple-Helix Formation, Science, 251: 1360-1363 (1991).
Beaucage, S.L. and Iyer, R.P., Advances in the Synthesis of Oligonucleotides by the Phosphoramidite Approach, Tetrahedron, 48(12):2223-2311 (1992).
Benner, S.A. and Sismour, A.M., Synthetic biology, Nature Reviews Genetics, 6(7):533-543 (2005).
Berge, S.M. et al., Pharmaceutical salts, J. Pharm. Sci., 66(1):1-19 (1997).
Besch, R. et al, Specific Inhibition of ICAM-1 Expression Mediated by Gene Targeting with Triplex-forming Oligonucleotides, J. Biol. Chem., 277(26): 32473-32479 (2002).
Bisbal, C. and Silverman, R.H., Diverse functions of RNase L and implication in pathology, Biochimie, 89(6-7):789-798 (2007).
Block, E. et al., Allium Chemistry: Synthesis and Sigmatropic Rearrangements of Alk(en)yl 1-Propenyl Disulfide S-Oxides from Cut Onion and Garlic, Journal of the Ameican Chemical Society, 118(12): 2799-2810 (1996).
Bobkov, G.V. et al., Phosphoramidite building blocks for efficient incorporation of 2'-O-aminoethoxy(and propoxy)methyl nucleosides into oligonucleotides, Tetrahedron, 64: 6238-6251 (2008).
Bock, L.C. et al., Selections of single-stranded DNA molecules that bind and inhibit human thrombin, Nature, 355: 564-566 (1992).
Boczkowska, M. et al., Stereodefined Phosphorothioate Analogues of DNA: Relative Thermodynamic Stability of the Model PS-DNA/DNA and PS-DNA/RNA complexes, Biochemistry, 41: 12483-12487 (2002).
Bode, C. et al. CpG DNA as a vaccine adjuvant, Expert Rev. Vaccines, 10(4): 499-511 (2011).
Bodor, N. et al., A convenient synthesis of (acyloxy)alkyl .alpha.-ethers of phenols, The Journal of Organic Chemistry, 48(26):5280-5284 (1983).
Bohringer, M. et al., Why Pentose and not Hexose Nucleic Acids? Part II: Oligonucleotides of 2'3'-dideoxy-β-d-glucopyranosyl ('homo-DNA') production, Helvetica Chimica Acta, 75:1416-1477 (1992).
Bologna, J. et al., Uptake and Quantification of Intracellular Concentration of Lipophilic Pro-Oligonucleotides in HeLa Cells, Antisense and Nucleic Acid Drug Development, 12(1):33-41 (2002).
Bonora, G.M. et al., Large scale, liquid phase synthesis of oligonucleotides by the phosphoramidite approach, Nucleic Acids Research, 21(5): 1213-1217 (1993).
Boudreau, R.L. et al., Nonallele-specific silencing of mutant and wild-type huntingtin demonstrates therapeutic efficacy in Huntington's disease mice, 17(6): 1053-1063 (2009).
Braasch et al., RNA Interference in Mammalian Cells by Chemically-Modified RNA, Biochemistry 42(26): 7967-7975 (2003).
Brill, W. et al., Thioalkylation of Nucleoside-H-Phosphonates and Its Application to Solid Phase Synthesis of Oligonucleotides, Tetrahedron Letters, 36(5):703-706 (1995).
Brooks, P.C. et al., Insulin-like Growth Factor Receptor Cooperates with Integrin αvβ5 to Promote Tumor Cell Dissemination in Vivo, The Journal of Clinical Investigation, 99(6):1390-1398 (1997).
Brown, J.W.S. and Simpson, C.G., Splice Site Selection in Plant Pre-mRNA Splicing, Ann. Rev. Plant Physiol. Plant Mol. Biol., 49: 77-95 (1998).
Bumcrot, D et al., RNAi therapeutics: a potential new class of pharmaceutical drugs, Nat. Chem. Biol., 2: 711-9 (2006).
Bundgaard, H., (C) Means to Enhance Penetration. (1) Prodrugs as a means to improve the delivery of peptide drugs, Advanced Drug Delivery Reviews, 8:1-38 (1992).
Bundgaard, H., Design and Application of Prodrugs, a Textbook of Drug Design and Development, Edited by Krogsgaard-Larsen, P. and Bundgaard, H., Chapter 5: 113-191 (1991).
Bundgaard, H., Design of Prodrugs, Elsevier, 7-9 and 21-24 (Chapter 1) (1985).
Bunnell. B.A. et al., Targeted Delivery of Antisense Oligonucleotides by Molecular Conjugates, Somatic Cell and Molecular Genetics, 18(6):559-569 (1992).
Burgers et al., Absolute configuration of the diastereomers of adenosine 5' -O-(1-thiaotriphosphate): Consequences for the stereochemistry of polymerization by DNA-dependent RNA polymerase from *Escherichia coli*, Proceedings of the National Academy of Sciences of the United States of America 75(10): 4798-4800 (1978).
Campbell, J. et al., Hybrid polymer/MOF membranes for Organic Solvent Nanofiltration (OSN): Chemical modification and the quest for perfection, Journal of Membrane Science, 503: 166-176 (2016).
Carbone, G.M. et al., Selective inhibition of transcription of the Ets2 gene in prostate cancer cells by a triplex-forming oligonucleotide, Nucl. Acid. Res., 31: 833-843 (2003).
Carrillo, H., and Lipman, D.J., The multiple sequence alignment problem in biology, SIAM J. Appl. Math., 48:1073-1082 (1988).
CAS Registry No. 1225524-67-3; STN Entry Date May 28, 2010; α-[(2-methylphenyl)methyl]-2-Pyrrolidinemethanol.
CAS Registry No. 1225524-68-4; STN Entry Date May 28, 2010; α-[(4-methylphenyl)methyl]-2-Pyrrolidinemethanol.
CAS Registry No. 1225545-00-5; STN Entry Date May 28, 2010; α-[(2,4,6-trimethylphenyl)methyl]-2-Pyrrolidinemethanol.
CAS Registry No. 1225554-20-0; STN Entry Date May 28, 2010; α-[(4-ethylphenyl)methyl]-2-Pyrrolidinemethanol.
CAS Registry No. 1225594-74-0; STN Entry Date May 28, 2010; α-[(2-chloro-6-fluorophenyl)methyl]-2-Pyrrolidinemethanol.
CAS Registry No. 1225682-42-7; STN Entry Date May 30, 2010; α-[(4-chlorophenyl)methyl]-2-Pyrrolidinemethanol.

(56) References Cited

OTHER PUBLICATIONS

CAS Registry No. 1226037-41-7; STN Entry Date May 30, 2010; α-[(3-chlorophenyl)methyl]-2-Pyrrolidinemethanol.
CAS Registry No. 1226118-97-3; STN Entry Date May 30, 2010; α-[(3-bromophenyl)methyl]-2-Pyrrolidinemethanol.
CAS Registry No. 1226119-02-3; STN Entry Date May 30, 2010; α-[(4-bromophenyl)methyl]-2-Pyrrolidinemethanol.
CAS Registry No. 1226146-65-1; STN Entry Date May 30, 2010; α-[(2,4-dimethylphenyl)methyl]-2-Pyrrolidinemethanol.
CAS Registry No. 1226160-20-8; STN Entry Date May 30, 2010; α-[(2,5-dimethylphenyl)methyl]-2-Pyrrolidinemethanol.
CAS Registry No. 1226178-36-4; STN Entry Date May 30, 2010; α-[(2-fluorophenyl)methyl]-2-Pyrrolidinemethanol.
CAS Registry No. 1226188-06-2; STN Entry Date May 30, 2010; α[[4-(1-methylethyl)phenyl]methyl]-2-Pyrrolidinemethanol.
CAS Registry No. 1226204-20-1; STN Entry Date May 30, 2010; α-[(3-methylphenyl)methyl]-2-Pyrrolidinemethanol.
CAS Registry No. 1226231-44-2; STN Entry Date May 30, 2010; α-[(2-chlorophenyl)methyl]-2-Pyrrolidinemethanol.
CAS Registry No. 1226352-28-8; STN Entry Date May 30, 2010; α-[(2,4-dichlorophenyl)methyl]-2-Pyrrolidinemethanol.
CAS Registry No. 1226352-38-0; STN Entry Date May 30, 2010; α-[(3,4-dichlorophenyl)methyl]-2-Pyrrolidinemethanol.
CAS Registry No. 1226413-27-9; STN Entry Date May 30, 2010; α-(phenylmethyl)-2-Pyrrolidinemethanol.
CAS Registry No. 1226419-15-3; STN Entry Date May 30, 2010; α-[(4-fluorophenyl)methyl]-2-Pyrrolidinemethanol.
CAS Registry No. 1263282-82-1 ; STN Entry Date Feb. 21, 2011; (S)-[(diphenyl)methyl]-2-Pyrrolidinemethanol.
CAS RN 78-96-6, Entered STN: Nov. 16, 1984.
Chatgilialoglu, C. and Snieckus, V., Chemical Synthesis: Gnosis to Prognosis, Kluwer Academic, 293-340 (1996).
Check, E., RNA interference: hitting the on switch, Nature, 448(7156): 855-858 (2007).
Chiu, Y. and Rana, T.M., siRNA function in RNAi: A chemical modification analysis, RNA, 9(9):1034-1048 (2003).
Cieslak, J. et al., Thermolytic 4-methylthio-1-butyl group for phosphate/thiophosphate protection in solid-phase synthesis of DNA oligonucleotides, Journal of Organic Chemistry, 69(7):2509-2515 (2004).
Clark, J.H, Flouride IOn as a Base in Organic Synthesis, Chemical Reviews, 1980 American Chemical Society 80(5): 429-452 (1980).
Communication Relating to the Results of the Partial International Search of PCT/IB2015/000395, Annex to Form PCT/ISA/206, 3 pages (Aug. 24, 2015).
Conway, N., The introduction of reporter groups at multiple and/or specific sites in DNA containing phosphorothioate diesters, Nucleic Acids Research, 43-44 (1989).
Cooney, M., et al., Site-Specific Oligonucleotide Binding Represses Transcription of the Human c-myc Gene in Vitro, Science, 241: 456-459 (1988).
Cosstick, R. and Eckstein, F., Synthesis of d(GC) and d(CG) Octamers Containing Alternating Phosphorothioate Linkages: Effect of the Phosphorothioate Group on the B-Z Transition, Biochemistry, 24: 3630-3638 (1985).
Coughlin, J.E. et al., Orally bioavailable anti-HBV dinucleotide acyloxyalkyl prodrugs, Bioorganic and Medicinal Chemistry Letters, 20(5):1783-1786 (2010).
Cox, J.R. and Ramsay, O.B., Mechanisms of Nucleophilic Substitution in Phosphate Esters, Chemical Reviews, 64(4): 317-352, (1964).
Crary, S.M. et al., Specific phosphorothioate substitutions probe the active site of *Bacillus subtilis* ribonuclease P, RNA, 8:933-947 (2002).
Crooke, S.T. and Geary, R.S. Clinical pharmacological properties of mipomersen (Kynamro), a second generation antisense inhibitor of apolipoprotein B, Br. J. Clin. Pharmacol., 76: 269-276 (2012).
Crooke, S.T., Molecular mechanisms of action of antisense drugs, Biochemica et Biophysica Acta, 1489: 31-44 (1999).
Cullen, K.A. et al., Ambulatory surgery in the United States, 2006, National Health Statistics Reports, 11: 1-28 (Jan. 28, 2009-Revised Sep. 4, 2009).
Current Protocols in Nucleic Acid Chemistry, Edited by Beaucage, S.L. et al., Chapter 2: Protection of Nucleosides for Oligonucleotide Synthesis, 2.0.1.-2.16.31 (2012).
Davis, B.G. et al., Altering the specificity of subtilisin bacillus lentus through the introduction of positive charge at single amino acid sites, Bioorganic & Medicinal Chemistry, 7(11): 2303-2311 (1999).
De Koning, M.G. et al., Simple and Efficient Solution-Phase Synthesis of Oligonucleotides Using Extractive Work-Up, Organic Process Research & Developmen, 10: 1238-1245 (2006).
Deleavey, G.F. and Damha, M.J., Designing chemically modified oligonucleotides for targeted gene silencing. Chem. Biol., 19: 937-54 (2012).
Dellinger, D.J. et al., Streamlined Process for the Chemical Synthesis of RNA Using 2'-O-Thionocarbamate-Protected Nucleoside Phosphoramidites in the Solid Phase, J. Am. Chem. Soc., 133: 11540-11556 (2011).
Devereux, J. et al., A comprehensive set of sequence analysis programs for the VAX, Nucleic Acids Research, 12(1):387-395 (1984).
Dietz, G.P.H. et al., Delivery of bioactive molecules into the cell: the Trojan horse approach, Molecular and Cellular Neuroscience, 27(2): 85-131 (2004).
Djukanovic, R. et al., Mucosal Inflammation in Asthma, Am. Rev. Respir. Dis., 142: 434-457 (1990).
Documents submitted to the U.S. Securities and Exchange Commission (SEC), Wave Life Sciences Ltd. CIK#: 0001631574 (2015-). Additional documents available through EDGAR of SEC, URL: <http://www.sec.gov/cgi-bin/browse-edgar?company=wave+life+sciences&owner=exclude&action=getcompany>.
Dorman et al., Synthesis of Oligodeoxynucleotides and Oligodeoxynucleotide Analogs using Phosphoramidite Intermediates, Tetrahedron, 40(1):95-102 (1984).
Dua, P. et al., Patents on SELEX and therapeutic aptamers, Recent Patents on DNA & Gene Sequences, 2(3):172-186 (2008).
Eaton, W.A. et al., Submillisecond kinetics of protein folding, Curr. Opin. Chem. Biol., 1:10-14 (1997).
Eckstein, F. et al., Stereochemistry of polymerization by DNA-dependent RNA-polymerase from *Escherichia coli*: an investigation with a diastereomeric ATP-analogue, Proc. Natl. Acad. Sci. USA, 73: 2987-90 (1976).
Eckstein, F. Phosphorothioates, Essential Components of Therapeutic Oligonucleotides, Nucleic Acid Therapeutics, 1-14 (2014).
Eckstein, F., Oligonucleotides and Analogues a Practical Approach, IRL Press, 1-24 (1991).
Egli, M. et al., Crystal structure of homo-DNA and nature's choice of pentose over hexose in the genetic system, Journal of the American Chemical Society, 128(33):10847-56 (2006).
Egli, M. et al., Probing the Influence of Stereoelectronic Effects on the Biophysical Properties of Oligonucleotides: Comprehensive Analysis of the RNA Affinity, Nuclease Resistance, and Crystal Structure of Ten 2'-0-Ribonucleic Acid Modifications, Biochemistry, 44: 9045-9057 (2005).
El Harchaoui, K. et al., Current and future pharmacologic options for the management of patients unable to achieve low-density lipoprotein-cholesterol goals with statins, Am. J. Cardiovasc. Drugs, 8(4): 233-242 (2008).
Elbashir, S.M. et al., Duplexes of 21-nucleotide RNAs mediate RNA interference in cultured mammalian cells, Nature, 411: 494-498 (2001).
Elbashir, S.M. et al., Functional anatomy of siRNAs for mediating efficient RNAi in *Drosophila melanogaster* embryo lysate, The EMBO Journal, 20(23): 6877-6888 (2001).
Ellington, A.D. and Szostak, J.W., In vitro selection of RNA molecules that bind specific ligands, Nature, 346: 818-822 (1990).

(56) References Cited

OTHER PUBLICATIONS

Engelhardt, J.A. et al., Scientific and Regulatory Policy Committee Points-to-consider Paper: Drug-induced Vascular Injury Associated with Nonsmall Molecule Therapeutics in Preclinical Development: Part 2. Antisense Oligonucleotides, Toxicologic Pathology, XX: 1-10 (2015).
Epton, R., Innovation and Perspectives in Solid Phase Synthesis, Peptides, Proteins and Nucleic Acids, 21:157-162 (1994).
Eschenmoser, A. et al., Why pentose- and not hexose-nucleic acids? Introduction to the problem, conformational analysis of oligonucleotide single strands containing 2', 3'-dideoxyglucopyranosyl building blocks ('homo-DNA'), and reflections on the conformation of A-and B-DNA, Helvetica Chimica Acta, 75:218-259 (1992).
Eschenmoser, A., Chemical etiology of nucleic acid structure, Science, 284(5423):2118-24 (1999).
Eschenmoser, A., Towards a Chemical Etiology of the Natural Nucleic Acids' Structure, Chemical Synthesis, Edited by Chatgilialoglu, C. and Snieckus, V., Kluwer Academic Publishers, 293-340 (1996).
Famulok, M. Oligonucleotide aptamers that recognize small molecules, Curr. Opin. Struct. Biol., 9: 324-329 (1999).
Fendrich et al., Determination of the Absolute P-configuration of a Phthalidyl[Phosphonate Thymidine-Thymidine Dimer, Nucleosides Nucleotides Nucleic Acids., 22(5-8): 1127-1129 (2003).
Ferreira, F. et al., Lewis acid deprotection of silyl-protected oligonucleotides and base-sensitive oligonucleotide analogues, Tetrahedron Letters, 45(33):6287-6290 (2004).
File Registry on STN, RN 18217-60-2, Entered STN: Nov. 16, 1984.
File Registry on STN, RN 871246-91-2, Entered STN: Jan. 5, 2006.
Fire, A. et al., Potent and specific RNA interference by double-stranded RNA in *Caenorhadbditis elegans*, Nature, 391: 806-811 (1998).
Forster, A.G. and Symons, R.H. Self-cleavage of plus and minus RNAs of a virusoid and a structural model for the active sites, Cell, 49(2): 211-220 (1987).
Forster, A.C. and Symons, R.H. Self-Cleavage of Virusoid RNA is performed by the Proposed 55-Nucleotide Active Site, Cell, 50: 9-16 (1987).
Frank-Kamenetsky, M. et al., Therapeutic RNAi targeting PCSK9 acutely lowers plasma cholesterol in rodents and LDL cholesterol in nonhuman primates. Proc. Natl. Acad. Sci. USA., 105(33): 11915-11920 (2008).
Frazier, K. et al., Potential Mechanisms of vascular toxicity in Monkeys with antisense oligonucleotides, TIDES oligo conference, 1-25 (May 15, 2014).
Frazier, K.S. Antisense Oligonucleotide Therapies: The Promise and the Challenges from a Toxicologic Pathologists Perspective, Toxicology Pathology, 43: 78-89 (2015).
Frederiksen, J.K. et al., Separation of RNA Phosphorothioate Oligonucleotides by HPLC, Methods of Enzymology, 468:289-309 (2009).
Freier, S.M. et al., Improved free-energy parameters for predictions of RNA duplex stability, Proc. Nat. Acad. Sci. USA, 83: 9373-9377 (1986).
Froehler, B.C. et al., Synthesis of DNA via deoxynucleoside H-phosphonate intermediates, Nucleic Acids Research, 14(13): 5399-5407 (1986).
Fujii et al., Acylphosphonates. 5.1A new method for stereospecific generation of phosphorothioate via aroylphosphonate intermediate, Tetrahedron Letters, 27(8): 935-938 (1986).
Fujii et al., Acylphosphonates. 7.1 A New Method for Stereospecific and Stereoselective Generation of Dideoxyribonucleoside Phosphorothioates via the Acylphosphonate Intermediates, Tetrahedron, 43: 3395-3407 (1987).
Gaffney, P.R.J. et al., Liquid-Phase Synthesis of 2'-Methyl-RNA on a Homostar Support through Organic-Solvent Nanofiltration, Chem. Eur. J., 21:1-10 (2015).
Ganguly, A.K. et al., Structure of Halomicin B, J.C.S. Chem. Comm., 395-396 (1974).
Garegg, P.J. et al., Nucleoside H-Phosphonates. III. Chemical Synthesis of Oligodeoxyribonucleotides by the Hydrogenphosphonate Approach, Tetrahedron Letters, 27(34): 4051-4054 (1986).
Gauglitz, G.G. et al., Hypertrophic Scarring and Keloids: Pathomechanisms and Current Emerging Treatment Strategies, Mol. Med., 17(1-2): 113-125 (2011).
Gijsen, H.J.M et al., Development of two diastereoselective rougtes towards trans-4-aminomethyl-piperidin-3-o1 building blocks, Tetrahedron 64(10): 2456-2464 (2008).
Goraczmiak, R. et al., Gene silencing by synthetic U1 Adaptors, Nature Biotechnology 27(3): 257-263 (2008).
Gosselin, G. et al., New insights regarding the potential of the pronucleotide approach in antiviral chemotherapy, 43(1):195-208 (1996).
Gough, G.R. et al., Recovery and recycling of synthetic units in the construction of oligodeoxyribonucleotides on solid supports, Tetrahedron Letters, 22(42): 4177-4180 (1981).
Graham, M.J. et al., Antisense inhibition of proprotein convertase subtilisin/kexin type 9 reduces serum LDL in hyperlipidemic mice, J. Lipid Res., 48(4): 763-767 (2007).
Grajkowski, A. et al., Design and Development of Thermolytic DNA Oligonucleotide Prodrugs, Annals of the New York Academy of Sciences, 1058:26-38 (2005).
Grajkowski, A. et al., Solid-Phase Synthesis of Thermolytic DNA Oligonucleotides Functionalized with a Single 4-Hydroxy-1-butyl or 4-Phosphato-/Thiophosphato-1-butyl Thiophosphate Protecting Group, Journal of Organic Chemistry, 72(3): 805-815 (2007).
Grajkowski, A. et al., Thermolytic CpG-containing DNA oligonucleotides as potential immunotherapeutic prodrugs, Nucleic Acids Research, 33(11):3550-3560 (2005).
Green, L.S. et al., Inhibitory DNA Ligands to Platelet-Derived Growth Factor B-Chain, Biochemistry, 35: 14413-14424 (1996).
Green, L.S. et al., Nuclease-resistant nucleic acid ligands to vascular permeability factor/vascular endothelial growth factor, Chem. Biol., 2(10): 683-695 (1995).
Griffiths-Jones, S. et al., miRBase: microRIVA sequences, targets and gene nomenclature, Nucleic Acids Research, 34 (Database Issue): D140-D144 (2006).
Griffiths-Jones, S. The microRNA Registry, Nucleic Acids Research, 32 (Database Issue): D109-D111 (2004).
Groebke, K. et al., Why pentose and not hexose nucleic acids? Part V. Purine-purine pairing in homo-DNA: guanine, isoguanine, 2,6-diaminopurine and xanthine. Helvetica Chimica Acta. 81: 375-474 (1998).
Gude, L. et al., Mapping Targetable Sites on Human Telomerase RNA Pseudoknot/Template Domain Using 2'-OMe RNA-interacting Polynucleotide (RIPtide) Microarrays, J. Biol. Chem., 287(22): 18843-18853 (2012).
Guerlavais-Dagland, T et al., Fluoride-labile protecting groups for the synthesis of base-sensitive methyl-SATE oligonucleotide prodrugs, European Journal of Organic Chemistry, 2003(12):2327-2335 (2003).
Guga et al., Oxathiaphospholane Approach to the Synthesis of P-Chiral, Isotopomeric Deoxy(ribonucleoside phosphorothioate)s and Phosphates Labeled with an Oxygen Isotope. Angew Chem., 113(3): 630-633 (2001).
Guga et al., Unusual Thermal Stability of RNA/[RP-PS]-DNA/RNA Triplexes Containing a Homopurine DNA Strand, Biophys J., 92(7): 2507-2515 (2007).
Guga, P. and Stec, W.J., Synthesis of Phosphorothioate Oligonucleotides with Stereodefined Phsphorothioate Linkages, Current Protocols in Nucleic Acid Chemistry, Unit 4.17: 4.17.1-4.17.28 (2003).
Guga, P., P-chiral oligonucleotides in biological recognition processes, Current Topics in Medicinal Chemistry, 7:695-713 (2007).
Guo, M. et al., Solid-phase stereoselective synthesis of 2'-0-methyl-oligo-ribonucleoside phosphorothioates using nucleoside bicyclic oxazaphospholidines, Biorganic & Medicinal Chemistry Letters, 8(18):2539-2544 (1998).
Guzaev, A.P., Reactivity of 3H-1,2,4-dithiazole-3-thiones and 3H-1,2-dithiole-3-thiones as sulfurizing agents for oligonucleotide synthesis, Tetrahedron Letters, 52: 434-437 (2011).

(56) References Cited

OTHER PUBLICATIONS

Hacia, J.G. et al., Phosphorothioate oligonucleotide-directed triple helix formation, Biochemistry, 33:5367-5369 (1994).

Hammond, S.M. and Wood, M.J. Genetic therapies for RNA mis-splicing diseases, Trends Genet., 27: 196-205 (2011).

Hanagata, N., Structure-dependent immunostimulatory effect of CpG oligodeoxynucleoties and their delivery system, Int. J. Nanomedicine, 7: 2181-95 (2012).

Hansen et al., Azaribofuranoside Analogues as Designed Inhibitors of Purine Nucleoside Phosphorylase, Synthesis and Biological Evaluation, Acta Chemis Scandinavica 52: 1214-1222 (1998).

Harper, S.Q. et al., RNA interference improves motor and neuropathological abnormalities in a Huntington's disease mouse model, Proc. Natl. Acad. Sci. USA, 102(16): 5820-5825 (2005).

Hartmann, B. et al., Sequence effects on energetic and structural properties of phosphorothioate DNA: a molecular modelling study, Nucleic Acids Research, 27(16): 3342-3347 (1999).

Hartmann, G. et al., Delineation of a CpG Phosphorothioate Oligodeoxynucleotide for Activating Primate Immune Responses in Vitro and in Vivo, The Journal of Immunology, 164(3): 1617-1624 (2000).

Hau, P. et al., Results of G004, a phase IIb actively controlled clinical trial with the TGF-b2 targeted compound AP 12009 for recurrent anaplastic astrocytoma, Journal of Clinical Oncology, 2006 ASCO Annual Meeting Proceedings (Post Meeting Edition), 24(18, Jun. 20 Supplement): 1566 (2006).

Hayashi, S. et al., Studies on Antitumor Substances, Chemical & Pharmaceutical Bulletin, 12(11): 1271-1276 (1964).

Heger, W. et al., Embryotoxic effects of thalidomide derivatives on the non-human primate Callithrix jacchus; 3. Teratogenic potency of the EM 12 enantiomers, Arch. Toxicol., 62: 205-208 (1988).

Henry, A.A. and Romesberg, F.E., Beyond A, C, G and T: augmenting nature's alphabet, Current Opinion in Chemical Biology, 7(6): 727-733 (2003).

Henry, S.P. et al., Activation of the Alternative Pathway of Complement by a Phosphorothioate Oligonucleotide: Potential Mechanism of Action, The Journal of Pharmacology and Experimental Therapeutics, 281(2): 810-816 (1997).

Herbert, B-S. et al., Nonradioactive detection of telomerase activity using the telomeric repeat amplification protocol, Nat. Protoc., 1(3): 1583-1590 (2006).

Herdewijn, Oligonucleotide Synthesis, Methods in Molecular Biology, 288: 1-435 (2005).

Heuberger, B.D. and Switzer, C., A Pre-RNA Candidate Revisited: Both Enantiomers of Flexible Nucleoside Triphosphates are DNA Polymerase Substrates, Journal of the American Chemical Society, 130(2):412-413 (2008).

Higuchi, T. et al., Pro-drugs as Novel Delivery Systems, ACS Symposium Series, 14 (1975).

Hirao, I., Unnatural base pair systems for DNA/RNA-based biotechnology, Current Opinion in Chemical Biology,10:622-627 (2006).

Hohjoh, H., Disease-Causing Allele-Specific Silencing by RNA Interference, Pharmaceuticals, 6: 522-535 (2013).

Hunziker, J. et al., Why Pentose-and Not Hexose-Nucleic Acids? Part III. Oligo(2',3'-dideoxy-β-D-glucopyranosyl)nucleotides. ('Homo-DNA'): Base-Pairing Properties, Helvetica Chimica Acta, 76(1):259-352 (1993).

Inagawa, T. et al., Inhibition of human immunodeficiency virus type 1 replication by P-stereodefined oligo(nucleoside phosphorothioate)s in a long-term infection model, FEBS Letters, 528(1-3): 48-52 (2002).

International Preliminary Report on Patentability and Written Opinion of the Searching Authority for PCT/JP2011/055018 (Oct. 11, 2012) with English Translation thereof.

International Preliminary Report on Patentability for Application No. PCT/JP2010/065900, 6 pages (Mar. 29, 2012).

International Preliminary Report on Patentability for Application No. PCT/JP2010/065900, 7 pages (Apr. 19, 2012). (English Translation).

International Preliminary Report on Patentability for Application No. PCT/JP2011/071559, 7 pages (Apr. 25, 2014).

International Preliminary Report on Patentability for PCT/JP2013/004303, 1 page (Jan. 13, 2015).

International Search Report for PCT/IB2009/007923, 4 pages (Sep. 6, 2010).

International Search Report for PCT/IB2015/000395, 7 pages (Oct. 30, 2015).

International Search Report for PCT/JP11/71559, 3 pages (Dec. 20, 2011).

International Search Report for PCT/JP2010/065900, 1 page (Sep. 15, 2010).

International Search Report for PCT/JP2011/077313, 2 pages (Jan. 10, 2012).

International Search Report for PCT/JP2011/55018 (Mar. 29, 2011).

International Search Report for PCT/JP2013/004303, 3 pages (Aug. 13, 2013).

International Search Report for PCT/US2010/041068, 1 page (Sep. 1, 2010).

International Search Report for PCT/US2011/064287, 2 pages (Apr. 12, 2012).

International Search Report for PCT/US2012/046805, 2 pages (Sep. 19, 2012).

International Search Report for PCT/US2013/050407, 5 pages (Jan. 9, 2014).

Isis Pharmaceuticals, Intellectual Property: Capturing Value From Innovation, Isis' Annual Meeting of Stockholders and Open House, Intellectual Property Poster, 1 page (2011). Received from Internet <http://www.isispharm.com/Site_Gfx/pdf/11-AnMtg_IntellectualProperty_TAB.pdf>.

Isis Pharmaceuticals, Intellectual Property: Capturing Value From Innovation, Isis' Annual Meeting of Stockholders and Open House, Intellectual Property Poster, 1 page (2012). Received from Internet <http://www.isispharm.com/Site_Gfx/pdf/2012_Annual_Meeting_IP_Poster.pdf>.

Iwamoto et al., Stereocontrolled Synthesis of H-phosphonate DNA, Nucleic Acids Symposium Series, (50):159-60 (2006).

Iwamoto, N. et al., Stereocontrolled solid-phase synthesis of oligonucleoside H-phosphonates by an oxazaphospholidine approach, Angewandte Chemie International Edition, 48(3):496-499 (2009).

Iyer, R.P. et al., A novel nucleoside phosphoramidite synthon derived from 1R, 2S-ephedrine, Tetrahedron Asymmetry 6(5):1051-1054 (1995).

Iyer, R.P. et al., Acyloxyaryl prodrugs of oligonucleoside phosphorothioates, Bioorganic and Medicinal Chemistry Letters, 6(16):1917-1922 (1996).

Iyer, R.P. et al., Bioreversible oligonucleotide conjugates by site-specific derivatization, Bioorganic and Medicinal Chemistry Letters, 7:871-876 (1997).

Iyer, R.P. et al., Stereospecific Bio-Reversibility of Dinucleoside S-Alkyl Phosphorothiolates to Dinucleoside Phosphorothioates, Bioorganic & Medicinal Chemistry Letter, 4(20):2471-2476 (1994).

Iyer, R.P., et al., 3H-1,2-Benzodithiole-3-one 1,1-Dioxide as an Improved Sulfurizing Reagent in the Solid-Phase Synthesis of Oligodeoxyribonucleoside Phosphorothioates, Journal of the American Chemical Society, 112(3):1253-1254 (1990).

Iyer, R.P., et al., Prodrugs of Oligonucletides: The Acyloxyalkyl Esters of Oligodeoxyribonucleoside Phosphorothioates, Bioorganic Chemistry, 23:1-21 (1995).

Iyer, R.P., et al., Solid-phase stereoselective synthesis of oligonucleoside phosphorothioates: The nucleoside bicyclic oxazaphospholidines as novel synthons, Tetrahedron Letters, 39:2491-2494 (1998).

Jahns, H., et al., Stereochemical bias introduced during RNA synthesis modulates the activity of phosphorothioate siRNAs, Nat. Commun., 6: 6317 (2015).

Jiang, J. et al., Allele-Specific Silencing of Mutant Myh6 Transcripts in Mice Suppresses Hypertrophic Cardiomyopathy, Science, 342: 111-114 (2013).

Jin et al., A Stereoselective Synthesis of Dinucleotide Boranophosphate, Using Chiral Indole-Oxazaphosphorine Intermediates, Tetrahedron Letters, 39: 6433-6436 (1998).

(56) References Cited

OTHER PUBLICATIONS

Jin et al., Stereoselective Synthesis of Dithymidine Phosphorothioates Using Xylose Derivatives as Chiral Auxiliaries, J. Org. Chem., 63(11): 3647-3654 (1998).
Johansson et al., Studies towards synthesis of dinucleoside arylphosphonates with metal complexing properties, Nucleosides Nucleotides & Nucleic Acids, 22(5-8): 1459-61 (2003).
Johansson et al., Synthesis of dinucleoside pyridylphosphonates involving palladium(o)-catalysed phosphorus-carbon bond formation as a key step, Chem. Commun., 2564-2565 (2001).
Johansson et al., The case for configurational stability of H-phosphonate diesters in the presence of diazabicyclo[5.4.0]undec-7-ene (DBU), Bioorg Med Chem., 9(9): 2315-22 (2001).
Jopling, C.L. et al., Modulation of Hepatitis C Vicus RNA Abundance by a Liver-Specific MicroRNA, Science, 309: 1577-1581 (2005).
Joyce, G.F. et al., The case for an ancestral genetic system involving simple analogues of the nucleotide, Proceedings of the National Academy of Sciences, 84:4398-4402 (1987).
Joyce, G.F. The antiquity of RNA-based evolution, Nature, 418(6894): 214-221 (2002).
Kakeya, N. et al., Studies on Prodrugs of Cephalosporins. I. Synthesis and Biological Properties of Glycyloxybenzoyloxymethyl and Glycylaminobenzoyloxymethyl Esters of 7-[2-(2-Aminothiazol-4-yl)-(Z)-2-methoxyiminoacetamido]-3-methyl-3-cephem-4-carboxylic Acid, Chem. Pharm. Bull., 32(2): 692-698 (1984).
Kamada, A.K. et al., Issues in the Use of Inhaled Glucocorticoids, Am. J. Respir. Crit. Care. Med., 153: 1739-1748 (1996).
Karwowski, B. et al., Stereocontrolled Synthesis of LNA Dinucleoside Phosphorothioate by the Oxathiaphospholane Approach, Bioorganic & Medicinal Chemistry Letters, 11: 1001-1003 (2001).
Kawasaki, A et. al., Uniformly Modified 2'-Deoxy-2'-fluoro Phosphorothioate Oligonucleotides as Nuclease-Resistant Antisense Compounds with High Affinity and Specificity for RNA Targets, J. Med. Chem., 36: 831-841 (1993).
Kay, C. et al., Huntingtin Haplotypes Provide Prioritized Target Panels for Allele-Specific Silencing in Huntington Disease Patients of European Ancestry, Molecular Therapy, Accepted Article Preview Online (Jul. 23, 2015).
Kers et al., A new type of nucleotide analogue with 4-pyridylphosphonate internucleotide linkage, Tetrahedron Letters, 40(22): 4263-4266 (1999).
Kihara, M et al., New norepinephrine potentiators: synthesis and structure-actvity relastionships of a series of 4-phenyl-1,2,3,4-tetrahydroisoquinolin-4-ols, Chemical & Pharmaceutical Bulletin 42(1): 67-73 (1994).
Kim, N.W. et al., Specific Association of Human Telomerase Activity with Immortal Cells and Cancer, Science, 226: 2011-2015 (1994).
Kim, S-H. and Cech, T.R., Three-dimensional model of the active site of the selfsplicing rRNA precursor of Tetrahymena, Proc. Natl. Acad. Sci. U S A., 84(24): 8788-8792 (1987).
Kim, S. et al., Liquid-Phase RNA Synthesis by Using Alkyl-Chain-Soluble Support, Chem. Eur. J., 19: 8615-8620 (2013).
Kiviniemi, A. et al., Solid-Supported 2'-O-Glycoconjugation of Oligonucleotides by Azidation and Click Reactions, Bioconjugate Chemistry, 22(6): 1249-1255 (2011).
Klose, J. et al., Preparation of 2-(2-Cyanoethyl)-sulfanyl-1H-isoindole-1,3-(2H)-dione and related sulfur transfer reagents, Tetrahedron, 53(42):14411-14416 (1997).
Kool, E.T., Replacing the Nucleobases in DNA with Designer Molecules, Accounts of Chemical Research, 35:936-943 (2002).
Kordasiewicz, H.B. et al., Sustained therapeutic reversal of Huntington's disease by transient repression of huntingtin synthesis, Neuron, 74(6): 1031-1044 (2012).

Kozikowski, A.P. et al., Chemistry of the main group metals: A stereoselective synthesis of allyl vinyl thioethers for the thio-claisen reaction, Journal of Organometallic Chemistry, 164(3): C33-C37 (1979).
Koziolkewicz et al., Stability of Stereoregular Oligo-(nucleoside Phosphorothioate)s in Human Plasma: Diastereoselectiviy of Plasma 3'-Exonuclease, Antisense Nucl. Acid Drug Dev., 7: 43-48 (1997).
Koziolkewicz et al., Stereodifferentiation—the effect of P chirality of oligo(nucleoside phosphorothioates) on the activity of bacterial RNase H, Nucl. Acids Res., 23(24): 5000-5005 (1995).
Koziolkiewicz, M. et al., Effect of P-chirality of oligo(deoxyribonucleoside phosphorothioate)s) on the activity of terminal deoxyribonucleotidyl transferase, FEBS Letters, 434(1-2): 77-82 (1998).
Koziolkiewicz, M., et al., Stereodifferentiation—the effect of P chirality of oligo(nucleoside phosphorothioates) on the activity of bacterial RNase H, Nucleic Acids Res., 23: 5000-5 (1995).
Kraszewski et al., Studies on Reactions of Nucleoside H-phosphonates with Bifunctional Reagents. Part 1. Reaction with amino alcohols, J. Chem. Soc., Perkin Trans., 1: 1699-1704 (1993).
Krieg, A.M. et al., CpG motifs in bacterial DNA trigger direct B-cell activation, Nature, 374: 546-549 (1995).
Krieg, A.M. et al., P-Chirality-Dependent Immune Activiation by Phosphorothioate CpG Oligodeoxynucleotides, Oligonucleotides, 13:491-499 (2003).
Krueger, A.T. et al., Synthesis and properties of size-expanded DNAs: toward designed, functional genetic systems, Accounts of Chemical Research, 40:141-150 (2007).
Krutzfeldt, J. et al., Silencing of microRNAs in vivo with 'antagomirs', Nature, 438: 685-689 (2005).
Kungurtsev, V. et al., Solution-Phase Synthesis of Short Oligo-2'-deoxyribonucleotides by Using Clustered Nucleosides as a Soluble Support, Eur. J. Org. Chem., 6687-6693 (2013).
Kwon, H-J. et al., NF-kappaB-dependent regulation of tumor necrosis factor-alpha gene expression by CpG-oligodeoxynucleotides, Biochem. Biophys. Res. Commun., 311(1): 129-138 (2003).
LaPlanche, L.A. et al., Phosphorothioate-modified oligodeoxyribonucleotides. III. NMR and UV spectroscopic studies of the Rp-Rp, Sp-Sp, and Rp-Sp duplexes, [d(GGsAATI'CC)2, derived from diastereomeric 0-ethyl phosphorothioates, Nucleic Acids Research, 14(22): 9081-9093 (1986).
Latimer, L.J.P. et al, Synthetic repeating sequence DNAs containing phosphorothioates: nuclease sensitivity and triplex formation, Nucleic Acids Research, 17(4): 1549-1561 (1989).
Laurent et al., Chiral and steric effects in the efficient binding of alpha-anomeric deoxyoligonucleoside N-alkylphosphoramidates to ssDNA and RNA, Nucleic Acids Res., 27(21): 4151-9 (1999).
Lavergne, T. et al., A Base-Labile Group for 2'-OH Protection of Ribonucleosides: A Major Challenge for RNA Synthesis, Chem. Eur. J, 14, 9135-9138 (2008).
Lesnikowski et al., Studies on Stereospecific Formation of P-Chiral Internucleotide Linkage. Synthesis of (RP, RP)- and (SP, SP)-Thymidylyl (3', 5') Thymidylyl (3', 5') Thymidine DI (O,O-Phosphorothioate) Using 2-Nitrobenzyl Group as a New S-Protection, Tetrahedron Letters 30(29)" 3821-3824 (1989).
Lesnikowski, Z. J. et al., Octa(thymidine methanephosphonates) of partially defined sterochemistry: synthesis and effect of chirality at phosphorus on binding to pentadecadeoxyriboadenylic acid, Nucleic Acids Research, 18(8): 2109-2115 (1990).
Levin, A.A. et al., Basic Principles of the Pharmacokinetics of Antisense Oligonucleotide Drugs, Antisense Drug Technology: Principles, Strategies, and Applications, Second Edition, Chapter 7: 183-215 (2008).
Li L.C., Small RNA Mediated Gene Activation, RNA and the Regulation of Gene Expression: A Hidden Layer of Complexity, Edited by Kevin V. Morris, Chapter 13, Caister Academic Press (2008).
Li, L-C. et al., Small dsRNAs induce transcriptional activation in human cells, PNAS, 103(46): 17337-17342 (2006).
Li-Tsang, C.W. et al., Prevalence of hypertrophic scar formation and its characteristics among the Chinese population, Burns, 31: 610-616 (2005).

(56) References Cited

OTHER PUBLICATIONS

Liang, X-h. et al., Identification and characterization of intracellular proteins that bind oligonucleotides with phosphorothioate linkages, Nucleic Acids Research, 43(5): 2927-2945, Supplemental Data pp. 1-20 (2015).
Lima, W. et al., Single-Stranded ssRNAi Activate RNAi in Animals, Cell, 150: 883-894 (2012).
Lima, W.F. et al., The influence of antisense oligonucleotide-induced RNA structure on *Escherichia coli* RNase H1 activity, J. Biol. Chem., 272(29):18191-9 (1997).
Lima, W.F., et al., Human RNase H1 discriminates between subtle variations in the structure of the heteroduplex substrate, Mol. Pharmacol., 71: 83-91 (2007).
Limbach, P.A. et al., Summary: the modified nucleosides of RNA, Nucleic Acids Research, 22(12):2183-2196 (1994).
Lin et al., Synthesis and resolution of dinucleotide (TpAZT) phosphoramidates, Synthetic Commun., 33(14): 2553-2562 (2003).
Linton, M.F., et al., Transgenic Mice Expressing High Plasma Concentrations of Human Apolipoproteins B100 and Lipoprotein (a), J. Clin. Invest., 92: 3029-37 (1993).
Liu, W. et al., Increased Steady-State Mutant Huntingtin mRNA in Huntington's Disease Brain, Journal of Huntington's Disease 2: 491-500 (2013).
Lu, X. et al., Antisense-Mediated Inhibition of Human Immunodeficiency Virus (HIV) Replication by Use of an HIV Type 1-Based Vector Results in Severely Attenuated Mutants Incapable of Developing Resistance, Journal of Virology, 78(13): 7079-7088 (2004).
Lu, Y. and Just, G., Stereoselective synthesis of dithymidine phosphorothioates using d-xylose derived chiral auxiliaries, Tetrahedron, 57(9):1677-1687 (2001).
Lu, Y. et al., Stereoselective Synthesis of R(P)- and S(P)-Dithymidine Phosphorothioates via Chiral Indolooxazaphosphorine Intermediates Derived from Tryptophan This work was financially supported by Natural Science and Engineering Research Council of Canada (NSERC). We thank Nadim Saadeh and Dr. Orval Mamer, McGill University biomedical mass spectroscopy unit, for recording mass spectra, Angewandte Chemie International Edition, 39(24):4521-4524 (2000).
Lu, Y., Recent advances in the stereocontrolled synthesis of anti-sense phosphorothioates, Mini Reviews in Medicinal Chemistry, 6(3): 319-330 (2006).
Machine Translation of JP 2010-265304 (2010). <http://dossier1.ipdl.inpit.go.jp/AIPN/odse_top_dn.ipdl?N0000=7400>.
Machytka et al., Extension of the Applicability of &I-Values for the Configurational Assignment of Diastereomeric Phosphate-Modified Dideoxynucleotides, Nucleosides and Nucleotides, 17(12): 2311-2322 (1998).
Machytka et al., Synthesis and NMR characterization of diastereomeric CPSMeG derivatives, Nucleosides Nucleotides Nucleic Acids., 19(5-6): 903-15 (2000).
Maher III, L.J., et al., Inhibition of DNA Binding Proteins by Oligonucleotide-Directed Triple Helix Formation, Science, 245: 725-730 (1989).
Mann, M.J. et al., Therapeutic applications of transcription factor decoy oligonucleotides, J. Clin. Invest., 106:1071-1075 (2000).
Mannironi, C. et al., In Vivo Selection of Dopamine RNA Ligands, Biochemistry, 36: 9726-9734 (1997).
Martin, P., A New Access to 2'-O-alkylated Ribonucleosides and Properties of 2'-O-Alkylated Oligoribonucleotides, Helv. Chim. Acta., Abstract Only, 78: 486-504 (1995).
Martin, P., Stereoselective Synthesis of 2'-O-(2-Methoxyethyl)ribonucleosides: Neighboring-Group Participation of the Methoxyethoxy Group in the Ribosylation Step, Helv. Chim. Acta, 79: 1930-1938 (1996).
Masahiro, T. et al., Nematicidal and antimicrobial constituents from *Allium grayi* Regel and *Allium fistulosum* L. var. caespitosum, Agricultural and Biological Chemistry, 52(9): 2383-2385 (1988).
Matsuno, Y. et al., Synthetic Method for Oligonucleotide Block by Using Alkyl-Chain-Soluble Support, Org. Lett., 18: 800-803 (2016).

Matysiak, S et al., Acetals as New 2'-O-Protecting Functions for the Synthesis of the Oligoribonucleotides: Synthesis of Uridine Building Blocks and Evaluatino of Their Relative Acid Stability, Helvetica Chimica Acta 81: 1545-1566 (1998).
Maung, J. et al., Alternatives to 1-H-tetrazole in the preparation of phosphonate diesters and phosphonamidates from phosphonyl dichlorides, Tetrahedron Lett., 45: 6497-6499 (2004).
Mauritz, R.P. et al., Elucidation of the Hydrolytical Properties of α-Hydroxybenzylphosphonates as a New Potential Pro-Oligonucleotide Concept, Nucleosides and Nucleotides, 18(6-7):1417-1418 (1999).
Mauritz, R.P. et al., Synthesis of 3',5'-Dithymidylyl-α-hydroxyphosphonate Dimer Building Blocks for Oligonucleotide Synthesis—A New Pro-oliguncleotide, Nucleosides and Nucleotides, 16(7-9):1209-1212 (1997).
McBride, J.L. et al., Prelinical Safety of RNAi-Mediated HTT Suppression in the Rhesus Macaque as a Potential Therapy for Huntington's Disease, Molecular Therapy, 19: 1-11 (2011).
Meade, M.F., et al., Efficient delivery of RNAi prodrugs containing reversible charge-neutralizing phosphotriester backbone modifications, Nat. Biotech., 32: 1256-61 (2014).
Medical News Today, AVI BioPharma Announces FDA Clears IND Applications for Clinical Trials of RNA Therapeutic Agents for Treatment of Ebola and Marburg Viruses, Accessed Apr. 2, 2015, 2 pages (Dec. 30, 2008).
Merki, E. et al., Antisense oligonucleotide directed to human apolipoprotein B-100 reduces lipoprotein(a) levels and oxidized phospholipids on human apolipoprotein B-1 00 particles in lipoprotein(a) transgenic mice, Circulation, 118(7): 743-53 (2008).
Mesmaeker, A.D. Backbone modifications in oligonucleotides and peptide nucleic acid systems, Current Opinion in Structural Biology, 5: 343-355 (1995).
Methods in Enzymology, Edited by Widder, K. and Green, R., Drug and Enzyme Targeting, Academic Press, 112: 309-396 (1985).
Mignet, N. et al., Synthesis and evaluation of glucuronic acid derivatives as alkylating agents for the reversible masking of internucleoside groups of antisense oligonucleotides, Carbohydrate Research, 303:17-24 (1997).
Mignet, N. et al., The Prooligonucleotide Approach. V: Influence of the phosphorus atom environment on the hydrolysis of enzymolabile dinucleoside phosphotriesters, Bioorganic and Medicinal Chemistry Letters, 7(7):851-854 (1997).
Milkowski, J.D. et al., Thiol Protection with the Acetamidomethyl Group: S-Acetamidomethyl-I-cysteine Hydrochloride, Organic Syntheses, 6: 5 (1988).
Misaki, S et al., Dehydration of 2-Trifluoromethyl-3,3,3-Trifluoropropanil with Base, Journal of Flourine Chemistry 24: 531-533 (1984).
Molina, A.G. et al., Acetylated and Methylated β-Cyclodextrins asViable Soluble Supports for the Synthesis of Short 2'-Oligodeoxyribo-nucleotides in Solution, Molecules, 17: 12102-12120 (2012).
Molina, A.G. et al., Assembly of Short Oligoribonucleotides from Commercially Available Building Blocks on a Tetrapodal Soluble Support, Current Organic Synthesis, 12: 1-6 (2015).
Molina, A.G. et al., Solution phase synthesis of short oligoribonucleotides on a precipitative tetrapodal support, Beilstein Journal of Organic Chemistry, 10: 2279-2285 (2014).
Molina, A.G., Synthesis of Short Oligonucleotides on a Soluble Support by the Phosphoramidite Method, University of Turku, 1-66 (2015).
Monteys, A.M. et al., Single nucleotide seed modification restores in vivo tolerability of a toxic artificial miRNA sequence in the mouse brain, Nucleic Acids Res., 42(21): 13315-13327 (2014).
Morales-Rojas, H. and Kool, E.T., A porphyrin C-nucleoside incorporated into DNA, Organic Letters, 4(25):4377-4380 (2002).
Morcos, P.A., Achieving targeted and quantifiable alteration of mRNA splicing with Morpholino oligos, Biochem. Biophys. Res. Commun., 358(2): 521-527 (2007).
Morvan, F. et al., Cellular uptake and intracellular quantification of fluorescent labeled T20 Me-SATE prooligonucleotides, Nucleosides Nucleotides Nucleic Acids, 20(4-7):1165-1168 (2001).

(56) References Cited

OTHER PUBLICATIONS

Morvan, F. et al., Kinetics study of the biotransformation of an oligonucleotide prodrug in cells extract by matrix-assisted laser desorption/ionization time-of-flight mass spectrometry, Nucleosides, Nucleotides and Nucleic Acids, 20(2-4):1159-1163 (2001).
Morvan, F. et al., The Oligonucleotide Prodrug Approach: The Pro-Oligonucleotides, Pharmaceutical Aspects of Oligonucleotides, 79-97 (2000).
Moser, H. E. et al., Sequence-Specific Cleavage of Double Helical DNA by Triple Helix Formation, Science, 238: 645-650 (1987).
Nawrot et al., DNA Oligonucleotides Containing Stereodefined Phosphorothioate Linkages in Selected Positions, Current Protocols in Nucleic Acid Chemistry, Unit 4.34: 4.34.1-4.34.15 (2009).
Nielsen, J. and Caruthers, M.H., Directed Arbuzov-type reactions of 2-cyano-1,1-dimethylethyl deoxynucleoside phosphites, J. Am. Chem. Soc., 110: 6275-6 (1988).
Nielsen, N.M. and Bundgaard, H. Glycolamide Esters as Biolabile Prodrugs of Carboxylic Acid Agents: Synthesis, Stability, Bioconversion, and Physicochemical Properties, Journal of Pharmaceutical Sciences, 77(4): 285-298 (1988).
Nieuwlandt, D. et al., In Vitro Selection of RNA Ligands to Substance P, Biochemistry, 34: 5651-5659 (1995).
Nilsson et al., Chemical and Stereochemical Aspects of Oxidative Coupling of H-Phosphonate and H-Phosphonothioate Diesters. Reactions with N,N-,N,O and O,O-Binucleophiles, Letters in Organic Chemistry, 2(2): 188-197 (2005).
Nilsson et al., Controlling Stereochemistry During Oxidative Coupling. Preparation of Rp or Sp Phosphoramidates from One P-chiral Precursor, Chem. Commun., (22): 2566-7 (2004).
Nilsson, J. et al., Chemoselectivity in oxidative coupling of bifunctional nucleophiles with dinucleoside H-phosphonate and dinucleoside H-phosphonothioate diesters, Nucleosides, Nucleotides & Nucleic Acids, 22(5-8):1467-1469 (2003).
Nowotny, M. et al., Structure of human RNase H1 complexed with an RNA/DNA hybrid: insight into HIV reverse transcription, Mol Cell, 28(2):264-76 (2007).
Nukaga, Y. et al., Stereocontrolled Solid-Phase Synthesis of Phosphate/Phosphorothioate (PO/PS) Chimeric Oligodeoxyribonucleotides on an Automated Synthesizer Using an Oxazaphospholidine-Phosphoramidite Method, J. Org. Chem., A-J, 10 pages (Received: Dec. 13, 2015).
Nukaga, Y. et al., Stereocontrolled Solid-Phase Synthesis of Phosphorothioate Oligoribonucleotides Using 2'-O-(2-Cyanoethoxymethyl)-nucleoside 3'-O-Oxazaphospholiidine Monomers, Journal of Organic Chemistry, 77(18):7913-7922 (2012).
O'Connell, D. et al., Calcium-dependent oligonucleotide antagonists specific for L-selectin, Proc. Natl. Acad. Sci. USA, 93: 5883-5887 (1996).
Ohgi, T. et al., A New RNA Synthetic Method with a 2'-O-(2-Cyanoethoxymethyl) Protecting Group, Organic Letters, 7(16): 3477-3480 (2005).
Ohkubo et al., Synthesis of oligodeoxyribonucleotides containing hydroxymethylphosphonate bonds in the phosphoramidite method and their hybridization properties, Tetrahedron Letters, 46(51): 8953-8957 (2005).
Oka, N. and Wada, T., Stereocontrolled synthesis of oligonucleotide analogs containing chiral internucleotidic phosphorus atoms, Chemical Society Reviews, 40(12):5829-5843 (2011).
Oka, N. et al., An oxazaphospholidine approach for the stereocontrolled synthesis of oligonucleoside phosphorothioates, Journal of the America Chemical Society, 125(27):8307-8317 (2003).
Oka, N. et al., Diastereocontrolled Synthesis of Dinucleoside Phosphorothioates Using a Novel Class of Activators, Dialkyl(cyanomethyl)ammonium Tetrafluoroborates, Journal of the American Chemical Society, 124(18):4962-4963 (2002).
Oka, N. et al., Solid-Phase Synthesis of Stereoregular Oligodeoxyribonucleoside Phosphorothioates Using Bicyclic Oxazaphospholidine Derivatives as Monomer Units, Journal of the American Chemical Society, 130(47):16031-16037 (2008).
Oka, N. et al., Stereocontrolled synthesis of dinucleoside boranophosphates by an oxazaphospholidine method, Nucleic Acids Symposium Series, (49): 131-132 (2005).
Oka, N. et al., Stereocontrolled synthesis of oligonucleoside phosphorothioates and PO/PS-chimeric oligonucleotides by using oxazaphospholidine derivaties, Nucleic Acids Symposium Series, 52: 335-336 (2008).
Oka, N. et al., Stereocontrolled Synthesis of Oligoribonucleoside Phosphorothioates by an Oxazaphospholidine Approach, Organic Letters, 11(4):967-970 (2009).
Ostergaard, M. et al., Rational design of antisense oligonucleotides targeting single nucleotide polymorphisms for potent and allele selective suppression of mutant Huntingtin in the CNS, Nucleic Acids Research, 41(21), 9634-9650 (2013).
Otting, G. et al., Why Pentose- and Not Hexose-Nucleid Acids? Part IV. 'Homo-DNA': 1H-, 13C-, 31P-, and 15N-NMR-Spectroscopic Investigation of ddGlc(A-A-A-A-A-T-T-T-T-T) in Aqueous Solution, Helvetica Chimica Acta, 76(8):2701-2756 (1993).
Padmanabhan, S. et al., Anti-HBV nucleotide prodrug analogs: Synthesis, bioreversibility, and cytotoxicity studies, Bioorganic and Medicinal Chemistry Letters, 16(15):1491-1494 (2006).
Pan, Q-W. et al., New therapeutic opportunities for Hepatitis C based on small RNA, World J. Gastroenterol., 13(33): 4431-4436 (2007).
Parrish et al., Functional Anatomy of a dsRNA Trigger: Differential Requirement for the Two Trigger Strands in RNA Interference, Molecular Cell, 6:1077-1087 (2000).
Patil et al., Syntheses and properties of oligothymidylate analogs containing stereoregulated phosphorothioate and phosphodiester linkages in an alternating manner, Bioorganic & Medicinal Chemistry Letters, 4(22): 2663-2666 (1994).
Perrino, E. et al., New sulfurated derivatives of valproic acid with enhanced histone deacetylase inhibitory activity, Bioorganic & Medicinal Chemistry Letters, 18(6): 1893-1897 (2008).
Peyrottes, S. et al., SATE pronucleotide approaches: an overview, Mini-Reviews Medicinal Chemistry, 4(4):395-408 (2004).
Pfister, E.L. et al., Five siRNAs targeting three SNPs may provide therapy for three-quarters of Huntington's disease patients, 19(9): 774-778 (2009).
Pharmacology Review(s), Application No. 203568Orig1s000, Center for Drug Evaluation and Research, Food and Drug Administration, Department of Health & Human Services, 2013.
Pitsch, S. et al., Reliable Chemical Synthesis of Oligoribonucleotides (RNA) with 2'-O-[(Triisopropylsilypoxy]methyl(2'-O-tom)-Protected Phosphoramidites, Helvetica Chimica Acta, 84: 3773-3795 (2001).
Poijarvi, P. et al., 2,2-Bis(ethoxycarbonyl)- and 2-(Alkylaminocarbonyl)-2-cyano-Substituted 3-(Pivaloyloxy)propyl Groups as Biodegradable Phosphate Protections of Oligonucleotides, Bioconjugate Chemistry, 16(6):1564-1571 (2005).
Poijarvi, P. et al., The chemical stability of S-(2-acylthioethyl) and S-acyloxymethyl protected thymidylyl-3',5'-thymidine phosphoromonothiolates and their deacylation products in aqueous solution, Nucleosides Nucleotides and Nucleic Acids, 20(1-2):77-91 (2001).
Poijarvi, P. et al., Towards Nucleotide Prodrugs Derived from 2,2-Bis(hydroxymethyl)malonate and Its Congeners: Hydrolytic Cleavage of 2-Cyano-2-(hydroxymethyl)-3-methoxy-3-oxopropyl and 3-(Alkylamino)-2-cyano-2-(hydroxymethyl)-3-oxopropyl Protections from the Internucleosidic Phosphodiester and Phosphorothioate Linkages, Helvetica Chimica Acta, 85(7):1869-1876 (2002).
Poijarvi, P. et al., Towards Oligonucleotide Pro-Drugs: 2,2-Bis(ethoxycarbonyl) and 2-(Alkylaminocarbonyl)-2-cyano Substituted 3-(Pivaloyloxy)Propyl Groups as Biodegradable Protecting Groups for Internucleosidic Phosphoromonothioate Linkages, Letters in Organic Chemistry, 1(2):183-188 (2004).
Poijarvi, P., Prodrug Approaches of Nucleotides and Oligonucleotides, Current Medicinal Chemistry, 13(28):3441-3465 (2006).

(56) References Cited

OTHER PUBLICATIONS

Pon, R. T., Solid-Phase Supports for Oligonucleotide Synthesis, Current Protocols in Nucleic Acid Chemistry, 3.1.1-3.1.28 (2000).
Pontiggia, R. et al., 2-C-Methyluridine modified hammerhead riboxyme against the estrogen receptor, Bioorganic & Medicinal Chemistry Letters, 20: 2806-2808 (2010).
Pontiggia, R. et al., DNAzymes and ribozymes carrying 2'-C-methyl nucleotides, Nucleic Acids Sumposium Series, 52: 521-522 (2008).
Potter et al, Stereospecificity of nucleases towards phosphorothioate-substituted RNA: stereochemistry of transcription by T7 RNA polymerase, Nucleinc Acids Research, 15(10): 4145-4162 (1987).
Potter, B.V.L. et al., Synthesis and Configurational Analysis of Dinucleoside Phosphate Isotopically Chiral at Phosphorus. Stereochmical Course of Penicillium citrum Nuclease P1 Reaction, Biochemistry, 22: 1369-1377 (1983).
Prakash, T.P. et al., 2'-O-[2-(Methylthio )ethyl]-Modified Oligonucleotide: An Analogue of 2'O-[2-(Methoxy)-ethyl]-Modified Oligonucleotide with Improved Protein Binding Properties and High Binding Affinity to Target RNA, Biochemistry, 41: 11642-11648 (2002).
Prhavc, M. et al., 2'-O-[2-[2-(N,N-Dimethylamino)ethoxy]ethyl] Modified Oligonucleotides: Symbiosis of Charge Interaction Factors and Stereoelectronic Effects, Organic Letters, 5(12): 2017-2020 (2003).
Puri, N. et al, Targeted Gene Knockout by 2'-O-Aminoethyl Modified Triplex Forming Oligonucleotides, J. Biol. Chem., 276: 28991-28998 (2001).
Puri, N. et al., The Synthesis and Reactivity of New 2-(N,N-Diisoprophylamino)-3-Methylsulfonyl-1,3,2-Benzoxazaphospholes. The Utility of the 5-Chloro analogue in the One-Pot Synthesis of Oligothiophosphates: [ApsppA, ApspppA, ppp5'A2'ps5'A, m7GpsppA, Apspppp, Apspp], Tetrahedron 51(10): 2991-3014 (1995).
Ravikumar, V.T. et al., Unylinker: An Efficient and Scaleable Synthesis of Oligonucleotides Utilizing a Universal Linker Molecule: A Novel Approach to Enhance the Purity of Drugs, Org. Process Res. Dev., 12(3): 399-410 (2008).
Reese, C.B. and Yan, H., Solution phase synthesis of ISIS 2922 (Vitravene) by the modified H-phophane approach, J. Chem. Soc., Perkin Trans. I, 2619-2633 (2002).
Reither, S. and Jeltsch, A., Specificity of DNA triple helix formation analyzed by a FRET assay, BMC Biochemistry, 3: 9 pages (2002).
Revankar, G. R. and Rao, T.S., DNA with Altered Bases, DNA and Aspects of Molecular Biology, Comprehensive Natural Products Chemistry, 7.09: 313-339 (1999).
Robinson, D.S. et al., Predominant TH2-Like Bronchoalveolar T-Lymphocyte Population in Atopic Asthma, The New England Journal of Medicine, 326: 298-304 (1992).
Rozners, E. et al., Evaluation of 2'-hydroxyl protection in RNA-synthesis using the H-phosphonate approad, Nucleic Acids Research, 22(1): 94-99 (1994).
Sakatsume, O. et al., Solid Phase Synthesis of Oligoribonucleotides by the Phosphoramidite Approach Using 2'-O-1-(2-Chloroethoxy)Ethyl Protection, Tetrahedron, 47(41): 8717-8728 (1991).
Saneyoshi, H. et al., A General Method for the Synthesis of 2'-O-Cyanoethylated Oligoribonucleotides Having Promising Hybridization Affinity for DNA and RNA and Enhanced Nuclease Resistance, The Journal of Organic Chemistry, 70(25): 10453-10460 (2005).
Schoning, K.-U. et al., Chemical Etiology of Nucleic Acid Structure: The α-Threofuranosyl-(3'->2') Oligonucleotide System, Science, 290(5495):1347-1351 (2000).
Schultz, C., Prodrugs of Biologically Active Phospate Esters, Bioorganic and Medicinal Chemistry, 11(6):885-898 (2003).
Schulz, W.G. and Cai, S.L., Synthetic Genetics, Chemical and Engineering News, 5 (2012).
Seela et al, Diastereomerically pure Rp and Sp dinucleoside H-phosphonates. The stereochemical course of their conversion into P-methylphosphonates, phosphorothioates and [18O] chiral phosphates, Journal of Organic Chemistry, 56(12): 3861-3869 (1991).
Seidman, M.M. and Glazer, P.T. The potential for gene repair via triple helix formation, The Journal of Clinical Investigation, 112(4): 487-494 (2003).
Senn, J.J. et al., Non-CpG-Containing Antisense 2-Methoxyethyl Oligonucleotides Activate a Proinflammatory Response Independent of Toll-Like Receptor 9 or Myeloid DifferentiationFactor 88, The Journal of Pharmacology and Experimental Therapeutics, 314: 972-979 (2005).
Sergueeva et al., Synthesis of Dithymidine Boranophosphates via Stereospecific Boronation of H-phosphonate Diesters and Assignment of their Configuration, Tetrahedron Letters, 40: 2041-2044 (1999).
Seth, P.P. et al., An Exocyclic Methylene Group Acts as a Bioisostere of the 2'Oxygen Atom in LNA, J. Am. Chem. Soc, 132(42): 14942-14950 (2010).
Sharma, V.K. et al. Antisense oligonucleotides: modifications and clinical trials, Med. Chem. Commun., 5: 1454-71 (2014).
She, X. et al., Synergy between Anti-Endoglin (CD105) Monoclonal Antibodies and TGF-β in Suppression of Growth of Human Endothelial Cells, Int. J. Cancer, 108: 251-257 (2004).
Sheehan, J.P. and Phan, T.M. Phosphorothioate Oligonucleotides Inhibit the Intrinsic Tenase Complex by an Allosteric Mechanism, Biochemistry, 40: 4980-4989 (2001).
Sierzchala et al., Oxathiaphospholane Method of Stereocontrolled Synthesis of Diribonucleoside 3', 5'-Phosphorotioates, Journal of Organic Chemistry 61(19): 6713-6716 (1996).
Silverman, R.H., A scientific journey through the 2-5A/RNase L system, Cytokine Growth Factor Reviews, 18(5-6):381-388 (2007).
Singhrao, S.K. et al., Increased Complement Biosynthesis by Microglia and Complement Activation on Neurons in Huntington's Disease, Experimental Neurology, 159: 362-376 (1999).
Skotte, N.H. et al., Allele-specific suppression of mutant huntingtin using antisense oligonucleotides: providing a therapeutic option for all Huntington disease patients, PLoS One, 9(9): e107434 1-18 (2014).
Small, L.D. et al.,Comparison of Some Properties of Thiolsulfonates and Thiolsulfinates, Journal of the American Chemical Society, 71(10): 3565-3566 (1949).
Smith, A. et al., The murine haemopexin receptor, Biochem. J., 276: 417-425 (1991).
Sobkowski, et al. Stereochemistry of internucleotide bond formation by the H?phosphonate method. 1. Synthesis and 31P NMR analysis of 16 diribonulceoside (3'-5')-H-phosphonates and the corresponding phosphorothioates, Nucleosides Nucleotides Nucleic Acids, 24(10-12): 1469-84 (2005).
Sonveaux, E., Protecting Groups in Oligonucleotide Synthesis, Protocols for Oligonucleotide Conjugates, Methods in Molecular Biology, Edited by Agrawal, S., Humana Press, 26: 1-71 (1994).
Spinelli, N. et al., Use of Allylic Protecting Groups for the Synthesis of Base-Sensitive Prooligonucleotides, European Journal of Organic Chemistry, 49-56 (2002).
Sproat, B.S., RNA Synthesis Using 2'-O-(Tert-Butyldimethylsilyl) Protection, Methods in Molecular Biology, 288: 17-31 (2005).
Stawinski et al., Nucleoside H-phosphonates. 14. Synthesis of nucleoside phosphoroselenoates and phosphorothioselenoates via stereospecific selenization of the corresponding H-phosphonate and H-phosphonothioate diesters with the aid of new selenium-transfer reagent, 3H-1,2-benzothiaselenol-3-one, J. Org. Chem., 59(1): 130-136 (1994).
Stawinski et al., Stereospecific oxidation and oxidative coupling of H-phosphonate and H-phosphonothioate diesters, Tetrahedron Letters, 33(22):3185-3188 (1992).
Stawinski, J. and Stromberg, R. Di- and Oligonucleotide Synthesis Using H-Phosphonate Chemistry, Methods in Molecular Biology, 288: 81-100 (2005).
Stawinski, J. and Thelin, M., 3-H-2,1-benzoxathiol-3-one 1-oxide-A New Reagent for Stereospecific Oxidation of Nucleoside H-Phosphonothioate Diesters, Tetrahedron Letters, 33(22): 3189-3192 (1992).

(56) References Cited

OTHER PUBLICATIONS

Stawinski, J. and Thelin, M., 3H-1,2-benzothiaselenol-3-one. A new selenizing reagent for nucleoside H-phosphonate and H-phosphonothioate diesters, Tetrahedron Letters, 33(47): 7255-7258 (1992).

Stec et al., Deoxyribonucleoside 3'-O-(2-Thio- and 2-Oxo-"spiro"-4,4-pentamethylene-1,3,2-oxathiaphospholane)s:? Monomers for Stereocontrolled Synthesis of Oligo(deoxyribonucleoside phosphorothioate)s and Chimeric PS/PS Oligonucleotides, J. Am. Chem. Soc., 120(29): 7156-7167 (1998).

Stec et al., Oxathiaphospholane Method of Stereocontrolled Synthesis of Diribonucleoside 3', 5'-Phosphorothiptes, J. Org. Chem., 61(19): 6713-6716 (1996).

Stec et al., Stereocontrolled Synthesis of Oligo (nucleoside phosphorothioate)s , Angew. Chem. Int. Ed. Engl., 33:709-722 (1994).

Stec et al., Stereospecific Synthesis of P-Chiral Analogs of Oligonucleotides, Methods in Molecular Biology, 20: 285-313 (1993).

Stec, Oligo(nucleoside Phosphorothioate)s: The Quest of P-Chirality, in Phosphorus, Sulfur, and Silicon, 177(6): 1775-1778 (2002).

Stec, W.J. and Zon, G., Stereochemical Studies of the Formation of Chiral Internucleotide Linkages by Phosphormadite COupling in the Synthesis of Oligodeocyribonucleotides, Tetrahedron Letters, 25(46): 5279-5282 (1984).

Stec, W.J. et al., Automated Solid-Phase Synthesis, Separation, and Stereochemistry of Phosphorothioate Analogues of Oligodeocyribonucleotides, J. Am. Chem. Soc., 106: 6077-6079 (1984).

Stec, W.J. et al., Diastereomers of Nucleoside 3'-O-(2-Thio-1,3,2-oxathia(selena)phospholanes): Building Blocks for Stereocontrolled Synthesis of Oligo(nucleoside phosphorothioate)s, Journal of the American Chemical Society, 117(49):12019-12029 (1995).

Stec, W.J. et al., Novel route to oligo(deoxyribonucleoside phosphorothioates). Stereocontrolled synthesis of P-chiral oligo(deoxyribonucleoside phosphorothioates), Nucleic Acids Research, 19(21):5883-5888 (1991).

Stec, W.J. et al., Stereodependent inhibition of plasminogen activator inhibitor type 1 by phosphorothioate oligonucleotides: proof of sequence specificity in cell culture and in vivo rat experiments, Antisense Nucleic Acid Drug Dev., 7(6):567-73 (1997).

Stein, C.A. and Cheng, Y.C., Antisense oligonucleotides as therapeutic agents—is the bullet really magical?, Science, 261(5124):1004-12 (1993).

Sureshbabu, V.V. et al., Synthesis of tetrazole analogues of amino acids using Fmoc chemistry: isolation of amino free tetrazoles and their incorporation into peptides, Tetrahedron Letters, 48(39): 7038-7041 (2007).

Suska, A. et al., Antisense oligonucleotides: Stereocontrolled synthesis of phosphorothioate oligonucleotides, Pure and Applied Chemistry, 65(4):707-714 (1993).

Swayze, E.E. and Bhat, B., The medicinal chemistry of oligonucleotides, Crooke, S.T. (ed) Antisense Drug Technology: Principles, Strategies, and Applications, CRC Press, Boca Raton, FL: 143-82 (2007).

Swayze, E.E. et al., Antisense oligonucleotides containing locked nucleic acid improve potency but cause significant hepatotoxicity in animals, Nucleic Acids Research, 35(20: 687-700 (2007).

Takahashi, D. et al., Novel diphenylmethyl-Derived Amide Protecting Group for Efficient Liquid-Phase Peptide Synthesis: AJIPHASE, Org. Lett., 14(17): 4514-4517 (2012).

Takeno, H. et al., Selection of an RNA Molecule that Specifically Inhibits the Protease Activity of Subtilisin, J. Biochem., 125: 1115-1119 (1999).

Tamura et al., Preparation of Stereoregulated Antisense Oligodeoxyribonucleoside Phoshorothioate and Interaction with its Complementary DNA and RNA, Nucleosides & Nucleotides,17(1-3): 269-282 (1998).

Tang, J. et al., Enzymatic Synthesis of Stereoregular (All Rp) Oligonucleotide Phosphorothioate and Its Properties, Nucleosides Nucleotides, 14(3-5):985-990 (1995).

Tawarada, R. et al., Mechanistic studies on oxidative condensation of a thymidine 3'-H-phosphonate derivative with 3'-O-acetylthymidine, Archive for Organic Chemistry, (3):264-273 (2009).

Thayer, J.R. et al., Separation of oligonucleotide phosphorothioate distereoisomers by pellicular anion-exchange chromatography, Journal of Chromatography A, 1218: 802-808 (2011).

Tomoskozi et al., Stereospecific conversion of H-phosphonates into phosphoramidates. The use of vicinal carbon-phosphorus couplings for configurational determination of phosphorus, Tetrahedron, 51(24): 6797-6804 (1995).

Tosquellas, G. et al., First synthesis of alternating SATE-phosphotriester/phosphodiester prooligonucleotides on solid support, Bioorganic and Medicinal Chemistry Letters, 8(20): 2913-2918 (1998).

Tosquellas, G. et al., Prooligonucleotides exhibit less serum-protein binding than phosphodiester and phosphorothioate oligonucleotides, Nucleosides, Nucleotides and Nucleic Acids, 19(5-6):995-1003 (2000).

Tosquellas, G. et al., The pro-oligonucleotide approach: solid phase synthesis and preliminary evaluation of model pro-dodecathymidylates, Nucleic Acids Research, 26(9):2069-2074 (1998).

Tosquellas, G. et al., The Prooligonucleotide Approach III: Synthesis and bioreversibility of a chimeric phosphorodithioate prooligonucleotide, Bioorganic and Medicinal Chemistry Letters, 6(4):457-462 (1996).

Tosquellas, G. et al., The Prooligonucleotide Approach IV : Synthesis of chimeric prooligonucleotides with 6 enzymolabile masking groups and unexpected desulfurization side reaction, Bioorganic and Medicinal Chemistry Letters, 7(3):263-268 (1997).

Tsai, C.H. et al., Enzymatic synthesis of DNA on glycerol nucleic acid templates without stable duplex formation between product and template, Proceedings of the National Academy of Science, 104(37):14598-14603 (2007).

Tuerk, C. and Gold, L., Systematic Evolution of Ligans by Exponential Enrichment: RNA Ligands to Bacteriophage T4 DNA Polymerase, Science, 249: 505-510 (1990).

Turner, D.H. et al, Improved Parameters for Prediction of RNA Structure, Cold Spring Harbor Symposia on Quantitative Biology, LII: 123-133 (1987).

Turner, D.H. et al., Free Energy Increments for Hydrogen Bonds in Nucleic Acid Base Pairs, J. Am. Chem. Soc., 109: 3783-3785 (1987).

U.S. Food and Drug Administration, Development of New Stereoisomeric Drugs, 8 pages (May 1, 1992). URL: http://www.fda.gov/Drugs/GuidanceComplianceRegulatoryInformation/Guidances/ucm122883.htm [Retrieved Jun. 15, 2016].

Umemoto, T et al., Oligoribonucleotide Synthesis by the use of 1-(2-cyanoethoxy)ethyl (CEE) as a 2'-hydroxy protecting group, Tetrahedron Letters 45: 9529-9531 (2004).

Uphoff, K.W. et al., In vitro selection of aptamers: the death of pure reason, Curr. Opin. Struct. Biol., 6: 281-288 (1996).

Usman, N et al., Automated Chemical Synthesis of Long Oligoribonucleotides Using 2'-O-Silylated Ribonucleoside 3'-O-Phosphoramidites on a Controlled-Pore Glass Support, J. Am. Chem. Soc. 109(25): 7845-7854 (1987).

Uznanski, B. et al., Stereochemistry of base-catalyzed ring opening of 1,3,2-oxathiaphospholanes. Absolute configuration of 2-{N-[(Rc)-1-(.alpha.-naphthyl)ethyl]amino}-2-thiono-1,3,2-oxathiaphospholanes and O,S-dimethyl N-[(Rc)-1-(.alpha.-naphthyl)ethyl]phosphoramidothioates, Journal of the American Chemical Society, 114(26):10197-10202 (1992).

Van Der Veken, P. et al., Irreversible inhibition of dipeptidyl peptidase 8 by dipeptide-derived diaryl phosphonates, Journal of Medicinal Chemistry, 50(23): 5568-5570 (2007).

Vasquez, K.M. et al., Chromosomal mutations induced by triplex-forming oligonucleotides in mammalian cells, Nucl. Acids Res. 27(4): 1176-1181 (1999).

(56) References Cited

OTHER PUBLICATIONS

Verma, S. and Eckstein, F., Modified Oligonucleotides: Synthesis and Strategy for Users, Annu. Rev. Biochem., 67: 99-134 (1998).
Vermeulen, A. et al., Double-Stranded Regions Are Essential Design Components of Potent Inhibitors of RISC Function, RNA, 13: 723-730 (2007).
Vives, E. et al., Lipophilic pro-oligonucleotides are rapidly and efficiently internalized in HeLa cells, Nucleic Acids Research, 27(20):4071-4076 (1999).
Vlassov, V.V. et al., Transport of oligonucleotides across natural and model membranes, Biochimica et Biophysica Acta, 1197: 95-108 (1994).
Vu, H. and Hirschbein, B.L., Internucleotide Phosphite Sulfurization With Tetraethylthiuram Disulfide. Phosphorothioate Oligonucleotide Synthesis via Phosphoramidite Chemistry, Tetrahedron Letters, 32(26):3005-3008 (1991).
Vuyisich, M. and Beal, P.A., Regulation of the RNA-dependent protein kinase by triple helix formation, Nuc, Acids Res., 28(12): 2369-74 (2000).
Wada et al., Stereocontrolled Synthesis of Phosphorothioate RNA by the Oxazaphospholidine Approach, Nucleic Acids Symp. Ser., 48: 57-58 (2004).
Wada, T. et al., Chemical synthesis and properties of stereoregulated phosphorothioate RNAs, Nucleic Acids Symposium Series, 51:119-120 (2007).
Wada, T. et al., Stereocontrolled synthesis of phosphorothioate DNA by an oxazaphospholidine approach, Nucleic Acids Research Supplement, 3:109-110 (2003).
Wada, Takeshi, Chapter I Development of nucleic acid medicines, 3.3 Chemical synthesis of phosphorous atom-modified nucleic acids, CMC Publication., Fronteir of Development of Nucleic Acid Medicine: 67-75 (2009).
Wagner, C.R. et al., Pronucleotides: toward the in vivo delivery of antiviral and anticancer nucleotides, Medicinal Research Reviews, 20(6):417-451 (2000).
Walker, J.R. et al., Structure of the Ku heterodimer bound to DNA and its implications for double-strand break repair, Nature, 412: 607-614 (2001).
Wan et al., Synthesis of Second Generation Antisense Oligonucleotides Containing Chiral Phosphorothioate Linkages and Evaluation of their Biophysical Properties and Biological Activity, 10th Annual Meeting of the Oligonucleotide Therapeutics Society, abstract received by Applicant Oct. 7, 2014, poster setup prior to presentation (first known to Applicant late Oct. 12, 2014, PST), poster presentation Oct. 13, 2014.
Wan, W.B. et al., Synthesis, biophysical properties and biological activity of second generation antisense oligonucleoties containing chiral phosphorothioate linkages, Nucleic Acid Research, 27 pages, online advance access (2014).
Wang H, et al., Therapeutic gene silencing delivered by a chemically modified siRNA against mutant SOD 1 slows ALS progression, The Journal of Biological Chemistry, 283(23):15845-15852 (2008).
Wang, J.-C. et al., A stereoselective synthesis of dinucleotide phosphorothioate triesters through a chiral indol-oxazaphosphorine intermediate, Tetrahedron Letters, 38(5):705-708 (1997).
Warby, S.C. et al., CAG expansion in the Huntington disease gene is associated with a specific and targetable predisposing haplogroup, Am. J. Hum. Genet., 84(3): 351-366 (2009).
WaVe Life Sciences Poster, Therapeutic Implications of Controlling P-Chirality in Phosphorothioate Oligonucleotides, Tides, San Diego (May 3-6, 2014).
Weidner, J.P. et al., Alkyl and Aryl Thiolsulfonates, Journal of Medicinal Chemistry, 7(5): 671-673 (1964).
Weiser, T.G., et al., An estimation of the global volume of surgery: a modeling strategy based on available data, Lancet, 372(9633): 139-144 (2008).
Welz et al., 5-(Benzylmercapto)-1H-tetrazole as activator for 2'-O-TBDMS phosphoramidite building blocks in RNA synthesis, Tetrahedron Letters, 43: 795-797 (2002).
Wengel, J., Synthesis of 3'-C- and 4'-C-Branched Oligodeoxynucleotides and the Development of Locked Nucleic Acid (LNA), Ace. Chem. Res., 32: 301-310 (1999).
Widdison, W. C. et al., Semisynthetic Maytansine analogues for the targeted treatment of cancer, Journal of Medicinal Chemistry, 49(14): 4392-4408 (2006).
Wild, E. et al., Quantification of mutant huntingtin protein in cerebrospinal fluid from Huntington's disease patients, the Journal of Clinical Investigation, 125(5): 1979-1986 (2015).
Wilk, A. and Stec, W.J., Analysis of oligo(deoxynucleoside phosphorothioate)s and their diastereomeric composition, Nucleic Acids Research, 23(3):530-534 (1995).
Wilk, A. et al., Deoxyribonucleoside Cyclic N-Acylphosphoramidites as a New Class of Monomers for the Stereocontrolled Synthesis of Oligothymidylyl- and Oligodeoxycytidylyl-Phosphorothioates, Journal of the American Chemical Society, 122(10): 2149-2156 (2000).
Wong, Chui Ming, Synthesis of anisomycin. Part I. The stereospecific synthesis of N-benzoyl-2-(p-methoxybenzyl)-3-hydroxy-4-carboxamido pyrrolidine and the absolute configuration of anisomycin, Canadian journal of Chemistry 46: 1101-1104 (1968).
Wright, P. et al., Large scale synthesis of oligonucleotides via phosphoramidite nucleosides and a high-loaded polystyrene support, Tetrahedron Letters, 34(21):3373-3736 (1993).
Written Opinion for PCT/IB2009/007923, 8 pages (Sep. 6, 2010).
Written Opinion for PCT/IB2015/000395, 10 pages (Oct. 30, 2015).
Written Opinion for PCT/JP11/55018, 3 pages (Mar. 29, 2011).
Written Opinion for PCT/JP11/71559, 6 pages (Dec. 20, 2011).
Written Opinion for PCT/JP2010/065900, 5 pages (Sep. 15, 2010).
Written Opinion for PCT/JP2013/004303, 6 pages (Aug. 13, 2013).
Written Opinion for PCT/US2010/041068, 11 pages, (Sep. 1, 2010).
Written Opinion for PCT/US2011/064287, 14 pages (Apr. 12, 2012).
Written Opinion for PCT/US2012/046805, 9 pages (Sep. 19, 2012).
Written Opinion for PCT/US2013/050407, 12 pages (Jan. 9, 2014).
Wu, X. et al., Synthesis of 5'-C- and 2'-O-(Bromoalkyl)-Substituted Ribonucleoside Phosphoramidites for the Post-synthetic Functionalization of Oligonucleotides on Solid Support, Helvetica Chimica Acta, 83: 1127-1144 (2000).
Xiang, Y. et al., Effects of RNase L mutations associated with prostate cancer on apoptosis induced by 2',5'-oligoadenylates, Cancer Research, 63(20):6795-6801 (2003).
Xiong, H.Y. et al., The human splicing code reveals new insights into the genetic determinants of disease, Science, 347(6218): 144 (2015).
Xu, D. and Esko, J.D., Demystifying Heparan Sulfate-Protein Interactions, Annu. Rev. Biochem., 83: 129-157 (2014).
Xu, L. et al., Cyclic ADP-ribose analogues containing the methylenebisphosphonate linkage: effect of pyrophosphate modifications on Ca2+ release activity, J. Med. Chem., 48(12): 4177-4181 (2005).
Yamada, O. et al., Diastereoselective Synthesis of 3,4-Dimethoxy-7-morphinanone: A Potential Route to Morphine, Organic Letters, 2(18): 2785-2788 (2000).
Yamakage, S-i. et al., 1-(2-Chloroethoxy)Ethyl Group for the Protection of 2'-Hydroxyl Group in the Synthesis of Oligoribonucleotides, Tetrahedron Letters, 30(46): 6361-6364 (1989).
Yamamoto, S. et al., Unique Palindromic Sequences in Synthetic Oligonucleotides are Required to Induce INF and Augment INF-Mediated Natural Killer Activity, J. Immunol., 148(12): 4072-4076 (1992).
Yanai, H. et al., Suppression of immune responses by nonimmunogenic oligodeoxynucleotides with high affinity for high-mobility group box proteins (HMGBs), PNAS Early Edition, 1-6 (2011).
Yu, D. et al., Stereo-Enriched Phosphorothioate Oligodeoxynucleotides: Synthesis, Biophysical and Biological Properties, Bioorganic & Medicinal Chemitry, 8: 275-284 (2000).
Yu, R.Z. et al., Cross-species comparison of in vivo PK/PD relationships for second-generation antisense oligonucleotides targeting apolipoprotein B-100, Biochem. Pharmacol., 77: 910-919 (2009).

(56) References Cited

OTHER PUBLICATIONS

Yu, S. et al., A One-Pot Formal [4+2] Cycloaddition Approach to Substituted Piperidines, Indolizidines, and Quinolizidines. Total Synthesis of Indolizidine (-)-209I, Journal of Organic Chemicals, 70:7364-7370 (2005).

Zhang, L. et al., A simple glycol nucleic acid, Journal of the American Chemical Society,127(12):4174-4175 (2005).

Zhang, R.S. et al., Synthesis of two mirror image 4-helix junctions derived from glycerol nucleic acid, Journal of the American Chemical Society, 130(18):5846-5847 (2008).

Zhao, J. et al., Genome-wide Identification of Polycomb-Associated RNAs by RIP-seq, Molecular Cell, 40: 939-953 (2010).

Zlatev et al., Phosphoramidate dinucleosides as hepatitis C virus polymerase inhibitors, J Med Chem., 51(18): 5745-57 (2008).

Zon, Automated synthesis of phosphorus-sulfur analogs of nucleic acids—25 years on: potential therapeutic agents and proven utility in biotechnology, New J. Chem., 34(5): 795-804 (2010).

Zon, G and Stec, W.J., Phosphorothioate oligonucleotides, Oligonucleotides and Analogues: A Practical Approach, 87-108 (1991).

Aartsma-Rus, A. et al., Targeted exon skipping as a potential gene correction therapy for Duchenne muscular dystrophy, Neuromuscular Disorders, 12: S71-S77 (2002).

Bartz, H. et al., Poly-guanosine strings improve cellular uptake and stimulatory activity of phosphodiester CpG oligonucleotides in human leukocytes, Vaccine, 23: 148-155 (2004).

Block, S.S. and Weidner, J.P, Vibrational Behavior and Structure of Disulfide Dioxides (Thiolsulfonates), Applied spectroscopy, 20(2): 71-73 (1966).

Cankurtaran, E.S. et al., Clinical Experience with Risperidone and Memantine in the Treatment of Huntington's Disease, Journal of the National Medical Association, 98(8): 1353-1355 (2006).

Chang, W. et al., Systematic chemical modifications of single stranded siRNAs significantly improved CTNNB1 mRNA silencing, Bioorg. Med. Chem. Lett., 1-5 (2016), http://dx.doi.org/10.1016/j.bmcl.2016.07.064.

Documents submitted to and/or received from the United States Securities and Exchange Commission; downloaded from EDGAR (Dec. 17, 2015-Oct. 4, 2016).

Gould, W.A. et al., Pyrrolidines IX. 3-Aryl-3-pyrrolidinols, Journal of Medicinal Chemistry, 7(1): 60-67 (1964).

Guerciolini, R., Allele-selective Silencing of Mutant Huntingtin by Stereopure Oligonucleotides, Wave Life Sciences, Huntington's Disease Society of America, HDSA Presentation 2016 (Jun. 3, 2016).

International Search Report for PCT/JP15/50716 and English Translation, 8 pages (Apr. 21, 2015).

International Search Report for PCT/JP2015/050714, and English Translation, 8 pages (Apr. 21, 2015).

International Search Report for PCT/JP2015/050718 and English Translation, 8 pages (Apr. 21, 2015).

International Search Report for PCT/US2016/043598, 4 pages (Nov. 28, 2016).

Iwamoto, N. et al., Optimization of Therapeutic Phosphorothioate Oligonucleotides by P-Chirality Control, Wave Life Sciences, PSJ Congress: The Pharmaceutical Society of Japan, (Mar. 25, 2015-Mar. 28, 2016).

Kaur, H. et al., Activation of natural killer-like YT-INDY cells by oligodeoxynucleotides and binding by homologous pattern recognition proteins, Scandinavian Journal of Immunology, 62: 361-370 (2005).

Kay, C. et al., Huntingtin Haplotypes Provide Prioritized Target Panels for Allele-specific Silencing in Huntington Disease Patients of European Ancestry, the American Society of Gene & Cell Therapy, 1-13 (2015).

Kim, M., Beta conformation of polyglutamine track revealed by a crystal structure of Huntingtin N-terminal region with insertion of three histidine residues, Prion, 7(3): 221-228 (2013).

Kremer, B. et al., A Worldwide Study of the Huntington's Disease Mutation, the New England Journal of Medicine, 330(20): 1401-1406 (1994).

Krieg, A.M., Development of TLR9 agonists for cancer therapy, the Journal of Clinical Investigation, 117(5): 1184-1194 (2007).

Kuramoto, Y. et al., Mannosylated cationic liposomes/CpG DNA complex for the treatment of hepatic metastasis after intravenous administration in mice, Journal of Pharmaceutical Science, 98(3): 1193-1197 (2009).

Meena, Control of Human RNase H Mediated Cleavage by Stereopure Phosphorothioate Oligonucleotides, Wave Life Sciences, Tides Meeting (May 3-6, 2015).

Meena, Development of Allele Specific Antisense Oligonucleotides, Wave Life Sciences, ACS Central Regional Meeting (CERM), Covington, KY (May 19, 2016).

Meena, Development of Allele Specific Antisense Oligonucleotides, Wave Life Sciences, Tides Meeting (May 11, 2016).

Meena, et al., Therapeutic Implications of Controlling P-Chirality in Phosphorothioate Oligonucleotides, Tides Poster (May 12-15, 2014).

Meena, Optimization of Antisense Drugs by P-Stereochemistry Control, Wave Life Sciences, OTS Annual Meeting 2014, Oligonucleotide Therapeutics Society (Oct. 12-14, 2014).

Monteys, A.M. et al., Artificial miRNAs Targeting Mutant Huntingtin Show Preferential Silencing in Vitro and in Vivo, Molecular THerapy—Nucleic Acids, 4: e234 1-11 (2015).

Pérez, B. et al., Antisense Mediated Splicing Modulation for Inherited Metabolic Diseases: Challenges for Delivery, Nucleic Acid Therapies, 24(1): 48-56 (2014).

Regan, J.F. et al., A Rapid Molecular Approach for Chromosomal Phasing, PLOS One, 1-15 (2015).

Rossetti, G., Structural aspects of the Huntingtin protein investigated by biocomputing methods, Thesis, RWTH Aachen University, Forschungszentrum Juelich, 173 pages (2011).

Schmitz, C. et al., Synthesis of P-Stereogenic Phosphoramidite and Phosphorodiamidite Ligands and Their Application in Asymmetric Catalysis, Eur. J. Org. Chem., 6205-6230 (2015).

Scrimgeour, E.M. Huntington Disease (Chorea) in the Middle East, SQU. Med. J., 9(1): 16-23 (2009).

Wave Life Sciences Press Release, Wave Life Sciences Added to the Russell 2000® Index, 2 pages (Jun. 27, 2016).

Wave Life Sciences Press Release, Wave Life Sciences Announces Plan to Deliver Six Clinical Programs by 2018, 6 pages (Jan. 29, 2016).

Wave Life Sciences Press Release, Wave Life Sciences Announces Pricing of Initial Public Offering, 3 pages (Nov. 11, 2015).

Wave Life Sciences Press Release, Wave Life Sciences Appoints Dr. Michael Panzara as Head of Neurology Franchise, 4 pages (Jul. 12, 2016).

Wave Life Sciences Press Release, Wave Life Sciences Appoints Keith Regnante as Chief Financial Officer, 4 pages (Aug. 17, 2016).

Wave Life Sciences Press Release, Wave Life Sciences Appoints Roberto Guerciolini, M. Senior Vice President and Head of Early Development, 2 pages (Apr. 7, 2015).

Wave Life Sciences Press Release, Wave Life Sciences Closed $18 Million Series a Financing to Advance Stereopure Nucleic Acid Therapeutics, 3 pages (Feb. 2, 2015).

Wave Life Sciences Press Release, Wave Life Sciences Enters Collaboration with Pfizer to Develop Genetically Targeted Therapies for the Treatment of Metabolic Diseases, 5 pages (May 5, 2016).

Wave Life Sciences Press Release, Wave Life Sciences Expands Stereopure Synthetic Chemistry Platform Capabilities, Augments Patent Portfolio with Addition of Single-Stranded RNAi (ssRNAi), 3 pages (Jun. 8, 2015).

Wave Life Sciences Press Release, Wave Life Sciences Raises $66 Million in Series B Financing, 3 pages (Aug. 18, 2015).

Wave Life Sciences Press Release, Wave Life Sciences Receives Orphan Drug Designation from FDA for its Lead Candidate Designed to Treat Huntington's Disease, 5 pages (Jun. 21, 2016).

Wave Life Sciences Press Release, Wave Life Sciences Reports First Quarter 2016 Financial Results and Provides Business Update, 9 pages (May 16, 2016).

Wave Life Sciences Press Release, Wave Life Sciences Reports Fourth Quarter and Full Year 2015 Financial Results and Provides Business Update, 10 pages (Mar. 30, 2016).

(56) References Cited

OTHER PUBLICATIONS

Wave Life Sciences Press Release, Wave Life Sciences Reports Second Quarter 2016 Financial Results and Provides Business Update, 10 pages (Aug. 15, 2016).
Wave Life Sciences Press Release, Wave Life Sciences to Advance Next-Generation Nucleic Acid Therapies to Address Unmet Need in Duchenne Muscular Dystrophy, 6 pages (May 9, 2016).
Wave Life Sciences Press Release, Wave Life Sciences to Present at the Deutsche Bank 41st Annual Health Care Conference, 2 pages (Apr. 29, 2016).
Wave Life Sciences Press Release, Wave Life Sciences to Present at the Jefferies 2016 Healthcare Conference, 2 pages (Jun. 1, 2016).
Wave Life Sciences Press Release, Wave Life Sciences to Present at the JMP Securities Life Sciences Conference, 2 pages (Jun. 15, 2016).
Wave Life Sciences Press Release, Wave Life Sciences to Present at the Leerink Partner 5th Annual Global Healthcare Conference, 2 pages (Feb. 3, 2016).
Wave Life Sciences Press Release, Wave Life Sciences to Present at the Leerink Partners Rare Disease & Immuno-Oncology Roundtable, 2 pages (Sep. 14, 2016).
Wave Life Sciences Press Release, Wave Life Sciences to Present at the SunTrust Robinson Humphrey 2016 Orphan Drug Day Conference, 2 pages (Feb. 16, 2016).
Written Opinion for PCT/JP15/50716 and English Translation, 11 pages (Apr. 21, 2015).
Written Opinion for PCT/JP2015/050714, and English Translation, 11 pages (Apr. 21, 2015).
Written Opinion for PCT/JP2015/050718 and English Translation, 6 pages ( Apr. 21, 2015).
Written Opinion for PCT/US2016/043598, 10 pages (Nov. 28, 2016).
Yamato, K. et al., Enhanced specificity of HPV16 E6E7 siRNA by RNA-DNA chimera modification, Cancer Gene Therapy, 18: 587-597 (2011).
Yu, D. et al., Accessible 5'-end of CpGcontaining phosphorothioate oligodeoxynucleotides is essential for immunostimulatory activity, Bioorganic & Medicinal Chemistry Letters, 10: 2585-2588 (2000).
Yu, D. et al., Single-Stranded RNAs Use RNAi to Potently and Allele-Selectively Inhibit Mutant Huntingtin Expression, Cell, 150: 895-908 (2012).
Zhang, J. et al., Optimization of Exon Skipping Therapies for Duchenne Muscular Dystrophy, Wave Life Sciences, PPMD: Parent Project Muscular Dystrophy Meeting, Orlando, FL (Jul. 25, 2016).

\* cited by examiner

Fig.1

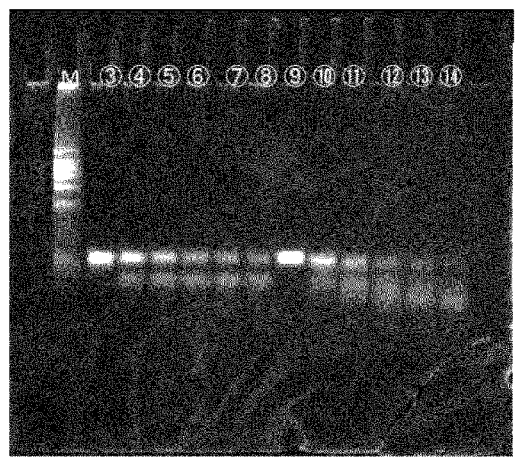

20% polyacrylamide gel,
constant current → constant voltage
M: Size marker
③ CG-0221 Sp 0 min(100.5 ng/lane)
④ CG-0221 Sp 60 min
⑤ CG-0221 Sp 120 min
⑥ CG-0221 Sp 180 min
⑦ CG-0221 Sp 240 min
⑧ CG-0221 Sp 300 min
⑨ CG-0221 Rp 0 min
⑩ CG-0221 Rp 60 min
⑪ CG-0221 Rp 120 min
⑫ CG-0221 Rp 180 min
⑬ CG-0221 Rp 240 min
⑭ CG-0221 Rp 300 min

Fig.2

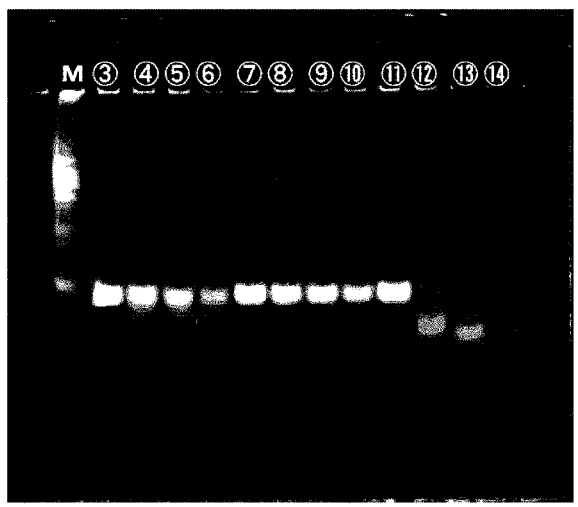

Constant current 20 mA,
120 min, 50% serum
M: Size marker
③ CG-0411 Mix 0 min
④ CG-0411 Mix 180 min
⑤ CG-0411 Mix 360 min
⑥ CG-0411 Mix O/N
⑦ CG-0411 Sp 0 min
⑧ CG-0411 Sp 180 min
⑨ CG-0411 Sp 360 min
⑩ CG-0411 Sp O/N
⑪ CG-0411 Rp 0 min
⑫ CG-0411 Rp 180 min
⑬ CG-0411 Rp 360 min
⑭ CG-0411 Rp O/N Constant current 20 mA, 120 min, 50% serum
M: Size marker
③ CG-0226 Mix 180 min
④ CG-0226 Mix 360 min
⑤ CG-0226 Mix O/N
⑥ CG-0226 Sp 0 min
⑦ CG-0226 Sp 180 min
⑧ CG-0226 Sp 360 min
⑨ CG-0226 Sp O/N
⑩ CG-0226 Rp 0 min
⑪ CG-0226 Rp 180 min
⑫ CG-0226 Rp 360 min
⑬ CG-0226 Rp O/N
⑭ CG-0226 Mix 0 min

CHIRAL NUCLEIC ACID ADJUVANT

FIELD OF THE INVENTION

This invention is directed to CpG oligonucleotides and a method of using it. In more detail, this invention is directed to cure of diseases that are caused by immune cell which is controlled by activation of dendritic cell using stereoisomer of CpG oligonucleotides and their stereoisomer.

BACKGROUND OF THE INVENTION

JP 2002-513763 A (Patent Literature 1), JP 2002-154397 A (Patent Literature 2), JP 2002-521489 A (Patent Literature 3) disclose CpG oligonucleotide and the method of manufacturing them.

JP 2010-504750 A (Patent Literature 4) discloses that oligonucleotides, which have lipophilic substituted nucleotide analogues out of CpG motif, cause production of interferon-α (IFN-α).

Following Non Patent Literature 1 discloses that the S-form stereoisomer of CpG oligonucleotide trimer promotes MAPK signal. All of the disclosures of this reference are incorporated herein by reference.

Following Non Patent Literature 1 discloses PF-3512676 (Sequence No. 128), all parts of the sequence are phosphorothioated and S-form stereoisomer. Natural oligonucleic acid is readily reduced in vivo. Whereas, that are changed phosphoric acid ester bond of oligo nucleic acid (P—O bond) to phosphoric acid thioester bond (P—S bond), P—S modifications are difficult to be reduced in vivo.

CITATION LIST

Patent Literature

[Patent Literature 1] JP 2002-513763 A
[Patent Literature 2] JP 2002-154397 A
[Patent Literature 3] JP 2002-521489 A
[Patent Literature 4] JP 2010-504750 A

Non Patent Literature

[Non Patent Literature 1] Authur M. Krieg et al. OLIGONUCLROTIDES 13: pp. 491-499 (2003)
[Non Patent Literature 2] Clin Cancer Res. 2008 Jul. 15; 14(14):4532-42.

SUMMARY OF INVENTION

Technical Problem

For example, all of the sequence of the CpG oligonucleotide disclosed in Non Patent Literature 2 are phosphorothioated. Therefore CpG oligonucleotides disclosed in Non Patent Literature 2 have problems that they induce inflammation and toxic reaction. When the phosphorothioate backbone modification is removed from the CpG oligonucleotides disclosed in Non Patent Literature 2, the stability of the nucleotide decreases.

One object of the present invention is to provide a stable stereoisomer of CpG oligonucleotide.

Other object of the present invention is to provide a stereoisomer of CpG oligonucleotides with interferon α (IFN-α) producing ability.

Other object of the present invention is to provide a cure for a specific disease by activation of dendritic cells with CpG oligonucleotide.

Other object of the present invention is to provide a stereoisomer of CpG oligonucleotides less cytotoxic.

Means for Achieving the Object

This invention is basically based on the following new finding. It is possible to enhance in-vivo stability of the oligo nucleic acid by controlling the molecular conformation of the oligo nucleic acid. Because of it, it becomes possible to provide a stable oligonucleotide in vivo, without introducing the PS bond to all of the sequences. Because not all of the sequences have PS binding modification, the oligonucleotide of the present invention has excellent biocompatibility.

At least one of the above objects is solved by the following invention. That is, the first aspect of the invention relates to an oligonucleotide which contains two to four sequences each represented by the formula 5'-$X_1X_2$CpG$X_3X_4$-3' (formula (I)) and has a length of 14 to 32 nucleotides.

In the formula (I), CpG represents unmethylated CpG without phosphate backbone modifications.

$X_1X_2$ is either AA, AT, GA or GT which may have phosphate backbone modification. The AA, AT, GA or GT which may have phosphate backbone modification means that it may have 1 or 2 phosphate backbone modifications in either of AA, AT, GA or GT. Same as above.

$X_3X_4$ is TT, AT, AC, TA, is a TC or CG that may have phosphate backbone modification.

The oligonucleotide may have phosphate backbone modification at a site other than 5'-$X_1X_2$CpG$X_3X_4$-3'. That is, the oligonucleotide may have a phosphate backbone modification on the section other than one of CpG motif consisting of 5'-$X_1X_2$CpG$X_3X_4$-3'. However, oligonucleotide having at least one phosphate backbone modification on the section other than one of CpG motifs is preferred.

This oligonucleotide is preferred to be that $X_1X_2$ is AT, GT or GA which may have phosphate backbone modification and $X_3X_4$, is TT, AT, AC, TA, CG or TC which may have phosphate backbone modification.

This oligonucleotide is preferred to be that $X_1X_2$, is either AA, AT, GA or GT without phosphate backbone modifications and $X_3X_4$ is, TT, AT, AC, TC or CG without phosphate backbone modifications are preferred.

The site having least one of the phosphate backbone modification sites other than 5'-$X_1X_2$CpG$X_3X_4$-3' is preferred to be S-form stereoisomer.

The oligonucleotide of this invention is preferred to include any of the following sequences or be an oligonucleotide consisting of any of the following sequences.

| SEQ No. | Sequence |
|---|---|
| [Formula 1] | |
| 1 | T*C*GTCGTT*T*T*GTCGTT*T*T*GTCGGG |
| 2 | G*G*GTCGTT*T*T*GTCGTT*T*T*GTCGGG |
| 3 | T*C*AACGTT*T*C*AACGTT*T*T |
| 4 | T*C*AACGTT*T*C*AACGTT*T*T*GG |
| 5 | T*C*AACGTT*T*C*AACGTT*G*G |

| SEQ No. | Sequence |
|---|---|
| 6 | T*C*AACGTT*T*C*AACGTT*G*G*G*G |
| 7 | T*C*AACGTT*T*T*AACGTT*T*T*AACGGG |
| 8 | T*C*AACGTT*T*A*ACGTT*T*T |
| 9 | T*C*AACGT*TAACGTT*T*T |
| 10 | T*C*AACGTT*T*A*AACGTT*T*A*AACGGG |
| 11 | T*C*AACGTTAACGTTAACGGG |
| 12 | T*C*GACGTT*T*T*GACGTT*T*T*GACGGG |
| 15 | G*G*GACGT*T*T*TGACGT*T*T*TGACGGGGG |
| 16 | T*C*GACGT*T*T*TGACGT*T*T*TGACGT*T*T*TGACGGG |
| 17 | T*C*GACGT*T*GACGT*T*GACGGG |
| 20 | T*C*GACGT*T*GACGT*T*GACGT*T*GACGGG |
| 21 | T*C*GACGTT*T*A*AACGTT*T*A*AACGTT*T*A*AACGGG |
| 22 | T*C*GACGTT*T*A*AACGTT*T*A*GACGTT*T*A*AACGGG |
| 23 | T*C*GACGTTAACGTTAACGTTAACGGG |

[Formula 2]

| SEQ No. | Sequence |
|---|---|
| 24 | GGGACGTT*T*A*AACGTCTAGACGGG |
| 25 | T*C*GACGT*ACGT*ACGT*ACGGG |
| 26 | T*C*GACGTT*T*T*GACGTT*T*T*G*A*C*G*G |
| 29 | T*C*GACGTT*T*T*GACGTT*T*T*GACGG*G*G |
| 30 | T*C*GACGTT*T*T*GACGTT*T*T*GACGT*G*G |
| 31 | T*C*GACGTT*T*T*GACGTT*T*T*GACGTG*G*G |
| 32 | T*C*GACGTT*T*T*GACGTT*T*T*G*A*C*G*G*G |
| 33 | T*C*GACGTT*T*T*GACGTT*T*T*GACGG*G*G*G |
| 36 | T*C*GACGTT*T*T*GACGTT*T*T*GACG*G*G*G*G |
| 37 | T*C*GACGT*T*GACGT*T*GACGTG*G*G |
| 38 | G*G*T*G*C*ATCGAT*G*C*A*G*G*G*G*G |
| 39 | T*C*ATCGAT*T*T*ATCGAT*T*T*ATCGGG |
| 40 | G*G*T*G*C*GACGAT*G*C*A*G*G*G*G*G*G |
| 41 | G*G*G*G*GACGATCGTCGGG*G*G*G |
| 42 | G*G*GACGATATCGTCG*G*G*G*G*G |
| 43 | G*G*GACGACGTCGTCG*G*G*G*G*G |
| 46 | G*G*GGGACGATCGTCG*G*G*G*G*G |
| 47 | G*G*GACGCGCGTCG*G*G*G*G*G*G |
| 48 | G*G*G*G*TCGTTCG*G*G*G |

[Formula 3]

| SEQ No. | Sequence |
|---|---|
| 49 | T*C*ATCGAT*T*T*ATCGAT*T*T*A*A*C*G*G |
| 50 | T*C*GACGTTTTGACGTT*T*T*G*A*C*G*G |
| 51 | T*C*GACGTTTTGACGTTTT*G*A*C*G*G |
| 52 | T*C*GACGT*T*GACGT*T*GACGG*G |
| 53 | TC*GACGT*T*GACGT*T*GACG*G*G |
| 54 | T*C*GACGT*T*GACGT*T*GACGG*G*G |
| 55 | T*C*GACGT*T*GACGT*T*GACT*G |
| 56 | T*C*GACGT*T*GACGT*T*G*A*C*G*G*G |
| 57 | T*C*GACGTTGACGT*T*G*A*C*G*G*G |
| 58 | T*C*ATCGATATCGA*T*G*A*C*G*G*G |
| 59 | T*C*GACGT*T*GACGT*T*GACG*G*G*G |
| 60 | T*C*GACGTT*T*T*GACGTT*T*T*G*G*G*G*G |
| 61 | T*C*GACGTT*T*T*GACGTT*T*T*G*A*G*G*G*G |
| 62 | T*C*GACGTT*T*T*GACGTT*T*T*G*T*G*G*G*G |
| 63 | T*C*G*ACGTT*G*ACGTT*G*A*C*G*G*G |
| 64 | C*C*GACGTT*T*T*GACGTT*T*T*GACG*G*G |
| 65 | T*C*GACGTT*T*A*GACGTT*T*A*GACG*G*G |
| 66 | T*C*GACGTT*T*T*GACGTT*T*T*GACG*A*A |
| 67 | T*C*GACGTT*T*T*GACGTT*T*T*GACG*T*T |
| 68 | T*C*AACGTT*T*T*AACGTT*T*T*GACG*G*G |
| 69 | T*C*GACGTT*T*T*GACGTT*T*T*GGG |
| 70 | T*C*GACGTT*T*T*GACGTT*T*T*GACGTTGG |
| 71 | T*C*GACGTT*GACGTT*G*G*G |
| 72 | T*C*GACGTT*T*T*T*ACGTT*T*T*G*ACG*G*G |
| 73 | T*C*G*A*CGTT*T*T*ACGTTTGACGGG |
| 74 | T*C*G*ACGTT*T*T*G*ACGTT*T*T*G*ACG*G*G |
| 75 | T*C*GACGTA*GACGTA*GACG*G*G |
| 76 | T*A*GACGAT*T*C*GTCGTC*T*A*GACG*G*G |
| 77 | T*A*GACGA*C*GTCGT*A*GACC*G*G |
| 78 | T*C*G*ACGTTT*T*G*ACGTT*T*T*G*A*C*G*G*G |
| 79 | T*C*G*ACGTT*T*T*T*A*ACGAC*T*T*G*A*C*G*G*G |

[Formula 4]

| SEQ No. | Sequence |
|---|---|
| 80 | T*C*G*ACGTTT*T*AACGAC*T*T*G*A*C*G*G*G |
| 81 | T*C*ATCGAT*T*T*ATCGAT*T*T*GACG*G*G |
| 82 | T*C*ATCGAT*T*T*ATCGAT*T*T*ATCGA*T*G*G*G |
| 83 | T*C*ATCGAT*T*T*ATCGAT*T*T*AT*C*G*G*G |
| 84 | T*C*ATCGAT*T*T*ATCGAT*T*T*ATCGAT*T*T*ATCG*G*G |
| 85 | T*C*ATCGAT*T*T*ATCGAT*T*T*ATCGAT*T*T*A*T*C*G*G*G |
| 86 | T*C*ATCGAT*T*T*ATCGAT*T*T*ATCGAT*A*T*C*G*G*G |
| 87 | T*T*ATCGAT*T*T*ATCGAT*T*T*G*A*C*G*G*G |
| 88 | T*C*ATCGATATCGAT*T*T*G*A*C*G*G*G |
| 89 | TCATCGAT*T*T*ATCGAT*T*T*A*T*C*G*G*G |

-continued

| SEQ No. | Sequence |
|---|---|
| 90 | T*C*ATCGAT*T*T*ATCGAT*T*T*G*A*C*G*A*T |
| 91 | T*C*GACGT*T*GACGT*T*GACGT*T*G*G*G |
| 92 | T*C*G*ACGT*T*G*ACGT*T*G*A*C*G*G*G |
| 93 | T*C*A*TCGAT*T*T*A*TCGAT*T*T*G*A*C*G*G |
| 94 | T*C*A*TCGAT*A*TCGAT*G*ACGT*T*T*G*G*G |
| 95 | T*C*GACGTTTGACGTTT*G*A*C*G*G*G |
| 96 | T*C*ATCGAT*T*T*ATCGAT*T*T*A*T*C*G*G*G |
| 97 | G*G*GACGATATCGTCG*G*G*G*G*G |
| 98 | G*G*GACGAC*G*TCGTCG*G*G*G*G*G |
| 99 | G*G*GACGACGTCGTCG*G*G*G*G*G |
| 100 | T*C*GACGACGTCGTCG*G*G*G*G*G |
| 101 | T*C*GACGACGTCGTCT*T*T*G*G*G |
| 102 | T*A*GACGACGTCGTCT*T*T*G*G*G |
| 103 | T*T*GACGACGTCGTCA*A*A*G*G*G |
| 104 | T*C*GACGTAGACGTCT*T*T*G*G*G |
| 105 | T*C*GACGTAGACGTTT*A*G*G*G*G |
| 106 | T*C*ATCGATATCGATT*T*T*G*G*G |
| 107 | T*T*ATCGATATCGATA*A*A*G*G*G |
| 108 | T*C*GACGTAGACGATCGA*T*G*G*G |
| 109 | T*C*GACGAC*T*T*GACGAC*T*T*G*A*C*G*G*G |
| 110 | T*C*GACGAC*T*T*GTCGTC*T*T*G*A*C*G*G*G |
| 111 | T*T*ATCGATATCGATA*T*C*G*A*T*G*G*G |
| 112 | T*T*ATCGATATCGATT*T*A*A*G*G*G |
| 113 | T*C*ATCGAT*T*T*ATCGAT*T*T*G*A*C*G*T*T |
| 114 | T*C*ATCGA*T*ATCGA*T*G*A*C*G*G*G*G |
| 115 | T*C*ATCGAT*ATCGA*T*G*G*G |
| 116 | T*C*GTCGTTGTCGT*T*G*A*C*G*G*G |
| 117 | T*C*G*TCGTT*T*T*G*TCGTT*T*T*G*A*C*G*G*G |
| 118 | T*C*GTCGTTGTCGTTG*A*C*G*A*C*G*G*G |

In above formula * indicates the stereoisomer caused by phosphate backbone modification, at least one of the * is S-form stereoisomer. CG of the section corresponding to 5'-$X_1X_2$CpG$X_3X_4$-3 in above formula means unmethylated CpG without phosphate backbone modifications.

The oligonucleotide of this invention is preferred to be that $X_1X_2$ is GA, and $X_3X_4$ is TT or AC.

The oligonucleotide of this invention is preferred to be that at least one of the phosphate backbone modifications of sites other than 5'-$X_1X_2$CpG$X_3X_4$-3' is an oligonucleotide having phosphorothioate.

The sequence consisting of 5'-$X_1X_2$CpG$X_3X_4$-3' of formula (I) is defined as CpG motif. The oligonucleotides of this invention is preferred to have a sequence of -(G)$_m$- (m is 2 to 10 integer) by 5' end or 3' end of CpG motif.

The oligonucleotide of this invention is preferred to have a sequence of -(G)$_m$- (m is 1 to 6 integer) by 5' end or 3' end of CpG motif.

The oligonucleotide of this invention is preferred to have a sequence of TC, TA, TG or CC at the point which is close to 5' end from the CpG motif.

The oligonucleotide of this invention is preferred to include at least the first CpG motif and the second CpG motif. The first CpG motif and the second CpG motif are bonded directly or the first CpG motif and the second CpG motif include a partial sequence that are represented as -(T)$_n$- (n is an integer of 1 to 3), TA or TC between the first CpG motif and the second CpG motif.

The oligonucleotide consists of either one of following sequences or sequences in which 1, 2, or 3 bases are substituted, inserted, deleted, or added:

(SEQ No. 13)
t$^{sp}$c$^{sp}$gacgtt$^{sp}$t$^{sp}$t$^{sp}$gacgtt$^{sp}$t$^{sp}$t$^{sp}$gacggg;

(SEQ No. 18)
t$^{sp}$c$^{sp}$gacgt$^{sp}$t$^{sp}$gacgt$^{sp}$t$^{sp}$gacggg;
and (SEQ No. 44)
g$^{sp}$g$^{sp}$gacgacgtcgtcg$^{sp}$g$^{sp}$g$^{sp}$g$^{sp}$g$^{sp}$g, in the sequences "cg" indicates non-methylated CpG with modification of phosphate backbone and "$^{sp}$" indicates that S form modification of phosphate backbone is added between neighbouring nucleotides.

These oligonucleotide are preferred to show same stability or activity as Sequence Nos. 13, 18 or 44. In the sequence, the "cg" indicates unmethylated CpG with a phosphate backbone modification.

The oligonucleotide of this invention is preferred to be (Sequence No. 13)
t$^{sp}$c$^{sp}$gacgtt$^{sp}$t$^{sp}$t$^{sp}$gacgtt$^{sp}$t$^{sp}$t$^{sp}$gacggg, (Sequence No. 18)
t$^{sp}$c$^{sp}$gacgt$^{sp}$t$^{sp}$gacgt$^{sp}$t$^{sp}$gacggg
or (Sequence No. 44)
g$^{sp}$g$^{sp}$gacgacgtcgtcg$^{sp}$g$^{sp}$g$^{sp}$g$^{sp}$g$^{sp}$g.

In the sequence, "cg" indicates unmethylated CpG with a phosphate backbone modification.

This invention also provides a composition that comprises the oligonucleotides described above.

This invention also provides a vaccine adjuvant that comprises the oligonucleotides described above.

This invention also provides a production inducer of interferon-α (IFN-α) from dendritic cell with any of the oligonucleotides described above.

This invention also provides a medical agent that has an effective amount of oligonucleotide described above as an active ingredient, wherein the medical agent is for cure of infectious diseases, cancer, respiratory diseases, allergic diseases, autoimmune disease, or wound.

Effect of the Invention

According to the present invention, it is possible to provide a new CpG oligonucleotide with superior stability.

According to the present invention, it is possible to provide a CpG oligonucleotide with immune adjustment power.

According to the present invention, it is possible to provide a medical agent that comprises immunomodulatory factors, which comprises a CpG oligonucleotide as an active ingredient.

According to the present invention, it is possible to provide CpG oligonucleotide that has less cytotoxicity.

BRIEF DESCRIPTION OF THE DRAWINGS

FIG. 1 is a gel electrophoresis photograph related to sequence Nos. 26 to 28 for evaluating the serum stability of the S-form and R-form oligonucleotide.

FIG. 2 is a gel electrophoresis photograph related to sequence Nos. 43 to 45 for evaluating the serum stability of the S-form and R-form oligonucleotide.

BEST MODE FOR CARRYING OUT THE INVENTION

Figure 3:
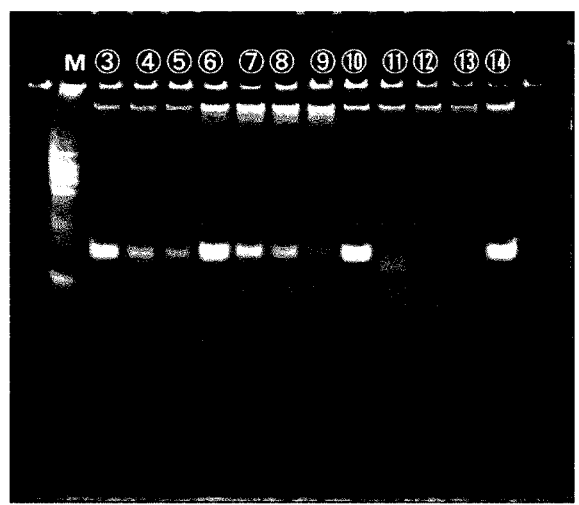
FIG. 3 is a gel electrophoresis photograph related to sequence Nos. 33 to 35 for evaluating the serum stability of the S-form and R-form oligonucleotide.

The first aspect of the present invention relates to oligonucleotides of 14-32 length nucleotides that comprise 5'-$X_1X_2$CpG$X_3X_4$-3' (Formula 1) sequences 2 to 4 times.

"Oligonucleotide" or "oligo" means sugar (e.g. ribose or deoxyribose) binding multiple nucleotides (i.e. Phosphate groups and substituted organic bases (either of substituted pyrimidines (e.g. cytosine (C), thymine (T) or uracil (U)) or substituted purine (e.g. adenine (A) or guanine (G))). As used in this specification, the term "oligonucleotide" means both of oligoribonucleotide (ORN) and oligodeoxyribonucleotide (ODN). The term "oligonucleotide" includes also oligonucleoside (i.e., the oligonucleotide without phosphate) and any other organic base polymer. Oligonucleotides can be obtained from existing nucleic acid sources (e.g. genome or cDNA), but synthetic one (e.g. produced by oligonucleotide synthesis) is preferred.

In formula (I), CpG represents unmethylated CpG without phosphate backbone modification. C is 2'-deoxycytidine. G is 2'-deoxyguanosine. p is a bond between nucleoside with phosphodiester.

In formula (I), $X_1X_2$ is either of AA, AT, GA or GT which may have phosphate backbone modification. In formula (I), $X_3X_4$ is either of TT, AT, AC, TA, TC or CG which may have phosphate backbone modification. The oligonucleotide of the present invention may have phosphate backbone modification on the site besides the CpG. The oligonucleotide may have phosphate backbone modification on the part besides the CpG motif consisting of 5'-$X_1X_2$CpG$X_3X_4$-3'. On the other hand, there is the problem previously said on phosphate backbone with phosphorothioate backbone modification between all of nucleotides, it may be preferable that oxygen atoms are replaced by sulfur atoms by more than 20% less than 95%, it may be more than 30% less than 95%, more than 20% less than 90%, more than 40% less than 95%, more than 40% less than 90%, more than 40% less than 80%, more than 50% less than 95%, more than 50% less than 90%, more than 20% less than 80%.

The $X_1X_2$ of this oligonucleotide is preferred to be either of AT, GA or GT which may have phosphate backbone modification and $X_3X_4$ is preferred to be either of TT, AT, AC, TA, TC or CG which may have phosphate backbone modification.

This oligonucleotide is preferred that $X_1X_2$ is either of AA, AT, GA or GT without phosphate backbone modification and $X_3X_4$ is either of TT, AT, AC, TC or CG without backbone modification.

In the case that the site besides the CpG motif with phosphate backbone modification is phosphorothioate, the site having at least one phosphate backbone modification portion other than the CpG motif may be S-form stereoisomer. In the case that at least one of the phosphate backbone modifications other than CpG motif is replaced by atoms or bases other than sulfur atoms, it may be preferred that the site takes s-type conformation when oxygen atoms are replaced by sulfur atoms.

The oligonucleotide of the present invention is preferred to have the following, or comprising any sequence, it is preferable that an oligonucleotide has any of the following sequences.

| SEQ No. | Sequence |
|---|---|
| [Formula 5] | |
| 1 | T*C*GTCGTT*T*T*GTCGTT*T*T*GTCGGG |
| 2 | G*G*GTCGTT*T*T*GTCGTT*T*T*GTCGGG |
| 3 | T*C*AACGTT*T*C*AACGTT*T*T |
| 4 | T*C*AACGTT*T*C*AACGTT*T*T*GG |
| 5 | T*C*AACGTT*T*C*AACGTT*G*G |
| 6 | T*C*AACGTT*T*C*AACGTT*G*G*G*G |
| 7 | T*C*AACGTT*T*T*AACGTT*T*T*AACGGG |
| 8 | T*C*AACGTT*T*A*ACGTT*T*T |
| 9 | T*C*AACGT*TAACGTT*T*T |
| 10 | T*C*AACGTT*T*A*AACGTT*T*A*AACGGG |
| 11 | T*C*AACGTTAACGTTAACGGG |
| 12 | T*C*GACGTT*T*T*GACGTT*T*T*GACGGG |
| 15 | G*G*GACGT*T*T*TGACGT*T*T*TGACGGGGG |
| 16 | T*C*GACGT*T*T*TGACGT*T*T*TGACGT*T*T*TGACGGG |
| 17 | T*C*GACGT*T*GACGT*T*GACGGG |
| 20 | T*C*GACGT*T*GACGT*T*GACGT*T*GACGGG |
| 21 | T*C*GACGTT*T*A*AACGTT*T*A*AACGTT*T*A*AACGGG |
| 22 | T*C*GACGTT*T*A*AACGTT*T*A*GACGTT*T*A*AACGGG |
| 23 | T*C*GACGTTAACGTTAACGTTAACGGG |
| [Formula 6] | |
| 24 | GGGACGTT*T*A*AACGTCTAGACGGG |
| 25 | T*C*GACGT*ACGT*ACGT*ACGGG |
| 26 | T*C*GACGTT*T*T*GACGTT*T*T*G*A*C*G*G |
| 29 | T*C*GACGTT*T*T*GACGTT*T*T*GACGG*G*G |
| 30 | T*C*GACGTT*T*T*GACGTT*T*T*GACGT*G*G |
| 31 | T*C*GACGTT*T*T*GACGTT*T*T*GACGTG*G*G |
| 32 | T*C*GACGTT*T*T*GACGTT*T*T*G*A*C*G*G*G |
| 33 | T*C*GACGTT*T*T*GACGTT*T*T*GACGG*G*G*G |
| 36 | T*C*GACGTT*T*T*GACGTT*T*T*GACG*G*G*G*G |
| 37 | T*C*GACGT*T*GACGT*T*GACGTG*G*G |
| 38 | G*G*T*G*C*ATCGAT*G*C*A*G*G*G*G*G |

-continued

| SEQ No. | Sequence |
|---|---|
| 39 | T*C*ATCGAT*T*T*ATCGAT*T*T*ATCGGG |
| 40 | G*G*T*G*C*GACGAT*G*C*A*G*G*G*G*G |
| 41 | G*G*G*G*GACGATCGTCGGG*G*G*G |
| 42 | G*G*GACGATATCGTCG*G*G*G*G*G |
| 43 | G*G*GACGACGTCGTCG*G*G*G*G*G |
| 46 | G*G*GGGACGATCGTCG*G*G*G*G*G |
| 47 | G*G*GACGCGCGTCG*G*G*G*G*G*G |
| 48 | G*G*G*G*TCGTTCG*G*G*G |

[Formula 7]

| SEQ No. | Sequence |
|---|---|
| 49 | T*C*ATCGAT*T*T*ATCGAT*T*T*A*A*C*G*G |
| 50 | T*C*GACGTTTTGACGTT*T*T*G*A*C*G*G*G |
| 51 | T*C*GACGTTTGACGTTTT*G*A*C*G*G*G |
| 52 | T*C*GACGT*T*GACGT*T*GACGG*G |
| 53 | TC*GACGT*T*GACGT*T*GACG*G*G |
| 51 | T*C*GACGT*T*GACGT*T*GACGG*G*G |
| 55 | T*C*GACGT*T*GACGT*T*GACT*G |
| 56 | TC*GACGT*T*GACGT*T*G*A*C*G*G*G |
| 57 | T*C*GACGTTGACGT*T*G*A*C*GG |
| 58 | T*C*ATCGATATCGA*T*G*A*C*G*G*G |
| 59 | T*C*GACGT*T*GACGT*T*GACG*G*G |
| 60 | T*C*GACGTT*T*T*GACGTT*T*T*G*G*G*G*G |
| 61 | TC*GACGTT*T*T*GACGTT*T*T*G*A*G*G*G*G |
| 62 | T*CCACGTT*T*T*GACGTT*T*T*G*T*G*G*G*G |
| 63 | T*C*G*ACGTT*G*ACGTT*G*A*C*G*GC |
| 64 | C*C*GACGTT*T*T*GACGTT*T*T*GACG*G*G |
| 65 | T*C*GACGTT*T*A*GACGTT*T*A*GACG*G*G |
| 66 | TC*GACGTT*T*T*GACGTT*T*T*GACG*A*A |
| 67 | T*C*GACGTT*T*T*GACGTT*T*T*GACG*T*T |
| 68 | TC*AACGTT*T*T*AACGTT*T*T*CACG*G*G |
| 69 | T*C*GACGTT*T*T*GACGTT*T*T*GGG |
| 70 | T*C*GACGTT*T*T*GACGTT*T*T*GACGTTGG |
| 71 | T*C*GACGTT*GACGTT*G*G*G |
| 72 | TC*GACGTT*T*T*T*ACGTT*T*T*G*ACG*G*G |
| 73 | T*C*G*CGTT*T*T*ACGTTTTGACGGG |
| 74 | T*C*G*ACGTT*T*T*G*ACGTT*T*T*G*ACG*G*G |
| 75 | T*C*GACGTA*GACGTA*GACG*G*G |
| 76 | T*A*GACGAT*T*C*GTCGTC*T*A*GACG*G*G |
| 77 | T*A*GACGA*C*GTCGT*A*GACC*G*G |
| 78 | T*C*G*ACGTTT*TC*ACGTT*T*T*G*A*C*G*G*G |
| 79 | T*C*G*ACGTT*T*T*T*A*ACGAC*T*T*G*A*C*G*G*G |

[Formula 8]

| SEQ No. | Sequence |
|---|---|
| 80 | T*C*G*ACGTTT*T*AACGAC*T*T*G*A*C*G*G*G |
| 81 | T*C*ATCGAT*T*T*ATCGAT*T*T*GACG*G*G |
| 82 | T*C*ATCGAT*T*T*ATCGAT*T*T*ATCGA*T*G*G*G |
| 83 | T*C*ATCGAT*T*T*ATCGAT*T*T*AT*C*G*G |
| 84 | T*C*ATCGAT*T*T*ATCGAT*T*T*ATCGAT*T*T*ATCG*G*G |
| 85 | T*C*ATCGAT*T*T*ATCGAT*T*T*ATCGAT*T*T*A*T*C*G*G*G |
| 86 | T*C*ATCGAT*T*T*ATCGAT*T*T*ATCGAT*A*T*C*G*G*G |
| 87 | T*T*ATCGAT*T*T*ATCGAT*T*T*G*A*C*G*G*G |
| 88 | T*C*ATCGATATCGAT*T*T*G*A*C*G*G*G |
| 89 | TCATCGAT*T*T*ATCGAT*T*T*A*T*C*G*G*G |
| 90 | T*C*ATCGAT*T*T*ATCGAT*T*T*G*A*C*G*A*T |
| 91 | T*C*GACGT*T*GACGT*T*GACGT*T*G*G*G |
| 92 | T*C*G*ACGT*T*G*ACGT*T*G*A*C*G*G*G |
| 93 | T*C*A*TCGAT*T*T*A*TCGAT*T*T*G*A*C*G*G*G |
| 94 | T*C*A*TCGAT*A*TCGAT*G*ACGT*T*T*G*G*G |
| 95 | T*C*GACGTTTGACGTTT*G*A*C*G*G*G |
| 96 | T*C*ATCGAT*T*T*ATCGAT*T*T*A*T*C*G*G*G |
| 97 | G*G*GACGATATCGTCG*G*G*G*G*G |
| 98 | G*G*GACGAC*G*TCGTCG*G*G*G*G*G |
| 99 | G*G*GACGACGTCGTCG*G*G*G*G |
| 100 | T*C*GACGACGTCGTCG*G*G*G*G*G |
| 101 | T*C*GACGACGTCGTCT*T*T*G*G*G |
| 102 | T*A*GACGACGTCGTCT*T*T*G*G*G |
| 103 | T*T*GACGACGTCGTCA*A*A*G*G*G |
| 104 | T*C*GACGTAGACGTCT*T*T*G*G*G |
| 105 | T*C*GACGTAGACGTTT*A*G*G*G |
| 106 | T*C*ATCGATATCGATT*T*T*G*G*G |
| 107 | T*T*ATCGATATCGATA*A*A*G*G*G |
| 108 | T*C*GACGTAGACGATCGA*T*G*G*G |
| 109 | T*C*GACGAC*T*T*GACGAC*T*T*G*A*C*G*G*G |
| 110 | T*C*GACGAC*T*T*GTCGTC*T*T*G*A*C*G*G*G |
| 111 | T*T*ATCGATATCGATA*T*C*G*A*T*G*G*G |
| 112 | T*T*ATCGATATCGATT*T*A*A*A*G*G*G |
| 113 | T*C*ATCGAT*T*T*ATCGAT*T*T*G*A*C*G*T*T |
| 114 | T*C*ATCGA*T*ATCGA*T*G*A*C*G*G*G*G |

-continued

| SEQ No. | Sequence |
|---|---|
| 115 | T*C*ATCGAT*ATCGA*T*G*G*G |
| 116 | T*C*GTCGTTGTCGT*T*G*A*C*G*G*G |
| 117 | T*C*G*TCGTT*T*T*G*TCGTT*T*T*G*A*C*G*G*G |
| 118 | T*C*GTCGTTGTCGTTG*A*C*G*A*C*G*G*G |

In above formula * indicates the stereoisomer by phosphate backbone modification. CG of the section corresponding to 5'-$X_1X_2$CpG$X_3X_4$-3 in above formula means unmethylated CpG without phosphate backbone modifications. The examples of phosphate backbone modifications are phosphothioate backbone modifications, phosphorodithioate backbone modifications, or phosphoramidate backbone modifications. In these phosphate backbone modifications, phosphothioate backbone modifications are preferred. phosphothioate backbone modifications means that converting one of the two nonbridging oxygen atoms bonding to phosphorus atoms comprising phosphodiester bond of neighbor nucleotides into sulfur atoms. At least one of the * is S-form stereoisomer. Here, S-form stereoisomer means, as described above, stereoisomer that takes S-form when their atoms or bases introduced instead of oxygen atoms are sulfur atoms.

The oligonucleotide of the present invention is preferred that the sequence satisfies the article (I) or described sequences above, and $X_1X_2$ is GA, and $X_3X_4$ is TT or AC.

The oligonucleotide of the present invention is preferred that it is one of the nucleotides described above, and phosphate backbone modifications which exist in at least one of the sites other than CpG motif are oligonucleotides including phosphorothioate. That is, as explained above, it is preferred that the oligonucleotide has phosphorothioate backbone modification also in the sites other than CpG. In this case, as explained above, S-form stereoisomer is preferred. However, in the present invention, it is preferred that no phosphorothioate backbone modification exists between each sequence.

The sequence consisting of 5'-$X_1X_2$CpG$X_3X_4$-3' of formula (I) define as CpG motif. Then, the oligonucleotide of the present invention is preferred to have a sequence -(G)$_m$- (m is 2 to 10 integer) by 5' end or 3' end of CpG motif.

The oligonucleotide of this invention is preferred to have a sequence composed of TC, TA, TG or CC by 5' end of CpG motif.

The oligonucleotide of this invention is preferred to include at least first CpG motif and the second one. First CpG motif and second one is bonded directly or including -(T)n- (n is an integer that represents 1 to 3), TA, TC between first CpG motif and second one.

The oligonucleotide of this invention is preferred to have the sequences 1, 2 or 3 bases are substituted from, inserted to, deleted from or added to (Sequence No. 13)
t$^{Sp}$c$^{Sp}$gacgtt$^{Sp}$t$^{Sp}$t$^{Sp}$gacgtt$^{Sp}$t$^{Sp}$t$^{Sp}$gacggg, (Sequence No. 18)
t$^{Sp}$c$^{Sp}$gacgt$^{Sp}$t$^{Sp}$gacgt$^{Sp}$t$^{Sp}$gacggg
or (Sequence No. 44)
g$^{Sp}$g$^{Sp}$gacgacgtcgtcg$^{Sp}$g$^{Sp}$g$^{Sp}$g$^{Sp}$g$^{Sp}$g These oligonucleotide are preferred to exhibit stability or activity same as Sequence No. 13, 18 or 44. Here, "cg" indicates unmethylated CpG and "$^{Sp}$" indicates that S-form phosphate backbone modification is introduced between the neighbor nucleotides.

The oligonucleotide of this invention is preferred to include (Sequence No. 13)
t$^{Sp}$c$^{Sp}$gacgtt$^{Sp}$t$^{Sp}$t$^{Sp}$gacgtt$^{Sp}$t$^{Sp}$t$^{Sp}$gacggg, (Sequence No. 18)
t$^{Sp}$c$^{Sp}$gacgt$^{Sp}$t$^{Sp}$gacgt$^{Sp}$t$^{Sp}$gacggg
or (Sequence No. 44)
g$^{Sp}$g$^{Sp}$gacgacgtcgtcg$^{Sp}$g$^{Sp}$g$^{Sp}$g$^{Sp}$g$^{Sp}$g Here, "cg" indicates unmethylated CpG with phosphate backbone modification and "$^{Sp}$" indicates that S-form phosphate backbone modification is introduced between the neighbor nucleotides.

Synthetic Method of Nucleotides

The synthetic method for nucleotides is publicly known. The nucleotides in present invention can be produced by the publicly known method. For example, it can adopt that the methods disclosed in U.S. Pat. No. 450,870 statement and international application No. 2010/064146 pamphlet.

The other examples of the method for synthesizing nucleotide are introduced in U.S. Pat. No. 4,942,646 official report and U.S. Pat. No. 5,912,332. The latter, the use of the solid support attachment linker to parallel synthesis or generic solid support, such as phosphate salt attaching controlled pore glass.

Furthermore, nucleotide can be produced by the method e.g. disclosed in U.S. Pat. No. 4,383,534 A. For example, It can be produced by β-cyanoethyl phosphoroamidate method (S. L. Beaucage, M. H. Caruthers, Tetrahedron Lett. 1981, 22, 1859-62) and nucleoside H-phosphonate method (Per J. Garegg et al., Tetrahedron Lett. 1986, 27, 4051-4; Brian C. Froehler et al., Nucl Acid Res 1986, 14, 5399-407; Per J. Garegg et al., Tetrahedron Lett. 1988, 27, 4055-8; Barbara L. Gaffney et al., Tetrahedron Lett., 29, 2619-22). These chemicals can be synthesized by a variety of automated nucleic acid synthesizers available in the market. These nucleic acids are called synthetic nucleic acid. Alternatively, it is possible to generate nucleic acids of the present invention on a large scale in a plasmid. (Sambrook T. et al., Molecular Cloning: A Laboratory Manual, Cold Spring Harbor Laboratory Press, New York, 1989) The nucleic acid of this invention can be separated into smaller pieces or administered whole. The nucleic acid is produced from nucleic acid sequence (e.g. genomic sequence and cDNA sequence) with the use of known techniques (e.g. techniques using restriction enzymes, exonuclease or endonuclease) The nucleic acid that has been prepared in this way is called isolated nucleic acid. An isolated nucleic acid, in general, is a nucleic acid which is separated from components which naturally are normally associated. For example, the isolated nucleic acid is a nucleic acid that is separated from the cells, nucleus, mitochondria and chromatin. The combination motif nucleic acid of the present invention includes both synthesized combination motif nucleic acids and isolated combination motif nucleic acids.

The combination motif oligonucleotides, if necessary, have a relatively resistant to degradation (e.g., are stabilized) are preferred in the use of in vivo. A "stabilized nucleic acid molecule" means a nucleic acid molecule that is relatively resistant for in vivo degradation (e.g., exonuclease or endonuclease). The nucleic acid stabilization is achieved through the phosphate backbone modification. The stabilized nucleic acid that is preferred in the present invention has a modified backbone. This modification of the nucleic acid backbone provides increasing the activity of the combination motif oligonucleotide when administered in vivo. In some cases, the combination motif oligonucleotides with phosphorothioate bond provide maximum activity and protect the nucleic acid from degradation by intracellular exonucleases and cellular endonucleases. Other modified nucleic acids, modified phosphodiester nucleic acids, combinations of phosphodiester nucleic acids and phosphorothioate nucleic acids (i.e. chimeric), methylphosphonate, methylphosphorothioate, phosphorodithioate, p-ethoxy, and combinations thereof mentioned are.

The modified backbones (e.g., phosphorothioates) can be synthesized by using automated techniques employing either phosphoramidate chemistry or H-phosphonate chemistry. Aryl-phosphonate and alkyl-phosphonates can be generated, for example, as described in U.S. Pat. No. 4,469,863. And alkylphosphotriester (charged oxygen is alkylated as described in U.S. Pat. No. 5,023,243 and EP patent No. 092,574) can be produced using commercially available reagents by automated solid-phase synthesis. Methods for making modifications and substitutions of other DNA backbone have been described. (e.g., Uhlmann E and Peyman A, Chem. Rev. 1990, 90, 544; Goodchild J., Bioconjugate Chem. 1990, 1, 165)

The oligonucleotides obtained by synthesis may be purified by known methods, e.g., purified, deprotected, desalted and dialyzed by reversed phase HPLC. In this way, the oligonucleotides of the present invention can be isolated and purified.

This invention provides composition with one of the above oligonucleotides. This composition is a medicine composition. The composition contains an effective amount of any of the oligonucleotides described above and it may contain appropriate known carrier. The carrier may be a solvent such as water or alcohol. The carrier can be optional excipients, diluents, fillers, salts, buffers, stabilizers, solubilizers, lipids or other substance which is well known for medicine compositions in the art.

This invention also provides a vaccine adjuvant with oligonucleotide described above. The vaccine adjuvant, if necessary, may contain a pharmaceutically acceptable carrier. U.S. Pat. No. 4,126,252 discloses vaccine adjuvant with oligonucleotide. The vaccine adjuvant with the oligonucleotide of this invention can include the disclosed elements in this publication properly.

This invention also provides the interferon-α (IFN-α) production inducing agent from dendritic cells including any of the oligonucleotides above. The present invention also provides a cure for infection, cancer, respiratory diseases, allergic diseases, autoimmune disease or wound healing comprising an effective amount of any of the oligonucleotides described above as an active ingredient.

The examples of the infection cure of this invention, are fungal infection, persistent fungal infection, bacterial infection, candidiasis, chronic mucocutaneous candidiasis (CMC), aspergillosis, cryptococcosis disease, viral infection, persistent viral infection, human immunodeficiency virus (HIV) infections, B-type hepatitis virus (HBV) infection, C-type hepatitis virus infection, persistent bacterial infection, mycobacterial infection, M. tuberculosis infection, M. bovis infection, and M. leprae infection. For example, U.S. Pat. No. 4,688,815 official report indicates that interferon-α is effective in the treatment of the infections including hepatitis C virus (HCV) infection, and U.S. Pat. No. 4,607,452 indicates that interferon-α is effective in the treatment of the infections (e.g., mycobacterial disease, malaria, leishmaniasis, toxoplasmosis, schistosomiasis and liver fluke disease). The cure of this invention is also effective in the treatment of infections by producing interferon-α.

Cancer in cancer cure of this invention includes known cancer and tumors. For example, U.S. Pat. No. 4,607,452 official report and patent No. 2011-503039 official report disclose that interferon-α (IFN-α) is effective in the treatment of cancer and tumors. For this reason, the cancer cure is effective in the treatment of cancer and tumors.

The examples of respiratory disease in respiratory disease cure of this invention are blasphemy, asthma, allergic rhinitis, bronchitis, pneumonia, acute respiratory distress syndrome (ARDS), and allergic bronchopulmonary aspergillosis. For example, patent No. 2004-505046 official report indicates that interferon-α is effective in the treatment of respiratory diseases.

The examples of allergic disease in allergic disease cure of this invention are systemic inflammatory response syndrome (SIRS), anaphylaxis or anaphylactoid reaction, allergic vasculitis, hepatitis, nephritis, nephropathy, pancreatitis, rhinitis, arthritis, inflammatory eye diseases (e.g., conjunctivitis, etc.), inflammatory bowel disease (e.g., ulcerative colitis, Crohn's disease, eosinophilic gastrointestinal disease, etc.), brain and cardiovascular system diseases (e.g., arteriosclerosis, thrombosis, ischemia/reperfusion injury, restenosis, infarction, etc.), skin disease (e.g., dermatitis (e.g., atopic dermatitis, psoriasis, contact dermatitis, eczema, urticaria, pruritus, etc.), etc.), autoimmune diseases (such as multiple sclerosis, rheumatoid arthritis, systemic lupus erythematosus, I type diabetes, glomerulonephritis, Sjogren's syndrome, etc.), transplanted organ rejection. For example, patent No. 2004-50546 official report indicates that interferon-α is effective in the treatment of allergic disease. For this reason, the cure for allergic diseases of this invention, by producing interferon-α, is effective in the treatment of allergic diseases.

The examples of autoimmune disease in autoimmune disease cure of this invention are acute idiopathic thrombocytopenic purpura, chronic idiopathic thrombocytopenic purpura, Sydenham's chorea, myasthenia gravis, systemic lupus erythematosus, lupus nephritis, rheumatic fever, polyglandular syndromes, bullous pemphigoid, diabetes, Henoch-Schonlein purpura, post Streptococcus nephritis (post-streptococcalnephritis), erythema nodosum, Takayasu's arteritis, Addison's disease, rheumatoid arthritis, multiple sclerosis, sarcoidosis, ulcerative colitis, erythema multiforme, IgA nephropathy, nodule sex multiple arteritis, ankylosing spondylitis, Goodpasture's syndrome, thromboangiitis obliterans (thromboangitisubiterans), Sjogren's syndrome, primary biliary cirrhosis, Hashimoto's thyroiditis, thyrotoxicosis, scleroderma, chronic active hepatitis, polymyositis/dermatomyositis, polychondritis, pemphigus vulgaris (parnphigus vulgaris), Wegener's granulomatosis, membranous nephropathy, amyotrophic lateral sclerosis, spinal cord wax, giant cell arteritis/polymyalgia pain, pernicious anemia, rapidly progressive glomerulonephritis, psoriasis, and fibrosing alveolitis. For example, JP 2007-528209 A indicates that interferon-α is effective in the treatment of these autoimmune disease. For this reason, The cure for autoimmune diseases of this invention, by producing interferon-α, is effective in the treatment of autoimmune diseases.

Wounds in wound cure of this invention include skin disorders, wounds caused by surgery, hypertrophic scars, keloid. For example, patent No. 2003-503313 official report disclose that interferon-α (IFN-α) is effective in the treatment of skin disorders. For this reason, the wound cure is also effective in the treatment of wounds by producing interferon-α.

The interferon-α (IFN-α) production inducer and these medicine can be produced, for example, by the method disclosed in U.S. Pat. No. 4,383,534.

The nucleotide of this invention can be used to inducing type 1 IFN (i.e., IFN-α and IFN-β). This method includes a progress that the cell capable of expressing type 1 IFN is contacted with an effective amount of combination motif oligonucleotides of this invention to induce expression of type 1 IFN with the cell. It has been recognized recently that major IFN-α producer cell type in humans is plasmacytoid dendritic cell (pDC). This cell type exists by very low frequency (0.2~0.4%) and this cell type is characterized by lineage negative (i.e., CD3, CD14, also CD19 are not stained), CD11c negative and phenotypic positive for CD4, CD123 (IL-3Rα) and class II major histocompatibility complex (MHC class II). The methods for measuring type 1 IFN are known by one of ordinary skill in the art, and examples of such methods are enzyme-linked immunosorbent assay (ELISA), bioassay and fluorescence cell analysis (FACS). These types of assay may be performed by readily available reagents and kits.

This oligonucleotide is effective to induce systemic immune response and/or mucosal immune response. The combination motif oligonucleotide of this invention can be delivered to a subject exposed to antigens for inducing enhancement of the immune response to antigens. Therefore, for example, the combination motif nucleotide is useful for vaccine adjuvant. Examples of the main agent functioning as adjuvant are a variety of vaccines. The adjuvant can increase the efficiency of antigen to be incorporated into the immune cells. The adjuvant is preferred to be able to be improved or enhanced or assist the original action with the active ingredient of the main agent. The examples for the vacctine are vacctine for virus and vacctine for B hepatitis, A hepatitis, Japanese encephalitis, pediatric pneumococcal, diphtheria, cough hundred days, tetanus, measles, rubella, mumps, chicken pox and tuberculosis (BCG vaccine). Examples of the vaccine for virus are influenza vaccine, polio vaccine, human papillomavirus vaccine, rotavirus vaccine, vaccine for non-flops, polio vaccines and AIDS vaccine. The oligonucleotide of this invention functions as adjuvant by a very small amount. Therefore, the oligonucleotide of this invention have low cytotoxic compared with the conventional adjuvant and there are very few side effects. This makes the vaccine which is administered in many targets very useful.

This oligonucleotide can be administered with a non-nucleic acid adjuvant. The non-nucleic acid adjuvant is arbitrary molecule or compound, except herein oligonucleotides which can stimulate humoral immune responses and/or cellular immune responses. The examples of the non-nucleic acid are adjuvants causing depot effect, immune stimulating adjuvants, and adjuvants causing depot effect and stimulating immune system. As used herein, the non-nucleic acid mucosal adjuvant is an adjuvant that can induce mucosal immune responses when administered to a mucosal surface with antigen in the subject.

The oligonucleotide of this invention may be formulated as a pharmaceutical composition in a pharmaceutically acceptable carrier. This oligonucleotide may be administrated to a subject directly or with a nucleic acid delivery complex. The nucleic acid delivery complex means a nucleic acid which is associated (e.g., ionic bond or covalent bond, or encapsulated in the way) with a targeting way (e.g., molecules which generate high affinity bond to target cells (e.g., surface of B cell) and/or increase in cellular uptake by target cells.). The examples of the nucleic acid delivery complex are nucleic acid associated with sterols such as cholesterol, lipids (e.g., cationic lipids, virosomes or liposomes) or target cell specific bonding factors (egg, ligands recognized by target cell specific receptor). Preferred complex can be enough stable in vivo to prevent from significant de-coupling before the internalization by the target cell. But the complex can be cleavage under appropriate conditions in the cells so that the nucleic acid is released in a functional form.

This oligonucleotide and/or the antigen and/or other therapeutic agents can be administered separately (e.g. in saline or buffer solution), and may also be administered using any known delivery vehicles.

Dose of the compounds described herein for mucosal delivery or topical delivery is typically in the range of about 0.1 μg/dose to 10 mg/dose. The doses depend on whether it is administered daily, weekly, or monthly, and in any other time. More typically, mucosal doses or local doses are in the range of about 10 μg/dose to 5 mg/dose. The most typically, it is about 100 μg/dose to 1 mg/dose, and the administrations of 2-4 times are performed apart for a few days or a few weeks. More typically, dose for immune stimulant is in the range of about 1 μg/dose to 10 mg/dose, most typically, in the range of about 10 μg dose to 1 mg/dose. Then, the administrations are performed daily or weekly. The dose of the compounds (this compound is delivered with an antigen, are not delivered with another therapeutic agent) described herein for parenteral delivery in order to induce an antigen-specific immune response, is typically 5 to 10,000-fold more than effective mucosal dose for vaccine adjuvant or immune stimulating applied. More typically, it is 10 to 1,000-fold greater, and most typically 20 to 100 times greater. In case of that the oligonucleotide is administered in combination with other therapeutic agents or administered using specialized delivery vehicles, the dose of the compounds which is for inducing an innate immune response, increasing ADCC or inducing an antigen-specific immune response, described herein for parenteral delivery is typically in the range of about 0.1 μg/dose to 10 mg/dose. The doses depend on whether it is administered daily, weekly, or monthly, and in any other time. More typically parenteral doses for these purposes is in the range of about 10 μg/dose to 5 mg/dose. The most typically, it is about 100 μg/dose to 1 mg/dose, and the administrations of 2-4 times are performed apart for a few days or a few weeks. However, in some embodiments, parenteral doses for these purposes may be used in the 5 to 10,000-fold greater range than the typical doses described above.

In the present specification, the term "effective amount" means the required or sufficient amount to achieve the desired biological effect. For example, an effective amount of a nucleic acid for treating an infection means the amount required to treat the infection. Combined with the teachings provided herein, by selecting the various active compounds and weighing factors (For example, potency, relative bioavailability, patient body weight, severity of adverse side-effects and preferred mode of administration), the effective prevention regimen and the effective therapeutic regimen, which are very effective to treat a particular subject without causing substantial toxicity, can be plan. The effective amount for any particular application may vary depending on factors, such as disease or condition being treated, the particular oligonucleotide being administered, antigen, subject size, and the severity of the disease and conditions. A skilled in the art can be empirically determined the effective amount of a particular oligonucleotide and/or antigen and/or other therapeutic agents without the need for undue experiments.

A therapeutically effective amount for any of the compounds described herein can first be determined based on the knowledge obtained in animal experiments. An effective dose for the treatment also can be determined based on the data about the CpG oligonucleotide which has been tested in human (human clinical trials has been started) and the data when the mucosal or local administration of known compounds having similar pharmacological activities [For example, other mucosal adjuvants (for example, LT and other antigens for vaccination)]. For parenteral administration, it is necessary to use higher dose. The applied dose can be adjusted based on the relative bioavailability and potency of the compounds administered. Adjusting the dose to achieve the maximal efficacy using the methods and other methods is well known in the art. In addition, a skilled person can easily adjust the dose.

When administered, formulation of the present invention is dissolved in a pharmaceutically demand solutions. The solution conventionally may include salts of pharmaceutically acceptable concentrations, buffering agents, preservatives, compatible carriers, adjuvants, and optionally other therapeutic ingredients.

For use in therapy, the oligonucleotide of the effective amount may be administered to a subject using any manner for delivering the nucleic acids to desired surface (for example, a mucosal surface and a systemically surface). Administering the pharmaceutical compositions of this invention may be accomplished by any means known to those skilled in the art. Preferred routes of administration are oral route, parenteral route, intramuscular route, intranasal route, the intratracheal route, inhalation routes, ocular route, sublingual, vaginal routes, rectal route, and the like, but not limited those listed herein.

For oral administration, the compounds (i.e., oligonucleotides, antigens, and other therapeutic agents) can be easily prepared by combining the active compound with known pharmaceutically acceptable carriers in the art. Such carriers enable the compounds of the present invention to be formulated as tablets to be taken orally by a subject to be targeted, pills, dragees, capsules, liquids, gels, syrups, slurries, suspensions and the like. The pharmaceutical preparations for oral administration may be obtained as solid excipient by adding suitable auxiliaries if necessary, subsequently grounding the resulting mixture and forming the tablet cores or the dragee cores by processing the mixture of granules. In particular, suitable excipients are fillers [for example, sugar (lactose, sucrose, mannitol and sorbitol); cellulose preparations (for example, corn starch, wheat starch, Rice starch, potato starch, gelatin, tragacanth gum, methyl cellulose, hydroxypropyl methyl-cellulose, sodium carboxymethyl-cellulose) and/or polyvinylpyrrolidone (PVP)]. If necessary, the disintegrating agents [for example, cross-linked polyvinyl pyrrolidone, agar, alginic acid or a salt thereof (for example, sodium alginate)] may be added. If necessary, the oral formulations may also be administered in saline or buffer solution to neutralize the acidic internal state. In addition, the oral formulations may be administered without any carriers.

The dragee cores are provided with suitable coatings. For this purpose, concentrated sugar solutions can be used. If necessary, the concentrated sugar solutions may contain gum arabic, talc, polyvinyl pyrrolidone, carbopol gel, polyethylene glycol and/or titanium dioxide, lacquer solutions, suitable organic solvents or solvent mixtures. In order to identify or characterize different combinations of active compound doses, dyestuffs or pigments may be added to the tablets or the dragee coatings.

Examples of pharmaceutical preparations which can be administered orally are a fabricated push-fit capsule of gelatin, and a soft sealed capsule made of gelatin and a plasticizer (for example, glycerol or sorbitol). The push-fit capsule may contain the active ingredient, if necessary, mixed with fillers (for example, lactose), binders (for example, starch) and/or lubricants (for example, talc or magnesium stearate) and stabilizers. In the soft capsule, the active compounds may be dissolved or suspended in suitable liquids (for example, fatty oils, liquid paraffin, or liquid polyethylene glycol). In addition, the stabilizer may be added. Microspheres formulated for oral administration may also be used. Such microspheres have been well known in the art. All formulations for oral administration may be used in appropriate dosage.

For buccal administration, the compositions may take the form of tablets or lozenges formulated in conventional manner.

For inhalation administration, the compounds of the present invention may be administered by aerosol spray from pressurized packs or a nebulizer using a suitable propellant (for example, dichlorodifluoromethane, trichlorofluoromethane, dichlorotetrafluoroethane, carbon dioxide or other suitable gas) as with a conventional usage. When using a pressurized aerosol, the dosage unit can be determined by providing a valve to deliver a metered amount. For use in an inhaler or insufflator, such gelatin capsules and cartridges, which contain a powder mixture of the compound and a suitable powder base, may be provided.

If the compound should be delivered systemically, the compound can be provided in a form that can be administered parenterally by injection (for example, bolus injection or continuous infusion). The formulations for injection may be provided in unit dosage form (for example, an ampoule or multi-dose containers) with preservative agent. The compounds may take such forms as solutions, emulsions or suspension in oily or aqueous vehicles. In addition, they may contain the formulations (for example, suspending agents, stabilizing agents and/or dispersing agents).

Pharmaceutical formulations for parenteral administration include aqueous solutions of the active compounds which are water soluble. In addition, suspensions of the active compounds may be provided as appropriate oily injection suspensions. Suitable lipophilic solvents or vehicles include fatty oils (for example, sesame oil), synthetic fatty acid esters for example, ethyl oleate or triglycerides), or liposomes. Aqueous injection suspensions may contain substances which increase the viscosity of the suspension (for example, sodium carboxymethyl cellulose, sorbitol, or dextran). In order to prepare highly concentrated solutions, the suspension may also include agents that increase the solubility of the appropriate stabilizers or compounds thereof as necessary.

Alternatively, the active compounds may be in powder form which can be configured prior to use with a suitable vehicle (for example, sterile pyrogen-free water).

The compounds may be provided in the form for rectal or vaginal administration (for example, suppositories or retention enemas which may contain conventional suppository bases such as cocoa butter or other glycerides).

In addition to the above, the compounds may also be provided as a depot preparation. Such long acting formulations may be provided by using a suitable polymeric or hydrophobic materials (for example, as an emulsion in an acceptable oil), by using an ion exchange resin or by using poorly soluble derivatives (such as salts poorly soluble).

The pharmaceutical compositions may also include carriers or excipients which is a suitable solid or gel phase. Examples of such carriers or excipients include calcium carbonate, calcium phosphate, various sugars, starches, cellulose derivatives, gelatin, and polymers (for example, polyethylene glycol), but not limited thereto.

Suitable liquid pharmaceutical preparation form or solid pharmaceutical preparation forms are micro-encapsulated, chelated, coated on microscopic gold particles, included in liposomes, contained in the aerosol to be sprayed, included in the pellet for implantation into the skin, dried form in sharp on the object for scratching the skin, aqueous solution for inhalation or saline solution. In addition, the pharmaceutical compositions includes granules, powders, tablets, coated tablets, (micro) capsules, suppositories, syrups, emulsions, suspensions, creams, drops or preparations, which can release the active compound a long period of time. As described above, the formulations contain the excipients, the additives and/or the adjuvants (for example, disintegrants, binders, coating agents, sweetening agents, lubricants, flavoring agents, sweeteners, or solubilized agents) conventionally. The pharmaceutical compositions are suitable for use in a variety of drug delivery systems. Brief review of methods for drug delivery is mentioned in Langer (1990) Science 249: 1527-33 (which is incorporated herein by reference).

The oligonucleotide and that containing other therapeutic agent and/or antigen as necessary may be administered without being any processed, or may be administered in the form of a pharmaceutically acceptable salt. When administered in the form of a pharmaceutically acceptable salt, the salt should be pharmaceutically acceptable. However, the pharmaceutically acceptable salt may be used to prepare the pharmaceutically acceptable salts. Examples of such salts are the followings, but not limited thereto: HCl, hydrobromic acid, sulfuric acid, nitric acid, phosphoric acid, maleic acid, acetic acid, salicylic acid, p-toluene sulfonic acid, salt tartaric acid, citric acid, methane sulfonic acid, formic acid, malonic acid, succinic acid, naphthalene-2-sulfonic acid and benzene sulfonic acid. In addition, such salts may be prepared as alkali metal salts or alkaline earth metal salts (for example, sodium salts of carboxylic acid, potassium salt or calcium salt).

Examples of the suitable buffering agents are followings: acetic acid and its salt (1-2% w/v); citric acid and its salt (1-3% w/v); boric acid and its salt (0.5-2.5% w/v); and phosphoric acid and its salt (0.8-2% w/v). Examples of the suitable preservatives are followings: benzalkonium chloride (0.003-0.03% w/v); chlorobutanol (0.3-0.9% w/v); parabens (0.01-0.25% w/v), and thimerosal (0.004-0.02% w/v).

The pharmaceutical compositions of the present invention may contain an effective amount of the oligonucleotide, the antigen and/or other agents in a pharmaceutically acceptable carrier as necessary. The term "pharmaceutically acceptable carrier" means one or more compatible filler, diluent, or encapsulating agent which is solid or liquid and is suitable for administration to humans or other vertebrates. The term "carrier" means a natural or synthetic, organic or inorganic component which is added to in order to facilitate the application of the active ingredient. Components of the pharmaceutical compositions can be mixed with the compounds of this invention and each component in a manner that the components do not interact with each other.

For the treatment of individual subjects, different capacities of the pharmaceutical compositions of the present invention are required based on activity of the compound, manner of administration, purpose of the immunization (i.e., prophylactic immunization or immunotherapy), the nature and severity of the disorder, the age of the patient and weight of the patient. Administration of a desired dose may be performed by administering an amount corresponding to dosage units at a time or by administering a smaller amount multiple times.

Examples of other delivery systems include time-release system, delayed release system, or sustained release system. Such systems may avoid repeated administrations of the compound, and may increase the convenience to the subject and the physician. Many types of release delivery systems are available, and are known to those skilled in the art. Examples of the release delivery systems include a polymer-based system (for example, poly(lactide-glycolide), copoly oxalate, polycaprolactone, polyesteramides, polyorthoesters, polyhydroxybutyric acid, and polyanhydrides). For example, microcapsules of the polymer containing the pharmaceutical compositions are described in U.S. Pat. No. 5,075,109. The delivery systems also include non-polymeric system. Examples of the non-polymeric system are followings: lipids (sterols (for example, cholesterol, cholesterol ester), and fatty acids or natural fats (for example, monoglycerides, diglycerides, and triglycerides) and the like); hydrogel release systems; silastic system; peptide-based systems; wax coating; compressed tablets using conventional binders and excipients; partial fused to the implant. In particular, the system includes the followings, but not limited thereto: (a) an erosion-based system which the agent of the present invention is contained in a form located in the matrix (U.S. Pat. No. 4,452,775, U.S. Pat. No. 4,675,189 and U.S. Pat. No. 5,736,152); (b) a diffusion system which the active ingredient penetrate at a controlled rate from the polymer (U.S. Pat. No. 3,854,480, U.S. Pat. No. 5,133,974 and U.S. Pat. No. 5,407,686). In addition, pump-based hardware delivery systems can be used. Some of them are adapted for implantation.

The invention is further illustrated by the following examples. The following examples are should not be construed as further limiting. Throughout this specification, all of the contents of the cited documents are incorporated herein.

Working Example 1

Synthesis of Chiral CpG Oligonucleic Acid

CpG Oligonucleic Acid (Mixture)

The oligonucleic acid (mixture) which had been synthesized using phosphoramidite method and purified using HPLC were purchased from GeneDesign, Inc.

Synthesis of the CpG oligonucleotide of which the three-dimensional structure is modified. Extension of nucleic acid chain was performed by repeating the following steps (i)-(iv).

(i) 3% DCA (dichloroacetic acid)/$CH_2Cl_2$ (15 sec),
(ii) Condensation reaction [A mixture of 0.1 M monomer solution in MeCN (See below) and 1 M PhIMT (Trifluoromethanesulfonic acid N-phenylimidazolium) solution in MeCN in ratio 1:1, 5 min],
(iii) Capping reaction [A mixture of 0.5 M CF₃Colm in THF and 1 M DMAN (1,8-bis(dimethylamino)naphthalene)) in THF in ratio 1:1, 30 sec],
(iv) Sulfurization reaction (0.1 M DDTT in MeCN, 90 sec) or oxidization reaction (0.02 M I₂ in H₂O-Pyridine-THF solution, 15 sec).

After the chain elongation of nucleic acid, a solid phase carrier was collected in 1.5 ml microtube. The solid phase carrier was treated with high concentrated aqueous ammonia (1.2 ml, 55 degrees, 48 hours). The solid phase carrier was removed by filtration. A filtrate was dried in reduced pressure, and dissolved in water (1.0 ml). Then, the oligomer was isolated and purified by using a reversed-phase HPLC.

A procedure for adjusting 0.1 M monomer solution in MeCN (in case of Rp-Th). Thymidylic acid H-phosphonate monoester (25 μmol) was azeotropic-dried with dehydrated pyridine and dehydrated toluene. It was dissolved in MeCN-CMP (N-Cyanomethylpiperidine) solution (9:1, v/v; 250 μL). Subsequently, Ph₃PCl₂ (62.5 μmol) was added, and the solution was stirred for 10 min. Then, AA-L (30 μmol; AA-D was used when Sp form was selected.) was added, and the solution was stirred for 10 min. In this way, the monomer solution was obtained.

In the description above, DDTT, AA-L and AA-D mean the abbreviated designation of the following compounds respectively. The obtained oligonucleic acids are shown in Table 1.

[Formula 1]

DDTT:

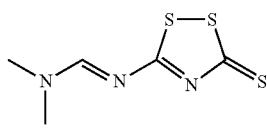

AA-L:

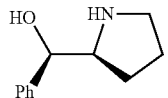

AA-D:

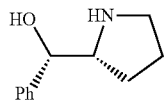

TABLE 1

The oligonucleic acids obtained in Embodiment 1

| SEQ No. | Sequence |
|---|---|
| 1 | T*C*GTCGTT*T*T*GTCGTT*T*T*GTCGGG |
| 2 | G*G*GTCGTT*T*T*GTCGTT*T*T*GTCGGG |
| 3 | T*C*AACGTT*T*C*AACGTT*T*T |
| 4 | T*C*AACGTT*T*C*AACGTT*T*T*GG |
| 5 | T*C*AACGTT*T*C*AACGTT*G*G |
| 6 | T*C*AACGTT*T*C*AACGTT*G*G*G*G |
| 7 | T*C*AACGTT*T*T*AACGTT*T*T*AACGGG |

TABLE 1-continued

The oligonucleic acids obtained in Embodiment 1

| SEQ No. | Sequence |
|---|---|
| 8 | T*C*AACGTT*T*A*ACGTT*T*T |
| 9 | T*C*AACGT*TAACGTT*T*T |
| 10 | T*C*AACGTT*T*A*AACGTT*T*A*AACGGG |
| 11 | T*C*AACGTTAACGTTAACGGG |
| 12 | T*C*GACGTT*T*T*GACGTT*T*T*GACGGG |
| 13 | TsCsGACGTTsTsTsGACGTTsTsTsGACGGG |
| 14 | TrCrGACGTTrTrTrGACGTTrTrTrGACGGG |
| 15 | G*G*GACGT*T*T*TGACGT*T*T*TGACGGGGG |
| 16 | T*C*GACGT*T*T*TGACGT*T*T*TGACGT*T*T*TGACGGG |
| 17 | T*C*GACGT*T*GACGT*T*GACGGG |
| 18 | TsCsGACGTsTsGACGTsTsGACGGG |
| 19 | TrCrGACGTrTrGACGTrTrGACGGG |
| 20 | T*C*GACGT*T*GACGT*T*GACGT*T*GACGGG |
| 21 | T*C*GACGTT*T*A*AACGTT*T*A*AACGTT*T*A*AACGGG |
| 22 | T*C*GACGTT*T*A*AACGTT*T*A*GACGTT*T*A*AACGGG |
| 23 | T*C*GACGTTAACGTTAACGTTAACGGG |
| 24 | GGGACGTT*T*A*AACGTCTAGACGGG |
| 25 | T*C*GACGT*ACGT*ACGT*ACGGG |
| 26 | T*C*GACGTT*T*T*GACGTT*T*T*G*A*C*G*G |
| 29 | T*C*GACGTT*T*T*GACGTT*T*T*GACGG*G*G |
| 28 | TrCrGACGTTrTrTrGACGTTrTrTrGrArCrGrGrG |
| 29 | T*C*GACGTT*T*T*GACGTT*T*T*GACGG*G*G |
| 30 | T*C*GACGTT*T*T*GACGTT*T*T*GACGT*G*G |
| 31 | T*C*GACGTT*T*T*GACGTT*T*T*GACGTG*G*G |
| 32 | T*C*GACGTT*T*T*GACGTT*T*T*G*A*C*G*G*G |
| 33 | T*C*GACGTT*T*T*GACGTT*T*T*GACGG*G*G*G |
| 34 | TsCsGACGTTsTsTsGACGTTsTsTsGACGGsGsGsGsG |
| 35 | TrCrGACGTTrTrTrGACGTTrTrTrGACGGrGrGrGrG |
| 36 | T*C*GACGTT*T*T*GACGTT*T*T*GACG*G*G*G*G |
| 37 | T*C*GACGT*T*GACGT*T*GACGTG*G*G |
| 38 | G*G*T*G*C*ATCGAT*G*C*A*G*G*G*G*G |
| 39 | T*C*ATCGAT*T*T*ATCGAT*T*T*ATCGGG |
| 40 | G*G*T*G*C*GACGAT*G*C*A*G*G*G*G*G |
| 41 | G*G*G*G*GACGATCGTCGGG*G*G*G |
| 42 | G*G*GACGATATCGTCG*G*G*G*G |
| 43 | G*G*GACGACGTCGTCG*G*G*G*G |
| 44 | GsGsGACGACGTCGTCGsGsGsGsG |
| 45 | GrGrGACGACGTCGTCGrGrGrGrG |

TABLE 1-continued

The oligonucleic acids obtained in Embodiment 1

| SEQ No. | Sequence |
|---|---|
| 46 | G*G*GGGACGATCGTCG*G*G*G*G |
| 47 | G*G*GACGCGCGTCG*G*G*G*G*G*G |
| 48 | G*G*G*G*TCGTTCG*G*G*G |

In above tables, * indicates the position that the S-form phosphorothioate backbone modification and the R-form phosphorothioate modification were induced into the backbone at random. In above table, "s" indicates the S-form phosphorothioate modification. In above table, "r" indicates the R-form phosphorothioate modification.

Working Example 2

Induction of Production of IFN-α in Simian Peripheral Blood Mononuclear Cells (PBMC)

The blood derived from *Macaca fascicularis* which has tested negative for B virus, diluted to 3 times with Hanks' Balanced Salt Solution. Then, the sample was layered on Ficoll-Paque PLUS centrifugation medium and centrifuged (2,600 rpm, 30 min). A fraction containing the peripheral blood mononuclear cells (PBMC) was obtained. After the PBMC was washed with RPMI medium (1% penicillin and streptomycin), the PBMC was suspended in RPMI medium (10% FBS, 1% penicillin and streptomycin) at a cell density of $3 \times 10^6$ cells/ml. The cells were cultured with various oligonucleic acids (mixture containing oligo DNA and DOTAP in a ratio of 1:3.2) in 96-well round-bottom plate for 17-24 hours using 5% $CO_2$ incubator. After the cultivation, cell culture supernatant was obtained by centrifuging (500 rpm, 5 min) the culture medium. Then, the concentration of IFN-α in the cell culture supernatant was measured using ELISA kit (PBL Assay Science).

The result was shown in Table 2. Table 2 indicates the IFN-α production induced by the oligonucleic acids of SEQ No: 1-48 in simian peripheral blood mononuclear cells.

TABLE 2

Inductive effect of production of INF-α in simian peripheral blood mononuclear cells

| | IFN-α (pg/ml) | |
|---|---|---|
| SEQ No. | Average | ±SE |
| 1 | 3583 | 1634.84 |
| 2 | 1006 | 1161.33 |
| 3 | 583 | 299.44 |
| 4 | 2151 | 1259.46 |
| 5 | 388 | 144.35 |
| 6 | 1767 | 1176.08 |
| 7 | 3982 | 1588.50 |
| 8 | 2887 | 1080.05 |
| 9 | 2845 | 1127.16 |
| 10 | 256 | 173.70 |
| 11 | 1400 | 508.91 |
| 12 | 4001 | 607.38 |
| 13 | 2776 | 1020.29 |
| 14 | 3966 | 1155.61 |
| 15 | 1453 | 314.77 |
| 16 | 3719 | 849.99 |
| 17 | 2694 | 441.82 |
| 18 | 3207 | 763.07 |

TABLE 2-continued

Inductive effect of production of INF-α in simian peripheral blood mononuclear cells

| | IFN-α (pg/ml) | |
|---|---|---|
| SEQ No. | Average | ±SE |
| 19 | 2583 | 711.25 |
| 20 | 2457 | 507.22 |
| 21 | 2287 | 857.47 |
| 22 | 2492 | 985.99 |
| 23 | 3082 | 1379.50 |
| 24 | 1329 | 302.81 |
| 25 | 2373 | 1062.95 |
| 26 | 2404 | 306.42 |
| 29 | 1359 | 250.85 |
| 39 | 1778 | 478.20 |
| 31 | 1934 | 600.05 |
| 32 | 1582 | 608.10 |
| 33 | 850 | 417.75 |
| 36 | 581 | 263.23 |
| 37 | 1880 | 661.38 |
| 38 | 558 | 365.34 |
| 39 | 1580 | 2131.02 |
| 40 | 142 | 19.37 |
| 41 | 398 | 33.04 |
| 42 | 1214 | 532.80 |
| 43 | 3776 | 1429.12 |
| 46 | 1178 | 624.04 |
| 47 | 297 | 132.99 |
| 48 | 929 | 115.51 |

Working Example 3

Evaluation of Stability of the Oligonucleic Acids in Monkey Serum

Preparation of Samples

A monkey serum was obtained by centrifuging (3000 rpm, 15 min) blood derived from *Macaca fascicularis* which has tested negative for B virus (The blood was purchased from Shin Nippon Biomedical Laboratories, LTD). The oligonucleic acids (13.4 ng/μl) were incubated in 50% monkey serum at 37 degrees using water bath. The samples were treated at 42 degrees for 1.5 hour using 0.3 mg/ml Proteinase K. Then, an equal volume of phenol/chloroform was added. After centrifugation (1000 rpm, 5 min), the water layer was collected as a sample for analysis by SDS-PAGE.

Performing the SDS-PAGE

The sample obtained above (100.5 ng) was loaded onto 20% SDS-polyacrylamide gel. The SDS-PAGE was performed at 20 mA for 120 min. Then, the gel was stained for 40 min using SYBR-Gold solution diluted 1000 times. The oligonucleotides were visualized as fluorescence bands using UV transilluminator. The fluorescence intensity of each band was measured using an image analyzer (IMAGE STATION: Koda).

The results are shown in FIG. 1-3 and Table 3. FIG. 1 is a photo of the gel electrophoresis as a substitute for a diagram, illustrating the stability of the S-form and R-form oligonucleic acids of SEQ No: 27-28 in the serum. FIG. 2 is a photo of the gel electrophoresis as a substitute for a diagram, illustrating the stability of the S-form and R-form oligonucleic acids of SEQ No: 43-45 in the serum. FIG. 3 is a photo of the gel electrophoresis as a substitute for a diagram, illustrating the stability of the S-form and R-form oligonucleic acids of SEQ No: 33-35 in the serum.

TABLE 3

Evaluation of stability in serum

| SEQ No. | Serum (%) | Time (min) | Residual ratio (%) Sp | Rp |
|---|---|---|---|---|
| 13, 14 | 30 | 120 | 46.1 | 33.5 |
| 27, 28 | 50 | 120 | 41.8 | 27.5 |
| 44, 45 | 50 | 180 | 73.3 | 17.2 |
| 34, 35 | 50 | 180 | 51.7 | 19.7 |

Working Example 4

Induction Test of the Production of Antigen-Specific Antibodies in Mice

Administration of the Test Substance

OVA (Wako) and oligonucleic acids which were prepared in a concentration of 0.2 mg/ml respectively using physiological saline were used as the test substance administration solution.

Preparation of Samples 8-week-old BALB/cAnCrlCrlj mouse were used in the experiment. Using general anesthesia equipment, mouse were anesthetized by isoflurane (2.0%-4.0%, Forane, Abbott Japan Co., LTD.), and maintained anesthesia. After the back of the mouse were shaved, the test substance administration solution was administered subcutaneously at 50 μl/body of dose using a disposable syringe and needle. After two weeks of the first administration, the test substance administration solution was administered again. One week later, mice were euthanized, and spleen and whole blood were collected.

Measurement of the Antibody Titer

The plasma obtained from the blood collected from the mouse 5 days before and 16 days after administration was used as samples for analysis. Solid-phasing solution was put into holes of the plate for ELISA at 0.1 ml/well. The plate was sealed, and placed overnight in a refrigerator. Then, the solution was removed and wash solution was put into wells of the plate at 0.3 ml/well, and the solution was removed. Same operation was repeated twice. In other word, the well was washed three times in total. Then, the blocking solution was put into wells of the plate at 0.2 ml/well. The plate was sealed, and placed at room temperature for 1-4 hours. Then, the solution was removed, and the well was washed three times in the same manner as described above.

The sample (plasma) for measuring was diluted to 1000 times using a solution for dilution. Next, the sample was diluted 7 or more times with common rate 2 (As a result of this process, the sample diluted 100-12800 times were obtained.). The samples were put into wells of the plate for ELISA at 0.1 ml/well. As a blank, the solution for dilution was put into another one well. The plate was sealed, and incubated for 1 hour at 37 degrees in the plate incubator. After the incubation, the solution was removed. The well was washed three times in the same manner as described above. The detection antibody solution was put into wells at 0.1 ml/well. The plate was sealed, and incubated for 1 hour at 37 degrees in the plate incubator. After the incubation, the solution was removed. The well was washed four times in the same manner as described above.

Coloring solution was put into well at 0.1 ml/well. The plate was incubated for 30 min at room temperature. Then, the stop solution was added at 0.1 ml/well in order to stop the reaction. Absorbance of each well was measured using absorption spectrometer for multi-plate (Dominant wavelength was 450 nm, Vice wavelength was 620 nm).

The result was shown in Table 4. Table 4 indicates the result of the measurement of anti-OVA-IgG titer of SEQ No: 27-28. Table 4 indicates that S-form oligonucleic acids cause higher antibody titers than R-form oligonucleic acids.

TABLE 4

The effect on the anti-OVA antibody titer of chiral CpG olignonucleic acids

| Group | IgG titer |
|---|---|
| OVA only | 100 |
| SEQ No. 27 | 1000 |
| SEQ No. 28 | 433 |

Measurement of the Weight of Spleen

The obtained spleen was washed with cold physiological saline. The weight of the spleen was measured using an electronic balance (HR-200, A&D Company, Limited).

The result was shown in Table 5. Table 5 indicates the effect on spleen weight of the oligonucleic acids of SEC ID No. 27-28. Table 5 indicates that the weight of spleen was increased in the mouse treated with R-form oligonucleic acids. This result indicates that R-form oligonucleic acids have toxicity. On the other hand, the weight of the spleen was not increased in the mouse treated with S-form oligonucleic acids. This indicates that S-form oligonucleic acids have no toxicity or have low toxicity.

TABLE 5

Effect on spleen weight of chiral CpG oligunucleic acids

| Group | Spleen mg/100 gBW | SE |
|---|---|---|
| OVA only | 570.4 | 9.6 |
| SEQ No. 27 | 566.7 | 8.2 |
| SEQ No. 28 | 607.2 | 7.6 |

Working Example 5

The CpG oligonucleic acids of which the three-dimensional structure is modified were synthesized in the same manner as described in embodiment 1. The sequences of the synthesized oligonucleic acids were shown in Table 6. The notation in the table is the same as one described in Embodiment 1. In addition, for reference, a known nucleic acid sequence is shown in SEQ No. 119.

TABLE 6

The oligonucleic acids obtained in Embodiment 5

| | |
|---|---|
| 49 | T*C*ATCGAT*T*T*ATCGAT*T*T*A*A*C*G*G*G |
| 50 | T*C*GACGTTTTGACGTT*T*T*G*A*C*G*G*G |
| 51 | T*C*GACGTTTTGACGTTTT*G*A*C*G*G*G |
| 52 | T*C*GACGT*T*GACGT*T*GACGG*G |
| 53 | TC*GACGT*T*GACGT*T*GACG*G*G |
| 54 | T*C*GACGT*T*GACGT*T*GACGG*G*G |
| 55 | T*C*GACGT*T*GACGT*T*GACT*G |

TABLE 6-continued

The oligonucleic acids obtained in Embodiment 5

| | |
|---|---|
| 56 | T*C*GACGT*T*GACGT*T*G*A*C*G*G*G |
| 57 | T*C*GACGTTGACGT*T*G*A*C*G*G*G |
| 58 | T*C*ATCGATATCGA*T*G*A*C*G*G*G |
| 59 | T*C*GACGT*T*GACGT*T*GACG*G*G*G |
| 60 | T*C*GACGTT*T*T*GACGTT*T*T*G*G*G*G*G |
| 61 | T*C*GACGTT*T*T*GACGTT*T*T*G*A*G*G*G |
| 62 | T*C*GACGTT*T*T*GACGTT*T*T*G*T*G*G*G |
| 63 | T*C*G*ACGTT*G*ACGTT*G*A*C*G*G*G |
| 64 | C*C*GACGTT*T*T*GACGTT*T*T*GACG*G*G |
| 65 | T*C*GACGTT*T*A*GACGTT*T*A*GACG*G*G |
| 66 | T*C*GACGTT*T*T*GACGTT*T*T*GACG*A*A |
| 67 | T*C*GACGTT*T*T*GACGTT*T*T*GACG*T*T |
| 68 | T*C*AACGTT*T*T*AACGTT*T*T*GACG*G*G |
| 69 | T*C*GACGTT*T*T*GACGTT*T*T*GGG |
| 70 | T*C*GACGTT*T*T*GACGTT*T*T*GACGTTGG |
| 71 | T*C*GACGTT*GACGTT*G*G*G |
| 72 | T*C*GACGTT*T*T*T*ACGTT*T*T*G*ACG*G*G |
| 73 | T*C*G*A*CGTT*T*T*ACGTTTGACGGG |
| 74 | T*C*G*ACGTT*T*T*G*ACGTT*T*T*G*ACG*G*G |
| 75 | T*C*GACGTA*GACGTA*GACG*G*G |
| 76 | T*A*GACGAT*T*C*GTCGTC*T*A*GACG*G*G |
| 77 | T*A*GACGA*C*GTCGT*A*GACC*G*G |
| 78 | T*C*G*ACGTTT*T*G*ACGTT*T*T*G*A*C*G*G*G |
| 79 | T*C*G*ACGTT*T*T*T*A*ACGAC*T*T*G*A*C*G*G*G |
| 80 | T*C*G*ACGTTT*T*AACGAC*T*T*G*A*C*G*G*G |
| 81 | T*C*ATCGAT*T*T*ATCGAT*T*T*GACG*G*G |
| 82 | T*C*ATCGAT*T*T*ATCGAT*T*T*ATCGA*T*G*G*G |
| 83 | T*C*ATCGAT*T*T*ATCGAT*T*T*AT*C*G*G*G |
| 84 | T*C*ATCGAT*T*T*ATCGAT*T*T*ATCGAT*T*T*ATCG*G*G |
| 85 | T*C*ATCGAT*T*T*ATCGAT*T*T*ATCGAT*T*T*A*T*C*G*G*G |
| 86 | T*C*ATCGAT*T*T*ATCGAT*T*T*ATCGAT*A*T*C*G*G*G |
| 87 | T*T*ATCGAT*T*T*ATCGAT*T*T*G*A*C*G*G*G |
| 88 | T*C*ATCGATATCGAT*T*T*G*A*C*G*G*G |
| 89 | TCATCGAT*T*T*ATCGAT*T*T*A*T*C*G*G*G |
| 90 | T*C*ATCGAT*T*T*ATCGAT*T*T*G*A*C*G*A*T |
| 91 | T*C*GACGT*T*GACGT*T*GACGT*T*G*G*G |
| 92 | T*C*G*ACGTT*T*G*ACGTT*T*G*A*C*G*G*G |
| 93 | T*C*A*TCGAT*T*T*A*TCGAT*T*T*G*A*C*G*G*G |
| 94 | T*C*A*TCGAT*A*TCGAT*G*ACGT*T*T*G*G*G |
| 95 | T*C*GACGTTTGACGTTT*G*A*C*G*G*G |
| 96 | T*C*ATCGAT*T*T*ATCGAT*T*T*A*T*C*G*G*G |
| 97 | G*G*GACGATATCGTCG*G*G*G*G*G |
| 98 | G*G*GACGAC*G*TCGTCG*G*G*G*G*G |
| 99 | G*G*GACGACGTCGTCG*G*G*G*G |
| 100 | T*C*GACGACGTCGTCG*G*G*G*G*G |
| 101 | T*C*GACGACGTCGTCT*T*T*G*G*G |
| 102 | T*A*GACGACGTCGTCT*T*T*G*G*G |
| 103 | T*T*GACGACGTCGTCA*A*A*G*G*G |
| 104 | T*C*GACGTAGACGTCT*T*T*G*G*G |
| 105 | T*C*GACGTAGACGTTT*A*G*G*G*G |
| 106 | T*C*ATCGATATCGATT*T*T*G*G*G |
| 107 | T*T*ATCGATATCGATA*A*A*G*G*G |
| 108 | T*C*GACGTAGACGATCGA*T*G*G*G |
| 109 | T*C*GACGAC*T*T*GACGAC*T*T*G*A*C*G*G*G |
| 110 | T*C*GACGAC*T*T*GTCGTC*T*T*G*A*C*G*G*G |
| 111 | T*T*ATCGATATCGATA*T*C*G*A*T*G*G*G |
| 112 | T*T*ATCGATATCGATT*T*A*A*A*G*G*G |
| 113 | T*C*ATCGAT*T*T*ATCGAT*T*T*G*A*C*G*T*T |
| 114 | T*C*ATCGA*T*ATCGA*T*G*A*C*G*G*G*G |
| 115 | T*C*ATCGAT*ATCGA*T*G*G*G |
| 116 | T*C*GTCGTTGTCGT*T*G*A*C*G*G*G |
| 117 | T*C*G*TCGTT*T*T*G*TCGTT*T*T*G*A*C*G*G*G |
| 118 | T*C*GTCGTTGTCGTTG*A*C*G*A*C*G*G*G |
| 119 | T*C*G*T*C*G*T*T*T*T*G*T*C*G*T*T*T*T*G*T*C*G*T*T |

Working Example 6

Using the same method as described in Embodiment 2, the induction of the production of IFN-α of the oligonucleic acids in the peripheral blood mononuclear cells (PBMC) was investigated. The values in the table show the relative values compared to the value of the nucleic acid of SEQ No. 128. The result was indicated in Table 7.

TABLE 7

Inductive effect of production of INF-α
in simian peripheral blood mononuclear cells

| No. | Sequence (*indicates the S-form modifictaion) | Ratio 195 | ±SE | Number of individuals |
|---|---|---|---|---|
| 49 | T*C*ATCGAT*T*T*ATCGAT*T*T*A*A*C*G*G*G | 195 | 40 | 4 |
| 50 | T*C*GACGTTTTGACGTT*T*T*G*A*C*G*G*G | 241 | 32 | 4 |
| 51 | T*C*GACGTTTTGACGTTTT*G*A*C*G*G*G | 265 | 52 | 3 |
| 52 | T*C*GACGT*T*GACGT*T*GACGG*G | 297 | 71 | 3 |
| 53 | TC*GACGT*T*GACGT*T*GACG*G*G | 361 | 60 | 5 |
| 54 | T*C*GACGT*T*GACGT*T*GACGG*G*G | 225 | 101 | 3 |
| 55 | T*C*GACGT*T*GACGT*T*GACT*G | 124 | 39 | 4 |
| 56 | T*C*GACGT*T*GACGT*T*G*A*C*G*G*G | 210 | 59 | 6 |
| 57 | T*C*GACGTTGACGT*T*G*A*C*G*G*G | 269 | 71 | 3 |
| 58 | T*C*ATCGATATCGA*T*G*A*C*G*G*G | 255 | 42 | 4 |
| 59 | T*C*GACGT*T*GACGT*T*GACG*G*G*G | 139 | 23 | 4 |
| 60 | T*C*GACGTT*T*T*GACGTT*T*T*G*G*G*G | 123 | 38 | 5 |
| 61 | T*C*GACGTT*T*T*GACGTT*T*T*G*A*G*G*G | 123 | 30 | 5 |
| 62 | T*C*GACGTT*T*T*GACGTT*T*T*G*T*G*G*G | 117 | 17 | 5 |
| 63 | T*C*G*ACGTT*G*ACGTT*G*A*C*G*G*G | 155 | 29 | 3 |
| 64 | C*C*GACGTT*T*T*GACGTT*T*T*GACG*G*G | 84 | 36 | 4 |
| 65 | T*C*GACGTT*T*A*GACGTT*T*A*GACG*G*G | 246 | 20 | 4 |
| 66 | T*C*GACGTT*T*T*GACGTT*T*T*GACG*A*A | 188 | 56 | 5 |
| 67 | T*C*GACGTT*T*T*GACGTT*T*T*GACG*T*T | 244 | 93 | 5 |
| 68 | T*C*AACGTT*T*T*AACGTT*T*T*GACG*G*G | 220 | 97 | 5 |
| 69 | T*C*GACGTT*T*T*GACGTT*T*T*GGG | 98 | 44 | 5 |
| 70 | T*C*GACGTT*T*T*GACGTT*T*T*GACGTTGG | 242 | 80 | 4 |
| 71 | T*C*GACGTT*GACGTT*G*G*G | 238 | 48 | 3 |
| 72 | T*C*GACGTT*T*T*T*ACGTT*T*T*G*ACG*G*G | 225 | 76 | 3 |
| 73 | T*C*G*A*CGTT*T*T*ACGTTTTGACGGG | 102 | 22 | 3 |
| 74 | T*C*G*ACGTT*T*T*G*ACGTT*T*T*G*ACG*G*G | 247 | 120 | 5 |
| 75 | T*C*GACGTA*GACGTA*GACG*G*G | 188 | 54 | 4 |
| 76 | T*A*GACGAT*T*C*GTCGTC*T*A*GACG*G*G | 260 | 49 | 3 |
| 77 | T*A*GACGA*C*GTCGT*A*GACC*G*G | 86 | 17 | 4 |
| 78 | T*C*G*ACGTTT*T*G*ACGTT*T*T*G*A*C*G*G*G | 98 | 6 | 3 |
| 79 | T*C*G*ACGTT*T*T*T*A*ACGAC*T*T*G*A*C*G*G*G | 142 | 26 | 3 |
| 80 | T*C*G*ACGTTT*T*AACGAC*T*T*G*A*C*G*G*G | 223 | 22 | 3 |
| 81 | T*C*ATCGAT*T*T*ATCGAT*T*T*GACG*G*G | 389 | 163 | 3 |
| 82 | T*C*ATCGAT*T*T*ATCGAT*T*T*ATCGA*T*G*G*G | 363 | 38 | 4 |
| 83 | T*C*ATCGAT*T*T*ATCGAT*T*T*AT*C*G*G*G | 308 | 53 | 4 |
| 84 | T*C*ATCGAT*T*T*ATCGAT*T*T*ATCGAT*T*T*ATCG*G*G | 334 | 40 | 3 |

TABLE 7-continued

Inductive effect of production of INF-α
in simian peripheral blood mononuclear cells

| No. | Sequence (*indicates the S-form modifictaion) | Ratio 195 | ±SE | Number of individuals |
|---|---|---|---|---|
| 85 | T*C*ATCGAT*T*T*ATCGAT*T*T*ATCGAT*T*T*A*T*C*G*G*G | 170 | 21 | 4 |
| 86 | T*C*ATCGAT*T*T*ATCGAT*T*T*ATCGAT*A*T*C*G*G*G | 170 | 25 | 4 |
| 87 | T*T*ATCGAT*T*T*ATCGAT*T*T*G*A*C*G*G*G | 208 | 86 | 3 |
| 88 | T*C*ATCGATATCGAT*T*T*G*A*C*G*G*G | 288 | 135 | 3 |
| 89 | TCATCGAT*T*T*ATCGAT*T*T*A*T*C*G*G*G | 279 | 45 | 3 |
| 90 | T*C*ATCGAT*T*T*ATCGAT*T*T*G*A*C*G*A*T | 374 | 205 | 3 |
| 91 | T*C*GACGT*T*GACGT*T*GACGT*T*G*G*G | 135 | 41 | 5 |
| 92 | T*C*G*ACGT*T*G*ACGT*T*G*A*C*G*G*G | 97 | 25 | 3 |
| 93 | T*C*A*TCGAT*T*T*A*TCGAT*T*T*G*A*C*G*G*G | 109 | 34 | 3 |
| 94 | T*C*A*TCGAT*A*TCGAT*G*ACGT*T*T*G*G*G | 103 | 7 | 2 |
| 95 | T*C*GACGTTTGACGTTT*G*A*C*G*G*G | 222 | 37 | 4 |
| 96 | T*C*ATCGAT*T*T*ATCGAT*T*T*A*T*C*G*G*G | 129 | 35 | 3 |
| 97 | G*G*GACGATATCGTCG*G*G*G*G*G | 167 | 11 | 5 |
| 98 | G*G*GACGAC*G*TCGTCG*G*G*G*G*G | 138 | 107 | 3 |
| 99 | G*G*GACGACGTCGTCG*G*G*G*G | 230 | 87 | 4 |
| 100 | T*C*GACGACGTCGTCG*G*G*G*G*G | 125 | 53 | 3 |
| 101 | T*C*GACGACGTCGTCT*T*T*G*G*G | 404 | 52 | 3 |
| 102 | T*A*GACGACGTCGTCT*T*T*G*G*G | 387 | 126 | 3 |
| 103 | T*T*GACGACGTCGTCA*A*A*G*G*G | 302 | 64 | 5 |
| 104 | T*C*GACGTAGACGTCT*T*T*G*G*G | 354 | 75 | 4 |
| 105 | T*C*GACGTAGACGTTT*A*G*G*G*G | 297 | 65 | 4 |
| 106 | T*C*ATCGATATCGATT*T*T*G*G*G | 224 | 26 | 4 |
| 107 | T*T*ATCGATATCGATA*A*A*G*G*G | 154 | 61 | 6 |
| 108 | T*C*GACGTAGACGATCGA*T*G*G*G | 370 | 70 | 4 |
| 109 | T*C*GACGAC*T*T*GACGAC*T*T*G*A*C*G*G*G | 235 | 76 | 3 |
| 110 | T*C*GACGAC*T*T*GTCGTC*T*T*G*A*C*G*G*G | 133 | 42 | 4 |
| 111 | T*T*ATCGATATCGATA*T*C*G*A*T*G*G*G | 200 | 8 | 4 |
| 112 | T*T*ATCGATATCGATT*T*A*A*A*G*G*G | 257 | 40 | 4 |
| 113 | T*C*ATCGAT*T*T*ATCGAT*T*T*G*A*C*G*T*T | 209 | 27 | 4 |
| 114 | T*C*ATCGA*T*ATCGA*T*G*A*C*G*G*G | 155 | 37 | 3 |
| 115 | T*C*ATCGAT*ATCGA*T*G*G*G | 95 | 12 | 2 |
| 116 | T*C*GTCGTTGTCGT*T*G*A*C*G*G*G | 235 | 23 | 4 |
| 117 | T*C*G*TCGTT*T*T*G*TCGTT*T*T*G*A*C*G*G*G | 177 | 61 | 4 |
| 118 | T*C*GTCGTTGTCGTTG*A*C*G*A*C*G*G*G | 88 | 14 | 4 |
| 119 | T*C*G*T*C*G*T*T*T*T*G*T*C*G*T*T*T*T*G*T*C*G*T*T | 100 | 0 | 41 |

Using the same method as described in Embodiment 2, the concentration of IFN-α in case of administering the oligonucleic acids of SEQ No. 119 was measured. The result was shown in Table 8.

TABLE 8

| Concentration of IFN-α IFN-alfa (ng/mL) | | |
|---|---|---|
| 52.2 | 6.2 | Measured value |

INDUSTRIAL APPLICABILITY

The present invention can be utilized in the field of pharmaceutical industry.

The invention claimed is:

1. An oligonucleotide which comprises two to four sequences each represented by 5'-$X_1X_2$CpG$X_3X_4$-3' and has a length of 14 to 32 nucleotides, wherein the CpG is non-methylated CpG without a modified phosphate backbone, wherein $X_1X_2$ is AA, AT, GA, or GT, and contains no modified phosphate backbones, wherein $X_3X_4$ is TT, AT, AC, TC, or CG, and contains no modified phosphate backbones, and the oligonucleotide comprises at least one modified phosphate backbone at a site other than the parts represented by 5'-$X_1X_2$CpG$X_3X_4$-3'.

2. An oligonucleotide which comprises two to four sequences each represented by 5'-$X_1X_2$CpG$X_3X_4$-3' and has a length of 14 to 32 nucleotides, wherein the CpG is non-methylated CpG without a modified phosphate backbone, wherein $X_1X_2$ is AA, AT, GA, or GT, and may comprise a modified phosphate backbone, wherein X₃X₄ is TT, AT, AC, TA, TC, or CG, and may comprise a modified phosphate backbone, and wherein the oligonucleotide comprises at least one Sp modified phosphate backbone at a site other than the parts represented by 5'-X₁X₂CpGX₃X₄-3'.

3. An oligonucleotide which comprises two to four sequences each represented by 5'-X₁X₂CpGX₃X₄-3' and has a length of 14 to 32 nucleotides, wherein the CpG is non-methylated CpG without a modified phosphate backbone, wherein X₁X₂ is AA, AT, GA, or GT, and may comprise a modified phosphate backbone, wherein X₃X₄ is TT, AT, AC, TA, TC, or CG, and may comprise a modified phosphate backbone, and the oligonucleotide comprises at least one modified phosphate backbone at a site other than the parts represented by 5'-X₁X₂CpGX₃X₄-3'; and wherein the oligonucleotide comprises one of the following sequences:

| SEQ No. | Sequence |
|---|---|
| 1 | T*C*GTCGTT*T*T*GTCGTT*T*T*GTCGGG |
| 2 | G*G*GTCGTT*T*T*GTCGTT*T*T*GTCGGG |
| 3 | T*C*AACGTT*T*C*AACGTT*T*T |
| 4 | T*C*AACGTT*T*C*AACGTT*T*T*GG |
| 5 | T*C*AACGTT*T*C*AACGTT*G*G |
| 6 | T*C*AACGTT*T*C*AACGTT*G*G*G*G |
| 7 | T*C*AACGTT*T*T*AACGTT*T*T*AACGGG |
| 8 | T*C*AACGTT*T*A*ACGTT*T*T |
| 9 | T*C*AACGT*TAACGTT*T*T |
| 10 | T*C*AACGTT*T*A*AACGTT*T*A*AACGGG |
| 11 | T*C*AACGTTAACGTTAACGGG |
| 12 | T*C*GACGTT*T*T*GACGTT*T*T*GACGGG |
| 15 | G*G*GACGTT*T*T*TGACGT*T*T*TGACGGGGG |
| 16 | T*C*GACGT*T*T*TGACGT*T*T*TGACGT*T*T*TGACGGG |
| 17 | T*C*GACGT*T*GACGT*T*GACGGG |
| 20 | T*C*GACGT*T*GACGT*T*GACGT*T*GACGGG |
| 21 | T*C*GACGTT*T*A*AACGTT*T*A*AACGTT*T*A*AACGGG |
| 22 | T*C*GACGTT*T*A*AACGTT*T*A*GACGTT*T*A*AACGGG |
| 23 | T*C*GACGTTAACGTTAACGTTAACGGG |
| 24 | GGGACGTT*T*A*AACGTCTAGACGGG |
| 25 | T*C*GACGT*ACGT*ACGT*ACGGG |
| 26 | T*C*GACGTT*T*T*GACGTT*T*T*G*A*C*G*G |
| 29 | T*C*GACGTT*T*T*GACGTT*T*T*GACGG*G*G |
| 30 | T*C*GACGTT*T*T*GACGTT*T*T*GACGT*G*G |
| 31 | T*C*GACGTT*T*T*GACGTT*T*T*GACGTG*G*G |
| 32 | T*C*GACGTT*T*T*GACGTT*T*T*G*A*C*G*G*G |
| 33 | T*C*GACGTT*T*T*GACGTT*T*T*GACGG*G*G*G |
| 36 | T*C*GACGTT*T*T*GACGTT*T*T*GACG*G*G*G*G |
| 37 | T*C*GACGT*T*GACGT*T*GACGTG*G*G |
| 38 | G*G*T*G*C*ATCGAT*G*C*A*G*G*G*G*G |
| 39 | T*C*ATCGAT*T*T*ATCGAT*T*T*ATCGGG |
| 40 | G*G*T*G*C*GACGAT*G*C*A*G*G*G*G*G |
| 41 | G*G*G*G*GACGATCGTCGGG*G*G*G |
| 42 | G*G*GACGATATCGTCG*G*G*G*G |
| 43 | G*G*GACGACGTCGTCG*G*G*G*G |
| 46 | G*G*GGGACGATCGTCG*G*G*G*G |
| 47 | G*G*GACGCGCGTCG*G*G*G*G*G |
| 48 | G*G*G*G*TCGTTCG*G*G*G |
| 49 | T*C*ATCGAT*T*T*ATCGAT*T*T*A*A*C*G*G*G |
| 50 | T*C*GACGTTTTGACGTT*T*T*G*A*C*G*G*G |
| 51 | T*C*GACGTTTTGACGTTTT*G*A*C*G*G*G |
| 52 | T*C*GACGT*T*GACGT*T*GACGG*G |
| 53 | TC*GACGT*T*GACGT*T*GACG*G*G |
| 54 | T*C*GACGT*T*GACGT*T*GACGG*G*G |
| 55 | T*C*GACGT*T*GACGT*T*GACT*G |
| 56 | T*C*GACGT*T*GACGT*T*G*A*C*G*G |
| 57 | T*C*GACGTTGACGT*T*G*A*C*G*G |
| 58 | T*C*ATCGATATCGA*T*G*A*C*G*G |
| 59 | T*C*GACGT*T*GACGT*T*GACG*G*G*G |
| 60 | T*C*GACGTT*T*T*GACGTT*T*T*G*G*G*G |
| 61 | T*C*GACGTT*T*T*GACGTT*T*T*G*A*G*G*G |
| 62 | T*C*GACGTT*T*T*GACGTT*T*T*G*T*G*G*G |
| 63 | T*C*G*ACGTT*G*ACGTT*G*A*C*G*G*G |
| 64 | C*C*GACGTT*T*T*GACGTT*T*T*GACG*G*G |
| 65 | T*C*GACGTT*T*A*GACGTT*T*A*GACG*G*G |
| 66 | T*C*GACGTT*T*T*GACGTT*T*T*GACG*A*A |
| 67 | T*C*GACGTT*T*T*GACGTT*T*T*GACG*T*T |
| 68 | T*C*AACGTT*T*T*AACGTT*T*T*GACG*G*G |
| 69 | T*C*GACGTT*T*T*GACGTT*T*T*GGG |
| 70 | T*C*GACGTT*T*T*GACGTT*T*T*GACGTTGG |
| 71 | T*C*GACGTT*GACGTT*G*G*G |
| 72 | T*C*GACGTT*T*T*T*ACGTT*T*T*G*ACG*G*G |
| 73 | T*C*G*A*CGTT*T*T*ACGTTTGACGGG |
| 74 | T*C*G*ACGTT*T*T*G*ACGTT*T*T*G*ACG*G*G |
| 75 | T*C*GACGTA*GACGTA*GACG*G*G |
| 76 | T*A*GACGAT*T*C*GTCGTC*T*A*GACG*G*G |

| SEQ No. | Sequence |
|---|---|
| 77 | T*A*GACGA*C*GTCGT*A*GACC*G*G |
| 78 | T*C*G*ACGTTT*T*G*ACGTT*T*T*G*A*C*G*G |
| 79 | T*C*G*ACGTT*T*T*T*A*ACGAC*T*T*G*A*C*G*G |
| 80 | T*C*G*ACGTTT*T*AACGAC*T*T*G*A*C*G*G |
| 81 | T*C*ATCGAT*T*T*ATCGAT*T*T*GACG*G*G |
| 82 | T*C*ATCGAT*T*T*ATCGAT*T*T*ATCGA*T*G*G*G |
| 83 | T*C*ATCGAT*T*T*ATCGAT*T*T*AT*C*G*G*G |
| 84 | T*C*ATCGAT*T*T*ATCGAT*T*T*ATCGAT*T*T*ATCG*G*G |
| 85 | T*C*ATCGAT*T*T*ATCGAT*T*T*ATCGAT*T*T*A*T*C*G*G*G |
| 86 | T*C*ATCGAT*T*T*ATCGAT*T*T*ATCGAT*A*T*C*G*G*G |
| 87 | T*T*ATCGAT*T*T*ATCGAT*T*T*G*A*C*G*G*G |
| 88 | T*C*ATCGATATCGAT*T*T*G*A*C*G*G*G |
| 89 | TCATCGAT*T*T*ATCGAT*T*T*A*T*C*G*G*G |
| 90 | T*C*ATCGAT*T*T*ATCGAT*T*T*G*A*C*G*A*T |
| 91 | T*C*GACGT*T*GACGT*T*GACGT*T*G*G*G |
| 92 | T*C*G*ACGT*T*G*ACGT*T*G*A*C*G*G*G |
| 93 | T*C*A*TCGAT*T*T*A*TCGAT*T*T*G*A*C*G*G*G |
| 94 | T*C*A*TCGAT*A*TCGAT*G*ACGT*T*T*G*G*G |
| 95 | T*C*GACGTTTGACGTTT*G*A*C*G*G*G |
| 96 | T*C*ATCGAT*T*T*ATCGAT*T*T*A*T*C*G*G*G |
| 97 | G*G*GACGATATCGTCG*G*G*G*G*G |
| 98 | G*G*GACGAC*G*TCGTCG*G*G*G*G*G |
| 99 | G*G*GACGACGTCGTCG*G*G*G*G |
| 100 | T*C*GACGACGTCGTCG*G*G*G*G*G |
| 101 | T*C*GACGACGTCGTCT*T*T*G*G*G |
| 102 | T*A*GACGACGTCGTCT*T*T*G*G*G |
| 103 | T*T*GACGACGTCGTCA*A*A*G*G*G |
| 104 | T*C*GACGTAGACGTCT*T*T*G*G*G |
| 105 | T*C*GACGTAGACGTTT*A*G*G*G*G |
| 106 | T*C*ATCGATATCGATT*T*T*G*G*G |
| 107 | T*T*ATCGATATCGATA*A*A*G*G*G |
| 108 | T*C*GACGTAGACGATCGA*T*G*G*G |
| 109 | T*C*GACGAC*T*T*GACGAC*T*T*G*A*C*G*G*G |
| 110 | T*C*GACGAC*T*T*GTCGTC*T*T*G*A*C*G*G*G |
| 111 | T*T*ATCGATATCGATA*T*C*G*A*T*G*G*G |
| 112 | T*T*ATCGATATCGATT*T*A*A*A*G*G*G |
| 113 | T*C*ATCGAT*T*T*ATCGAT*T*T*G*A*C*G*T*T |
| 114 | T*C*ATCGA*T*ATCGA*T*G*A*C*G*G*G*G |
| 115 | T*C*ATCGAT*ATCGA*T*G*G*G |
| 116 | T*C*GTCGTTGTCGT*T*G*A*C*G*G*G |
| 117 | T*C*G*TCGTT*T*T*G*TCGTT*T*T*G*A*C*G*G*G |
| 118 | T*C*GTCGTTGTCGTTG*A*C*G*A*C*G*G*G | wherein in the above formula, * refers to a modified phosphate backbone and at least one * in each formula is Sp, and in the above formula, CG at a site corresponding to 5'-$X_1X_2$CpG$X_3X_4$-3' means non-methylated CpG without a modified phosphate backbone.

4. An oligonucleotide which comprises two to four sequences each represented by 5'-$X_1X_2$CpG$X_3X_4$-3' and has a length of 14 to 32 nucleotides,
   wherein the CpG is non-methylated CpG without a modified phosphate backbone,
   wherein $X_1X_2$ is AA, AT, GA, or GT, and may comprise a modified phosphate backbone,
   wherein $X_3X_4$ is TT, AT, AC, TA, TC, or CG, and may comprise a modified phosphate backbone,
   wherein the oligonucleotide comprises at least one modified phosphate backbone at a site other than the parts represented by 5'-$X_1X_2$CpG$X_3X_4$-3', and
   wherein the oligonucleotide comprises a sequence represented as -$(G)_m$-, wherein m is an integer of 1 to 6, at 3' end side of a CpG motif, the CpG motif being 5'-$X_1X_2$CpG$X_3X_4$-3'.

5. An oligonucleotide which comprises two to four sequences each represented by 5'-$X_1X_2$CpG$X_3X_4$-3' and has a length of 14 to 32 nucleotides,
   wherein the CpG is non-methylated CpG without a modified phosphate backbone,
   wherein $X_1X_2$ is AA, AT, GA, or GT, and may comprise a modified phosphate backbone,
   wherein $X_3X_4$ is TT, AT, AC, TA, TC, or CG, and may comprise a modified phosphate backbone,
   wherein the oligonucleotide comprises at least one modified phosphate backbone at a site other than the parts represented by 5'-$X_1X_2$CpG$X_3X_4$-3', and
   wherein the oligonucleotide comprises a sequence represented as TC, TA, TG, CC or CC at 5' end side of a CpG motif, the CpG motif being the sequence of 5'-$X_1X_2$CpG$X_3X_4$-3'.

6. An oligonucleotide which comprises two to four sequences each represented by 5'-$X_1X_2$CpG$X_3X_4$-3' and has a length of 14 to 32 nucleotides,
   wherein the CpG is non-methylated CpG without a modified phosphate backbone,
   wherein $X_1X_2$ is AA, AT, GA, or GT, and may comprise a modified phosphate backbone,
   wherein $X_3X_4$ is TT, AT, AC, TA, TC, or CG, and may comprise a modified phosphate backbone,
   wherein the oligonucleotide comprises at least one modified phosphate backbone at a site other than the parts represented by 5'-$X_1X_2$CpG$X_3X_4$-3', and
   wherein the oligonucleotide comprises at least a first CpG motif and a second CpG motif, the first and the second CpG motifs being 5'-$X_1X_2$CpG$X_3X_4$-3', wherein the first CpG motif and the second CpG motif are bonded directly with no sequence between them, or wherein the oligonucleotide comprises a sequence represented as $-(T)_n-$, wherein n is an integer of 1 to 3, TA or TC between the first CpG motif and the second CpG motif.

7. The oligonucleotide as claimed in claim 3, wherein the oligonucleotide comprises a sequence selected from Sequence Nos. 12, 17, 78, 43, 60, 67, 102, 103, 112 and 116.

* * * * *

```
                         SEQUENCE LISTING

<160> NUMBER OF SEQ ID NOS: 119

<210> SEQ ID NO 1
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (8)..(11)
<223> OTHER INFORMATION: wherein all the internucleotide linkages are
      phosphorothioate linkages
<220> FEATURE:
<221> NAME/KEY: misc_feature
<222> LOCATION: (16)..(19)
<223> OTHER INFORMATION: wherein all the internucleotide linkages are
      phosphorothioate linkages

<400> SEQUENCE: 1
tcgtcgtttt gtcgttttgt cggg                                            24

<210> SEQ ID NO 2
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (8)..(11)
<223> OTHER INFORMATION: wherein all the internucleotide linkages are
      phosphorothioate linkages
<220> FEATURE:
<221> NAME/KEY: misc_feature
<222> LOCATION: (16)..(19)
<223> OTHER INFORMATION: wherein all the internucleotide linkages are
      phosphorothioate linkages

<400> SEQUENCE: 2
gggtcgtttt gtcgttttgt cggg                                            24

<210> SEQ ID NO 3
<211> LENGTH: 18
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
```

```
<221> NAME/KEY: misc_feature
<222> LOCATION: (8)..(11)
<223> OTHER INFORMATION: wherein all the internucleotide linkages are
      phosphorothioate linkages
<220> FEATURE:
<221> NAME/KEY: misc_feature
<222> LOCATION: (16)..(18)
<223> OTHER INFORMATION: wherein all the internucleotide linkages are
      phosphorothioate linkages

<400> SEQUENCE: 3
tcaacgtttc aacgtttt                                                        18

<210> SEQ ID NO 4
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (8)..(11)
<223> OTHER INFORMATION: wherein all the internucleotide linkages are
      phosphorothioate linkages
<220> FEATURE:
<221> NAME/KEY: misc_feature
<222> LOCATION: (16)..(19)
<223> OTHER INFORMATION: wherein all the internucleotide linkages are
      phosphorothioate linkages

<400> SEQUENCE: 4
tcaacgtttc aacgttttgg                                                      20

<210> SEQ ID NO 5
<211> LENGTH: 18
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (8)..(11)
<223> OTHER INFORMATION: wherein all the internucleotide linkages are
      phosphorothioate linkages
<220> FEATURE:
<221> NAME/KEY: misc_feature
<222> LOCATION: (16)..(18)
<223> OTHER INFORMATION: wherein all the internucleotide linkages are
      phosphorothioate linkages

<400> SEQUENCE: 5
tcaacgtttc aacgttgg                                                        18

<210> SEQ ID NO 6
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
```

```
          phosphorothioate linkages
<220> FEATURE:
<221> NAME/KEY: misc_feature
<222> LOCATION: (8)..(11)
<223> OTHER INFORMATION: wherein all the internucleotide linkages are
      phosphorothioate linkages
<220> FEATURE:
<221> NAME/KEY: misc_feature
<222> LOCATION: (16)..(20)
<223> OTHER INFORMATION: wherein all the internucleotide linkages are
      phosphorothioate linkages

<400> SEQUENCE: 6
tcaacgtttc aacgttgggg                                                    20

<210> SEQ ID NO 7
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (8)..(11)
<223> OTHER INFORMATION: wherein all the internucleotide linkages are
      phosphorothioate linkages
<220> FEATURE:
<221> NAME/KEY: misc_feature
<222> LOCATION: (16)..(19)
<223> OTHER INFORMATION: wherein all the internucleotide linkages are
      phosphorothioate linkages

<400> SEQUENCE: 7
tcaacgtttt aacgttttaa cggg                                               24

<210> SEQ ID NO 8
<211> LENGTH: 17
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (8)..(11)
<223> OTHER INFORMATION: wherein all the internucleotide linkages are
      phosphorothioate linkages
<220> FEATURE:
<221> NAME/KEY: misc_feature
<222> LOCATION: (15)..(17)
<223> OTHER INFORMATION: wherein all the internucleotide linkages are
      phosphorothioate linkages

<400> SEQUENCE: 8
tcaacgttta acgtttt                                                       17

<210> SEQ ID NO 9
<211> LENGTH: 16
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
```

```
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (7)..(8)
<223> OTHER INFORMATION: wherein all the internucleotide linkages are
      phosphorothioate linkages
<220> FEATURE:
<221> NAME/KEY: misc_feature
<222> LOCATION: (14)..(16)
<223> OTHER INFORMATION: wherein all the internucleotide linkages are
      phosphorothioate linkages

<400> SEQUENCE: 9
tcaacgttaa cgtttt                                                       16

<210> SEQ ID NO 10
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (8)..(11)
<223> OTHER INFORMATION: wherein all the internucleotide linkages are
      phosphorothioate linkages
<220> FEATURE:
<221> NAME/KEY: misc_feature
<222> LOCATION: (16)..(19)
<223> OTHER INFORMATION: wherein all the internucleotide linkages are
      phosphorothioate linkages

<400> SEQUENCE: 10
tcaacgttta aacgtttaaa cggg                                              24

<210> SEQ ID NO 11
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages

<400> SEQUENCE: 11
tcaacgttaa cgttaacggg                                                   20

<210> SEQ ID NO 12
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (8)..(11)
<223> OTHER INFORMATION: wherein all the internucleotide linkages are
      phosphorothioate linkages
```

```
<220> FEATURE:
<221> NAME/KEY: misc_feature
<222> LOCATION: (16)..(19)
<223> OTHER INFORMATION: wherein all the internucleotide linkages are
      phosphorothioate linkages

<400> SEQUENCE: 12
tcgacgtttt gacgttttga cggg                                                24

<210> SEQ ID NO 13
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(19)
<223> OTHER INFORMATION: wherein all the internucleotide linkages are
      phosphorothioate linkages with Sp Chirality

<400> SEQUENCE: 13
tcgacgtttt gacgttttga cggg                                                24

<210> SEQ ID NO 14
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Rp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Rp Chirality
<220> FEATURE:
<221> NAME/KEY: misc_feature
<222> LOCATION: (16)..(19)
<223> OTHER INFORMATION: wherein all the internucleotide linkages are
      phosphorothioate linkages with Rp Chirality

<400> SEQUENCE: 14
tcgacgtttt gacgttttga cggg                                                24

<210> SEQ ID NO 15
<211> LENGTH: 26
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (7)..(10)
```

<223> OTHER INFORMATION: wherein all the internucleotide linkages are
      phosphorothioate linkages
<220> FEATURE:
<221> NAME/KEY: misc_feature
<222> LOCATION: (15)..(18)
<223> OTHER INFORMATION: wherein all the internucleotide linkages are
      phosphorothioate linkages

<400> SEQUENCE: 15
gggacgtttt gacgttttga cggggg                                        26

<210> SEQ ID NO 16
<211> LENGTH: 32
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (7)..(10)
<223> OTHER INFORMATION: wherein all the internucleotide linkages are
      phosphorothioate linkages
<220> FEATURE:
<221> NAME/KEY: misc_feature
<222> LOCATION: (15)..(18)
<223> OTHER INFORMATION: wherein all the internucleotide linkages are
      phosphorothioate linkages
<220> FEATURE:
<221> NAME/KEY: misc_feature
<222> LOCATION: (23)..(26)
<223> OTHER INFORMATION: wherein all the internucleotide linkages are
      phosphorothioate linkages

<400> SEQUENCE: 16
tcgacgtttt gacgttttga cgtttgacg gg                                  32

<210> SEQ ID NO 17
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (7)..(9)
<223> OTHER INFORMATION: wherein all the internucleotide linkages are
      phosphorothioate linkages
<220> FEATURE:
<221> NAME/KEY: misc_feature
<222> LOCATION: (13)..(15)
<223> OTHER INFORMATION: wherein all the internucleotide linkages are
      phosphorothioate linkages

<400> SEQUENCE: 17
tcgacgttga cgttgacggg                                               20

<210> SEQ ID NO 18
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:

```
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (7)..(9)
<223> OTHER INFORMATION: wherein all the internucleotide linkages are
      phosphorothioate linkages with Sp Chirality
<220> FEATURE:
<221> NAME/KEY: misc_feature
<222> LOCATION: (13)..(15)
<223> OTHER INFORMATION: wherein all the internucleotide linkages are
      phosphorothioate linkages with Sp Chirality

<400> SEQUENCE: 18
tcgacgttga cgttgacggg                                                  20

<210> SEQ ID NO 19
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Rp Chirality
<220> FEATURE:
<221> NAME/KEY: misc_feature
<222> LOCATION: (7)..(9)
<223> OTHER INFORMATION: wherein all the internucleotide linkages are
      phosphorothioate linkages with Rp Chirality
<220> FEATURE:
<221> NAME/KEY: misc_feature
<222> LOCATION: (13)..(15)
<223> OTHER INFORMATION: wherein all the internucleotide linkages are
      phosphorothioate linkages with Rp Chirality

<400> SEQUENCE: 19
tcgacgttga cgttgacggg                                                  20

<210> SEQ ID NO 20
<211> LENGTH: 26
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (7)..(9)
<223> OTHER INFORMATION: wherein all the internucleotide linkages are
      phosphorothioate linkages
<220> FEATURE:
<221> NAME/KEY: misc_feature
<222> LOCATION: (13)..(15)
<223> OTHER INFORMATION: wherein all the internucleotide linkages are
      phosphorothioate linkages
<220> FEATURE:
<221> NAME/KEY: misc_feature
<222> LOCATION: (19)..(21)
<223> OTHER INFORMATION: wherein all the internucleotide linkages are
      phosphorothioate linkages

<400> SEQUENCE: 20
tcgacgttga cgttgacgtt gacggg                                           26
```

```
<210> SEQ ID NO 21
<211> LENGTH: 32
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (8)..(11)
<223> OTHER INFORMATION: wherein all the internucleotide linkages are
      phosphorothioate linkages
<220> FEATURE:
<221> NAME/KEY: misc_feature
<222> LOCATION: (16)..(19)
<223> OTHER INFORMATION: wherein all the internucleotide linkages are
      phosphorothioate linkages
<220> FEATURE:
<221> NAME/KEY: misc_feature
<222> LOCATION: (24)..(27)
<223> OTHER INFORMATION: wherein all the internucleotide linkages are
      phosphorothioate linkages

<400> SEQUENCE: 21
tcgacgttta aacgtttaaa cgtttaaacg gg                                    32

<210> SEQ ID NO 22
<211> LENGTH: 32
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (8)..(11)
<223> OTHER INFORMATION: wherein all the internucleotide linkages are
      phosphorothioate linkages
<220> FEATURE:
<221> NAME/KEY: misc_feature
<222> LOCATION: (16)..(19)
<223> OTHER INFORMATION: wherein all the internucleotide linkages are
      phosphorothioate linkages
<220> FEATURE:
<221> NAME/KEY: misc_feature
<222> LOCATION: (24)..(27)
<223> OTHER INFORMATION: wherein all the internucleotide linkages are
      phosphorothioate linkages

<400> SEQUENCE: 22
tcgacgttta aacgtttaga cgtttaaacg gg                                    32

<210> SEQ ID NO 23
<211> LENGTH: 26
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages

<400> SEQUENCE: 23
tcgacgttaa cgttaacgtt aacggg                                           26
```

<210> SEQ ID NO 24
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (8)..(11)
<223> OTHER INFORMATION: wherein all the internucleotide linkages are
      phosphorothioate linkages

<400> SEQUENCE: 24
gggacgttta aacgtctaga cggg                                              24

<210> SEQ ID NO 25
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (7)..(8)
<223> OTHER INFORMATION: wherein all the internucleotide linkages are
      phosphorothioate linkages
<220> FEATURE:
<221> NAME/KEY: misc_feature
<222> LOCATION: (11)..(12)
<223> OTHER INFORMATION: wherein all the internucleotide linkages are
      phosphorothioate linkages
<220> FEATURE:
<221> NAME/KEY: misc_feature
<222> LOCATION: (15)..(16)
<223> OTHER INFORMATION: wherein all the internucleotide linkages are
      phosphorothioate linkages

<400> SEQUENCE: 25
tcgacgtacg tacgtacggg                                                   20

<210> SEQ ID NO 26
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (8)..(11)
<223> OTHER INFORMATION: wherein all the internucleotide linkages are
      phosphorothioate linkages
<220> FEATURE:
<221> NAME/KEY: misc_feature
<222> LOCATION: (16)..(19)
<223> OTHER INFORMATION: wherein all the internucleotide linkages are
      phosphorothioate linkages
<220> FEATURE:
<221> NAME/KEY: misc_feature
<222> LOCATION: (22)..(24)
<223> OTHER INFORMATION: wherein all the internucleotide linkages are
      phosphorothioate linkages

<400> SEQUENCE: 26
tcgacgtttt gacgttttga cggg                                         24

<210> SEQ ID NO 27
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(19)
<223> OTHER INFORMATION: wherein all the internucleotide linkages are
      phosphorothioate linkages with Sp Chirality
<220> FEATURE:
<221> NAME/KEY: misc_feature
<222> LOCATION: (22)..(24)
<223> OTHER INFORMATION: wherein all the internucleotide linkages are
      phosphorothioate linkages with Sp Chirality

<400> SEQUENCE: 27
tcgacgtttt gacgttttga cggg                                         24

<210> SEQ ID NO 28
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Rp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Rp Chirality
<220> FEATURE:
<221> NAME/KEY: misc_feature
<222> LOCATION: (16)..(19)
<223> OTHER INFORMATION: wherein all the internucleotide linkages are
      phosphorothioate linkages with Rp Chirality
<220> FEATURE:
<221> NAME/KEY: misc_feature
<222> LOCATION: (22)..(24)
<223> OTHER INFORMATION: wherein all the internucleotide linkages are
      phosphorothioate linkages with Rp Chirality

<400> SEQUENCE: 28
tcgacgtttt gacgttttga cggg                                         24

<210> SEQ ID NO 29
<211> LENGTH: 25
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages

```
<220> FEATURE:
<221> NAME/KEY: misc_feature
<222> LOCATION: (8)..(11)
<223> OTHER INFORMATION: wherein all the internucleotide linkages are
      phosphorothioate linkages
<220> FEATURE:
<221> NAME/KEY: misc_feature
<222> LOCATION: (16)..(19)
<223> OTHER INFORMATION: wherein all the internucleotide linkages are
      phosphorothioate linkages
<220> FEATURE:
<221> NAME/KEY: misc_feature
<222> LOCATION: (23)..(25)
<223> OTHER INFORMATION: wherein all the internucleotide linkages are
      phosphorothioate linkages

<400> SEQUENCE: 29
tcgacgtttt gacgttttga cgggg                                              25

<210> SEQ ID NO 30
<211> LENGTH: 25
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (8)..(11)
<223> OTHER INFORMATION: wherein all the internucleotide linkages are
      phosphorothioate linkages
<220> FEATURE:
<221> NAME/KEY: misc_feature
<222> LOCATION: (16)..(19)
<223> OTHER INFORMATION: wherein all the internucleotide linkages are
      phosphorothioate linkages
<220> FEATURE:
<221> NAME/KEY: misc_feature
<222> LOCATION: (23)..(25)
<223> OTHER INFORMATION: wherein all the internucleotide linkages are
      phosphorothioate linkages

<400> SEQUENCE: 30
tcgacgtttt gacgttttga cgtgg                                              25

<210> SEQ ID NO 31
<211> LENGTH: 26
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (8)..(11)
<223> OTHER INFORMATION: wherein all the internucleotide linkages are
      phosphorothioate linkages
<220> FEATURE:
<221> NAME/KEY: misc_feature
<222> LOCATION: (16)..(19)
<223> OTHER INFORMATION: wherein all the internucleotide linkages are
      phosphorothioate linkages
<220> FEATURE:
<221> NAME/KEY: misc_feature
<222> LOCATION: (24)..(26)
<223> OTHER INFORMATION: wherein all the internucleotide linkages are
      phosphorothioate linkages
```

<400> SEQUENCE: 31
tcgacgtttt gacgttttga cgtggg          26

<210> SEQ ID NO 32
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (8)..(11)
<223> OTHER INFORMATION: wherein all the internucleotide linkages are
      phosphorothioate linkages
<220> FEATURE:
<221> NAME/KEY: misc_feature
<222> LOCATION: (16)..(24)
<223> OTHER INFORMATION: wherein all the internucleotide linkages are
      phosphorothioate linkages

<400> SEQUENCE: 32
tcgacgtttt gacgttttga cggg          24

<210> SEQ ID NO 33
<211> LENGTH: 27
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (8)..(11)
<223> OTHER INFORMATION: wherein all the internucleotide linkages are
      phosphorothioate linkages
<220> FEATURE:
<221> NAME/KEY: misc_feature
<222> LOCATION: (16)..(19)
<223> OTHER INFORMATION: wherein all the internucleotide linkages are
      phosphorothioate linkages
<220> FEATURE:
<221> NAME/KEY: misc_feature
<222> LOCATION: (23)..(27)
<223> OTHER INFORMATION: wherein all the internucleotide linkages are
      phosphorothioate linkages

<400> SEQUENCE: 33
tcgacgtttt gacgttttga cggggg          27

<210> SEQ ID NO 34
<211> LENGTH: 27
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)

<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(19)
<223> OTHER INFORMATION: wherein all the internucleotide linkages are
      phosphorothioate linkages with Sp Chirality
<220> FEATURE:
<221> NAME/KEY: misc_feature
<222> LOCATION: (23)..(27)
<223> OTHER INFORMATION: wherein all the internucleotide linkages are
      phosphorothioate linkages with Sp Chirality

<400> SEQUENCE: 34
tcgacgtttt gacgttttga cggggggg                                              27

<210> SEQ ID NO 35
<211> LENGTH: 27
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Rp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Rp Chirality
<220> FEATURE:
<221> NAME/KEY: misc_feature
<222> LOCATION: (16)..(19)
<223> OTHER INFORMATION: wherein all the internucleotide linkages are
      phosphorothioate linkages with Rp Chirality
<220> FEATURE:
<221> NAME/KEY: misc_feature
<222> LOCATION: (23)..(27)
<223> OTHER INFORMATION: wherein all the internucleotide linkages are
      phosphorothioate linkages with Rp Chirality

<400> SEQUENCE: 35
tcgacgtttt gacgttttga cggggggg                                              27

<210> SEQ ID NO 36
<211> LENGTH: 26
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (8)..(11)
<223> OTHER INFORMATION: wherein all the internucleotide linkages are
      phosphorothioate linkages
<220> FEATURE:
<221> NAME/KEY: misc_feature
<222> LOCATION: (16)..(19)
<223> OTHER INFORMATION: wherein all the internucleotide linkages are
      phosphorothioate linkages
<220> FEATURE:
<221> NAME/KEY: misc_feature
<222> LOCATION: (22)..(26)
<223> OTHER INFORMATION: wherein all the internucleotide linkages are
      phosphorothioate linkages

<400> SEQUENCE: 36
tcgacgtttt gacgttttga cggggg          26

<210> SEQ ID NO 37
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (7)..(9)
<223> OTHER INFORMATION: wherein all the internucleotide linkages are
      phosphorothioate linkages
<220> FEATURE:
<221> NAME/KEY: misc_feature
<222> LOCATION: (13)..(15)
<223> OTHER INFORMATION: wherein all the internucleotide linkages are
      phosphorothioate linkages
<220> FEATURE:
<221> NAME/KEY: misc_feature
<222> LOCATION: (20)..(22)
<223> OTHER INFORMATION: wherein all the internucleotide linkages are
      phosphorothioate linkages

<400> SEQUENCE: 37
tcgacgttga cgttgacgtg gg          22

<210> SEQ ID NO 38
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(6)
<223> OTHER INFORMATION: wherein all the internucleotide linkages are
      phosphorothioate linkages
<220> FEATURE:
<221> NAME/KEY: misc_feature
<222> LOCATION: (11)..(20)
<223> OTHER INFORMATION: wherein all the internucleotide linkages are
      phosphorothioate linkages

<400> SEQUENCE: 38
ggtgcatcga tgcagggggg          20

<210> SEQ ID NO 39
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (8)..(11)
<223> OTHER INFORMATION: wherein all the internucleotide linkages are
      phosphorothioate linkages
<220> FEATURE:
<221> NAME/KEY: misc_feature
<222> LOCATION: (16)..(19)
<223> OTHER INFORMATION: wherein all the internucleotide linkages are
      phosphorothioate linkages

```
<400> SEQUENCE: 39
tcatcgattt atcgatttat cggg                                           24

<210> SEQ ID NO 40
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(6)
<223> OTHER INFORMATION: wherein all the internucleotide linkages are
      phosphorothioate linkages
<220> FEATURE:
<221> NAME/KEY: misc_feature
<222> LOCATION: (11)..(20)
<223> OTHER INFORMATION: wherein all the internucleotide linkages are
      phosphorothioate linkages

<400> SEQUENCE: 40
ggtgcgacga tgcagggggg                                                20

<210> SEQ ID NO 41
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(5)
<223> OTHER INFORMATION: wherein all the internucleotide linkages are
      phosphorothioate linkages
<220> FEATURE:
<221> NAME/KEY: misc_feature
<222> LOCATION: (17)..(20)
<223> OTHER INFORMATION: wherein all the internucleotide linkages are
      phosphorothioate linkages

<400> SEQUENCE: 41
gggggacgat cgtcgggggg                                                20

<210> SEQ ID NO 42
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (15)..(20)
<223> OTHER INFORMATION: wherein all the internucleotide linkages are
      phosphorothioate linkages

<400> SEQUENCE: 42
gggacgatat cgtcgggggg                                                20

<210> SEQ ID NO 43
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
```

```
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (15)..(20)
<223> OTHER INFORMATION: wherein all the internucleotide linkages are
      phosphorothioate linkages

<400> SEQUENCE: 43
gggacgacgt cgtcggggg                                                    20

<210> SEQ ID NO 44
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (15)..(20)
<223> OTHER INFORMATION: wherein all the internucleotide linkages are
      phosphorothioate linkages with Sp Chirality

<400> SEQUENCE: 44
gggacgacgt cgtcggggg                                                    20

<210> SEQ ID NO 45
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Rp Chirality
<220> FEATURE:
<221> NAME/KEY: misc_feature
<222> LOCATION: (15)..(20)
<223> OTHER INFORMATION: wherein all the internucleotide linkages are
      phosphorothioate linkages with Rp Chirality

<400> SEQUENCE: 45
gggacgacgt cgtcggggg                                                    20

<210> SEQ ID NO 46
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (15)..(20)
<223> OTHER INFORMATION: wherein all the internucleotide linkages are
      phosphorothioate linkages

<400> SEQUENCE: 46
gggggacgat cgtcggggg                                                    20
```

<210> SEQ ID NO 47
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (13)..(20)
<223> OTHER INFORMATION: wherein all the internucleotide linkages are
      phosphorothioate linkages

<400> SEQUENCE: 47
gggacgcgcg tcgggggggg                                                   20

<210> SEQ ID NO 48
<211> LENGTH: 14
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(5)
<223> OTHER INFORMATION: wherein all the internucleotide linkages are
      phosphorothioate linkages
<220> FEATURE:
<221> NAME/KEY: misc_feature
<222> LOCATION: (11)..(14)
<223> OTHER INFORMATION: wherein all the internucleotide linkages are
      phosphorothioate linkages

<400> SEQUENCE: 48
ggggtcgttc gggg                                                         14

<210> SEQ ID NO 49
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(24)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(24)
<223> OTHER INFORMATION: wherein all the internucleotide linkages are
      phosphorothioate linkages with Sp Chirality

<400> SEQUENCE: 49
tcatcgattt atcgatttaa cggg                                              24

<210> SEQ ID NO 50
<211> LENGTH: 24

```
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(24)
<223> OTHER INFORMATION: wherein all the internucleotide linkages are
      phosphorothioate linkages with Sp Chirality

<400> SEQUENCE: 50
tcgacgtttt gacgttttga cggg                                           24

<210> SEQ ID NO 51
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (18)..(24)
<223> OTHER INFORMATION: wherein all the internucleotide linkages are
      phosphorothioate linkages with Sp Chirality

<400> SEQUENCE: 51
tcgacgtttt gacgttttga cggg                                           24

<210> SEQ ID NO 52
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (7)..(9)
<223> OTHER INFORMATION: wherein all the internucleotide linkages are
      phosphorothioate linkages with Sp Chirality
<220> FEATURE:
<221> NAME/KEY: misc_feature
<222> LOCATION: (13)..(15)
<223> OTHER INFORMATION: wherein all the internucleotide linkages are
      phosphorothioate linkages with Sp Chirality
<220> FEATURE:
<221> NAME/KEY: misc_feature
<222> LOCATION: (19)..(20)
<223> OTHER INFORMATION: wherein all the internucleotide linkages are
      phosphorothioate linkages with Sp Chirality

<400> SEQUENCE: 52
tcgacgttga cgttgacggg                                                20

<210> SEQ ID NO 53
<211> LENGTH: 20
<212> TYPE: DNA
<213> ORGANISM: Artificial Sequence
<220> FEATURE:
```

```
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (7)..(9)
<223> OTHER INFORMATION: wherein all the internucleotide linkages are
      phosphorothioate linkages with Sp Chirality
<220> FEATURE:
<221> NAME/KEY: misc_feature
<222> LOCATION: (13)..(15)
<223> OTHER INFORMATION: wherein all the internucleotide linkages are
      phosphorothioate linkages with Sp Chirality
<220> FEATURE:
<221> NAME/KEY: misc_feature
<222> LOCATION: (18)..(20)
<223> OTHER INFORMATION: wherein all the internucleotide linkages are
      phosphorothioate linkages with Sp Chirality

<400> SEQUENCE: 53
tcgacgttga cgttgacggg                                               20

<210> SEQ ID NO 54
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (7)..(9)
<223> OTHER INFORMATION: wherein all the internucleotide linkages are
      phosphorothioate linkages with Sp Chirality
<220> FEATURE:
<221> NAME/KEY: misc_feature
<222> LOCATION: (13)..(15)
<223> OTHER INFORMATION: wherein all the internucleotide linkages are
      phosphorothioate linkages with Sp Chirality
<220> FEATURE:
<221> NAME/KEY: misc_feature
<222> LOCATION: (19)..(21)
<223> OTHER INFORMATION: wherein all the internucleotide linkages are
      phosphorothioate linkages with Sp Chirality

<400> SEQUENCE: 54
tcgacgttga cgttgacggg g                                             21

<210> SEQ ID NO 55
<211> LENGTH: 19
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (7)..(9)
<223> OTHER INFORMATION: wherein all the internucleotide linkages are
      phosphorothioate linkages with Sp Chirality
<220> FEATURE:
<221> NAME/KEY: misc_feature
<222> LOCATION: (13)..(15)
<223> OTHER INFORMATION: wherein all the internucleotide linkages are
```

-continued

```
    phosphorothioate linkages with Sp Chirality
<220> FEATURE:
<221> NAME/KEY: misc_feature
<222> LOCATION: (18)..(19)
<223> OTHER INFORMATION: wherein all the internucleotide linkages are
      phosphorothioate linkages with Sp Chirality

<400> SEQUENCE: 55
tcgacgttga cgttgactg                                                    19

<210> SEQ ID NO 56
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (7)..(9)
<223> OTHER INFORMATION: wherein all the internucleotide linkages are
      phosphorothioate linkages with Sp Chirality
<220> FEATURE:
<221> NAME/KEY: misc_feature
<222> LOCATION: (13)..(20)
<223> OTHER INFORMATION: wherein all the internucleotide linkages are
      phosphorothioate linkages with Sp Chirality

<400> SEQUENCE: 56
tcgacgttga cgttgacggg                                                   20

<210> SEQ ID NO 57
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (13)..(20)
<223> OTHER INFORMATION: wherein all the internucleotide linkages are
      phosphorothioate linkages with Sp Chirality

<400> SEQUENCE: 57
tcgacgttga cgttgacggg                                                   20

<210> SEQ ID NO 58
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (13)..(20)
<223> OTHER INFORMATION: wherein all the internucleotide linkages are
      phosphorothioate linkages with Sp Chirality

<400> SEQUENCE: 58
```
tcatcgatat cgatgacggg                                               20

<210> SEQ ID NO 59
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (7)..(9)
<223> OTHER INFORMATION: wherein all the internucleotide linkages are
      phosphorothioate linkages with Sp Chirality
<220> FEATURE:
<221> NAME/KEY: misc_feature
<222> LOCATION: (13)..(15)
<223> OTHER INFORMATION: wherein all the internucleotide linkages are
      phosphorothioate linkages with Sp Chirality
<220> FEATURE:
<221> NAME/KEY: misc_feature
<222> LOCATION: (18)..(21)
<223> OTHER INFORMATION: wherein all the internucleotide linkages are
      phosphorothioate linkages with Sp Chirality

<400> SEQUENCE: 59
tcgacgttga cgttgacggg g                                             21

<210> SEQ ID NO 60
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(23)
<223> OTHER INFORMATION: wherein all the internucleotide linkages are
      phosphorothioate linkages with Sp Chirality

<400> SEQUENCE: 60
tcgacgtttt gacgttttgg ggg                                           23

<210> SEQ ID NO 61
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality

```
<220> FEATURE:
<221> NAME/KEY: misc_feature
<222> LOCATION: (16)..(24)
<223> OTHER INFORMATION: wherein all the internucleotide linkages are
      phosphorothioate linkages with Sp Chirality

<400> SEQUENCE: 61
tcgacgtttt gacgttttga gggg                                              24

<210> SEQ ID NO 62
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(24)
<223> OTHER INFORMATION: wherein all the internucleotide linkages are
      phosphorothioate linkages with Sp Chirality

<400> SEQUENCE: 62
tcgacgtttt gacgttttgt gggg                                              24

<210> SEQ ID NO 63
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(4)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(10)
<223> OTHER INFORMATION: wherein all the internucleotide linkages are
      phosphorothioate linkages with Sp Chirality
<220> FEATURE:
<221> NAME/KEY: misc_feature
<222> LOCATION: (14)..(20)
<223> OTHER INFORMATION: wherein all the internucleotide linkages are
      phosphorothioate linkages with Sp Chirality

<400> SEQUENCE: 63
tcgacgttga cgttgacggg                                                   20

<210> SEQ ID NO 64
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
```

```
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(19)
<223> OTHER INFORMATION: wherein all the internucleotide linkages are
      phosphorothioate linkages with Sp Chirality
<220> FEATURE:
<221> NAME/KEY: misc_feature
<222> LOCATION: (22)..(24)
<223> OTHER INFORMATION: wherein all the internucleotide linkages are
      phosphorothioate linkages with Sp Chirality

<400> SEQUENCE: 64
ccgacgtttt gacgttttga cggg                                           24

<210> SEQ ID NO 65
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(19)
<223> OTHER INFORMATION: wherein all the internucleotide linkages are
      phosphorothioate linkages with Sp Chirality
<220> FEATURE:
<221> NAME/KEY: misc_feature
<222> LOCATION: (22)..(24)
<223> OTHER INFORMATION: wherein all the internucleotide linkages are
      phosphorothioate linkages with Sp Chirality

<400> SEQUENCE: 65
tcgacgttta gacgtttaga cggg                                           24

<210> SEQ ID NO 66
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(19)
<223> OTHER INFORMATION: wherein all the internucleotide linkages are
      phosphorothioate linkages with Sp Chirality
<220> FEATURE:
<221> NAME/KEY: misc_feature
<222> LOCATION: (22)..(24)
<223> OTHER INFORMATION: wherein all the internucleotide linkages are
      phosphorothioate linkages with Sp Chirality

<400> SEQUENCE: 66
```

```
tcgacgtttt gacgttttga cgaa                                          24
```

<210> SEQ ID NO 67
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(19)
<223> OTHER INFORMATION: wherein all the internucleotide linkages are
      phosphorothioate linkages with Sp Chirality
<220> FEATURE:
<221> NAME/KEY: misc_feature
<222> LOCATION: (22)..(24)
<223> OTHER INFORMATION: wherein all the internucleotide linkages are
      phosphorothioate linkages with Sp Chirality

<400> SEQUENCE: 67

```
tcgacgtttt gacgttttga cgtt                                          24
```

<210> SEQ ID NO 68
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(19)
<223> OTHER INFORMATION: wherein all the internucleotide linkages are
      phosphorothioate linkages with Sp Chirality
<220> FEATURE:
<221> NAME/KEY: misc_feature
<222> LOCATION: (22)..(24)
<223> OTHER INFORMATION: wherein all the internucleotide linkages are
      phosphorothioate linkages with Sp Chirality

<400> SEQUENCE: 68

```
tcaacgtttt aacgttttga cggg                                          24
```

<210> SEQ ID NO 69
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:

```
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(19)
<223> OTHER INFORMATION: wherein all the internucleotide linkages are
      phosphorothioate linkages with Sp Chirality

<400> SEQUENCE: 69
tcgacgtttt gacgttttgg g                                              21

<210> SEQ ID NO 70
<211> LENGTH: 26
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(19)
<223> OTHER INFORMATION: wherein all the internucleotide linkages are
      phosphorothioate linkages with Sp Chirality

<400> SEQUENCE: 70
tcgacgtttt gacgttttga cgttgg                                         26

<210> SEQ ID NO 71
<211> LENGTH: 17
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(9)
<223> OTHER INFORMATION: wherein all the internucleotide linkages are
      phosphorothioate linkages with Sp Chirality
<220> FEATURE:
<221> NAME/KEY: misc_feature
<222> LOCATION: (14)..(17)
<223> OTHER INFORMATION: wherein all the internucleotide linkages are
      phosphorothioate linkages with Sp Chirality

<400> SEQUENCE: 71
tcgacgttga cgttggg                                                   17

<210> SEQ ID NO 72
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
```

```
     phosphorothioate linkages with Sp Chirality
<220> FEATURE:
<221> NAME/KEY: misc_feature
<222> LOCATION: (8)..(12)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(20)
<223> OTHER INFORMATION: wherein all the internucleotide linkages are
      phosphorothioate linkages with Sp Chirality
<220> FEATURE:
<221> NAME/KEY: misc_feature
<222> LOCATION: (22)..(24)
<223> OTHER INFORMATION: wherein all the internucleotide linkages are
      phosphorothioate linkages with Sp Chirality

<400> SEQUENCE: 72
tcgacgtttt gacgttttga cggg                                                24

<210> SEQ ID NO 73
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(5)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(12)
<223> OTHER INFORMATION: wherein all the internucleotide linkages are
      phosphorothioate linkages with Sp Chirality

<400> SEQUENCE: 73
tcgacgtttt gacgttttga cggg                                                24

<210> SEQ ID NO 74
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(4)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(12)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(20)
<223> OTHER INFORMATION: wherein all the internucleotide linkages are
      phosphorothioate linkages with Sp Chirality
<220> FEATURE:
<221> NAME/KEY: misc_feature
<222> LOCATION: (22)..(24)
<223> OTHER INFORMATION: wherein all the internucleotide linkages are
      phosphorothioate linkages with Sp Chirality

<400> SEQUENCE: 74
tcgacgtttt gacgttttga cggg                                                24

<210> SEQ ID NO 75
<211> LENGTH: 20
<212> TYPE: DNA
```

```
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(9)
<223> OTHER INFORMATION: wherein all the internucleotide linkages are
      phosphorothioate linkages with Sp Chirality
<220> FEATURE:
<221> NAME/KEY: misc_feature
<222> LOCATION: (14)..(15)
<223> OTHER INFORMATION: wherein all the internucleotide linkages are
      phosphorothioate linkages with Sp Chirality
<220> FEATURE:
<221> NAME/KEY: misc_feature
<222> LOCATION: (18)..(20)
<223> OTHER INFORMATION: wherein all the internucleotide linkages are
      phosphorothioate linkages with Sp Chirality

<400> SEQUENCE: 75
tcgacgtaga cgtagacggg                                                20

<210> SEQ ID NO 76
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(19)
<223> OTHER INFORMATION: wherein all the internucleotide linkages are
      phosphorothioate linkages with Sp Chirality
<220> FEATURE:
<221> NAME/KEY: misc_feature
<222> LOCATION: (22)..(24)
<223> OTHER INFORMATION: wherein all the internucleotide linkages are
      phosphorothioate linkages with Sp Chirality

<400> SEQUENCE: 76
tagacgattc gtcgtctaga cggg                                           24

<210> SEQ ID NO 77
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (7)..(9)
<223> OTHER INFORMATION: wherein all the internucleotide linkages are
      phosphorothioate linkages with Sp Chirality
<220> FEATURE:
<221> NAME/KEY: misc_feature
```

<222> LOCATION: (13)..(15)
<223> OTHER INFORMATION: wherein all the internucleotide linkages are
      phosphorothioate linkages with Sp Chirality
<220> FEATURE:
<221> NAME/KEY: misc_feature
<222> LOCATION: (18)..(20)
<223> OTHER INFORMATION: wherein all the internucleotide linkages are
      phosphorothioate linkages with Sp Chirality

<400> SEQUENCE: 77
tagacgacgt cgtagacggg                                                    20

<210> SEQ ID NO 78
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(4)
<223> OTHER INFORMATION: wherein all the internucleotide linkages are
      phosphorothioate linkages with Sp Chirality
<220> FEATURE:
<221> NAME/KEY: misc_feature
<222> LOCATION: (9)..(12)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(24)
<223> OTHER INFORMATION: wherein all the internucleotide linkages are
      phosphorothioate linkages with Sp Chirality

<400> SEQUENCE: 78
tcgacgtttt gacgttttga cggg                                               24

<210> SEQ ID NO 79
<211> LENGTH: 25
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(4)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(13)
<223> OTHER INFORMATION: wherein all the internucleotide linkages are
      phosphorothioate linkages with Sp Chirality
<220> FEATURE:
<221> NAME/KEY: misc_feature
<222> LOCATION: (17)..(25)
<223> OTHER INFORMATION: wherein all the internucleotide linkages are
      phosphorothioate linkages with Sp Chirality

<400> SEQUENCE: 79
tcgacgtttt taacgacttg acggg                                              25

<210> SEQ ID NO 80
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(4)
<223> OTHER INFORMATION: wherein all the internucleotide linkages are
      phosphorothioate linkages with Sp Chirality

```
<220> FEATURE:
<221> NAME/KEY: misc_feature
<222> LOCATION: (9)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(24)
<223> OTHER INFORMATION: wherein all the internucleotide linkages are
      phosphorothioate linkages with Sp Chirality

<400> SEQUENCE: 80
tcgacgtttt aacgacttga cggg                                              24

<210> SEQ ID NO 81
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(19)
<223> OTHER INFORMATION: wherein all the internucleotide linkages are
      phosphorothioate linkages with Sp Chirality
<220> FEATURE:
<221> NAME/KEY: misc_feature
<222> LOCATION: (22)..(24)
<223> OTHER INFORMATION: wherein all the internucleotide linkages are
      phosphorothioate linkages with Sp Chirality

<400> SEQUENCE: 81
tcatcgattt atcgatttga cggg                                              24

<210> SEQ ID NO 82
<211> LENGTH: 27
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(19)
<223> OTHER INFORMATION: wherein all the internucleotide linkages are
      phosphorothioate linkages with Sp Chirality
<220> FEATURE:
<221> NAME/KEY: misc_feature
<222> LOCATION: (23)..(27)
<223> OTHER INFORMATION: wherein all the internucleotide linkages are
      phosphorothioate linkages with Sp Chirality

<400> SEQUENCE: 82
tcatcgattt atcgatttat cgatggg                                           27
```

<210> SEQ ID NO 83
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(19)
<223> OTHER INFORMATION: wherein all the internucleotide linkages are
      phosphorothioate linkages with Sp Chirality
<220> FEATURE:
<221> NAME/KEY: misc_feature
<222> LOCATION: (20)..(24)
<223> OTHER INFORMATION: wherein all the internucleotide linkages are
      phosphorothioate linkages with Sp Chirality

<400> SEQUENCE: 83
tcatcgattt atcgatttat cggg                                          24

<210> SEQ ID NO 84
<211> LENGTH: 32
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(19)
<223> OTHER INFORMATION: wherein all the internucleotide linkages are
      phosphorothioate linkages with Sp Chirality
<220> FEATURE:
<221> NAME/KEY: misc_feature
<222> LOCATION: (24)..(27)
<223> OTHER INFORMATION: wherein all the internucleotide linkages are
      phosphorothioate linkages with Sp Chirality
<220> FEATURE:
<221> NAME/KEY: misc_feature
<222> LOCATION: (30)..(32)
<223> OTHER INFORMATION: wherein all the internucleotide linkages are
      phosphorothioate linkages with Sp Chirality

<400> SEQUENCE: 84
tcatcgattt atcgatttat cgatttatcg gg                                 32

<210> SEQ ID NO 85
<211> LENGTH: 32
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)

```
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(19)
<223> OTHER INFORMATION: wherein all the internucleotide linkages are
      phosphorothioate linkages with Sp Chirality
<220> FEATURE:
<221> NAME/KEY: misc_feature
<222> LOCATION: (24)..(32)
<223> OTHER INFORMATION: wherein all the internucleotide linkages are
      phosphorothioate linkages with Sp Chirality

<400> SEQUENCE: 85
tcatcgattt atcgatttat cgatttatcg gg                                     32

<210> SEQ ID NO 86
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(19)
<223> OTHER INFORMATION: wherein all the internucleotide linkages are
      phosphorothioate linkages with Sp Chirality
<220> FEATURE:
<221> NAME/KEY: misc_feature
<222> LOCATION: (24)..(30)
<223> OTHER INFORMATION: wherein all the internucleotide linkages are
      phosphorothioate linkages with Sp Chirality

<400> SEQUENCE: 86
tcatcgattt atcgatttat cgatatcggg                                        30

<210> SEQ ID NO 87
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(24)
<223> OTHER INFORMATION: wherein all the internucleotide linkages are
      phosphorothioate linkages with Sp Chirality

<400> SEQUENCE: 87
```
ttatcgattt atcgatttga cggg          24

<210> SEQ ID NO 88
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (14)..(22)
<223> OTHER INFORMATION: wherein all the internucleotide linkages are
      phosphorothioate linkages with Sp Chirality

<400> SEQUENCE: 88
tcatcgatat cgatttgacg gg          22

<210> SEQ ID NO 89
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(24)
<223> OTHER INFORMATION: wherein all the internucleotide linkages are
      phosphorothioate linkages with Sp Chirality

<400> SEQUENCE: 89
tcatcgattt atcgatttat cggg          24

<210> SEQ ID NO 90
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(24)
<223> OTHER INFORMATION: wherein all the internucleotide linkages are
      phosphorothioate linkages with Sp Chirality

<400> SEQUENCE: 90
tcatcgattt atcgatttga cgat          24

<210> SEQ ID NO 91
<211> LENGTH: 23
<212> TYPE: DNA
<213> ORGANISM: Artificial Sequence
<220> FEATURE:

```
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (7)..(9)
<223> OTHER INFORMATION: wherein all the internucleotide linkages are
      phosphorothioate linkages with Sp Chirality
<220> FEATURE:
<221> NAME/KEY: misc_feature
<222> LOCATION: (13)..(15)
<223> OTHER INFORMATION: wherein all the internucleotide linkages are
      phosphorothioate linkages with Sp Chirality
<220> FEATURE:
<221> NAME/KEY: misc_feature
<222> LOCATION: (19)..(23)
<223> OTHER INFORMATION: wherein all the internucleotide linkages are
      phosphorothioate linkages with Sp Chirality

<400> SEQUENCE: 91
tcgacgttga cgttgacgtt ggg                                         23

<210> SEQ ID NO 92
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(4)
<223> OTHER INFORMATION: wherein all the internucleotide linkages are
      phosphorothioate linkages with Sp Chirality
<220> FEATURE:
<221> NAME/KEY: misc_feature
<222> LOCATION: (7)..(10)
<223> OTHER INFORMATION: wherein all the internucleotide linkages are
      phosphorothioate linkages with Sp Chirality
<220> FEATURE:
<221> NAME/KEY: misc_feature
<222> LOCATION: (13)..(20)
<223> OTHER INFORMATION: wherein all the internucleotide linkages are
      phosphorothioate linkages with Sp Chirality

<400> SEQUENCE: 92
tcgacgttga cgttgacggg                                             20

<210> SEQ ID NO 93
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(4)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(12)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(24)
<223> OTHER INFORMATION: wherein all the internucleotide linkages are
      phosphorothioate linkages with Sp Chirality

<400> SEQUENCE: 93
tcatcgattt atcgatttga cggg                                        24
```

```
<210> SEQ ID NO 94
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(4)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(10)
<223> OTHER INFORMATION: wherein all the internucleotide linkages are
      phosphorothioate linkages with Sp Chirality
<220> FEATURE:
<221> NAME/KEY: misc_feature
<222> LOCATION: (14)..(16)
<223> OTHER INFORMATION: wherein all the internucleotide linkages are
      phosphorothioate linkages with Sp Chirality
<220> FEATURE:
<221> NAME/KEY: misc_feature
<222> LOCATION: (19)..(24)
<223> OTHER INFORMATION: wherein all the internucleotide linkages are
      phosphorothioate linkages with Sp Chirality

<400> SEQUENCE: 94
tcatcgatat cgatgacgtt tggg                                          24

<210> SEQ ID NO 95
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(22)
<223> OTHER INFORMATION: wherein all the internucleotide linkages are
      phosphorothioate linkages with Sp Chirality

<400> SEQUENCE: 95
tcgacgtttg acgtttgacg gg                                            22

<210> SEQ ID NO 96
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(24)
<223> OTHER INFORMATION: wherein all the internucleotide linkages are
      phosphorothioate linkages with Sp Chirality

<400> SEQUENCE: 96
```
tcatcgattt atcgatttat cggg                                              24

<210> SEQ ID NO 97
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (15)..(20)
<223> OTHER INFORMATION: wherein all the internucleotide linkages are
      phosphorothioate linkages with Sp Chirality

<400> SEQUENCE: 97
gggacgatat cgtcgggggg                                                   20

<210> SEQ ID NO 98
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(10)
<223> OTHER INFORMATION: wherein all the internucleotide linkages are
      phosphorothioate linkages with Sp Chirality
<220> FEATURE:
<221> NAME/KEY: misc_feature
<222> LOCATION: (15)..(20)
<223> OTHER INFORMATION: wherein all the internucleotide linkages are
      phosphorothioate linkages with Sp Chirality

<400> SEQUENCE: 98
gggacgacgt cgtcggggggg                                                  20

<210> SEQ ID NO 99
<211> LENGTH: 19
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (15)..(19)
<223> OTHER INFORMATION: wherein all the internucleotide linkages are
      phosphorothioate linkages with Sp Chirality

<400> SEQUENCE: 99
gggacgacgt cgtcggggg                                                    19

<210> SEQ ID NO 100
<211> LENGTH: 20
<212> TYPE: DNA
<213> ORGANISM: Artificial Sequence

```
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (15)..(20)
<223> OTHER INFORMATION: wherein all the internucleotide linkages are
      phosphorothioate linkages with Sp Chirality

<400> SEQUENCE: 100
tcgacgacgt cgtcggggggg                                               20

<210> SEQ ID NO 101
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (15)..(20)
<223> OTHER INFORMATION: wherein all the internucleotide linkages are
      phosphorothioate linkages with Sp Chirality

<400> SEQUENCE: 101
tcgacgacgt cgtctttggg                                                20

<210> SEQ ID NO 102
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (15)..(20)
<223> OTHER INFORMATION: wherein all the internucleotide linkages are
      phosphorothioate linkages with Sp Chirality

<400> SEQUENCE: 102
tagacgacgt cgtctttggg                                                20

<210> SEQ ID NO 103
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (15)..(20)
<223> OTHER INFORMATION: wherein all the internucleotide linkages are
      phosphorothioate linkages with Sp Chirality
```

<400> SEQUENCE: 103
ttgacgacgt cgtcaaaggg                                              20

<210> SEQ ID NO 104
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (15)..(20)
<223> OTHER INFORMATION: wherein all the internucleotide linkages are
      phosphorothioate linkages with Sp Chirality

<400> SEQUENCE: 104
tcgacgtaga cgtctttggg                                              20

<210> SEQ ID NO 105
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (15)..(20)
<223> OTHER INFORMATION: wherein all the internucleotide linkages are
      phosphorothioate linkages with Sp Chirality

<400> SEQUENCE: 105
tcgacgtaga cgtttagggg                                              20

<210> SEQ ID NO 106
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (15)..(20)
<223> OTHER INFORMATION: wherein all the internucleotide linkages are
      phosphorothioate linkages with Sp Chirality

<400> SEQUENCE: 106
tcatcgatat cgattttggg                                              20

<210> SEQ ID NO 107
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature

```
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (15)..(20)
<223> OTHER INFORMATION: wherein all the internucleotide linkages are
      phosphorothioate linkages with Sp Chirality

<400> SEQUENCE: 107
ttatcgatat cgataaaggg                                              20

<210> SEQ ID NO 108
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (17)..(21)
<223> OTHER INFORMATION: wherein all the internucleotide linkages are
      phosphorothioate linkages with Sp Chirality

<400> SEQUENCE: 108
tcgacgtaga cgatcgatgg g                                            21

<210> SEQ ID NO 109
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(24)
<223> OTHER INFORMATION: wherein all the internucleotide linkages are
      phosphorothioate linkages with Sp Chirality

<400> SEQUENCE: 109
tcgacgactt gacgacttga cggg                                         24

<210> SEQ ID NO 110
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
```

```
<220> FEATURE:
<221> NAME/KEY: misc_feature
<222> LOCATION: (16)..(24)
<223> OTHER INFORMATION: wherein all the internucleotide linkages are
      phosphorothioate linkages with Sp Chirality

<400> SEQUENCE: 110
tcgacgactt gtcgtcttga cggg                                              24

<210> SEQ ID NO 111
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (15)..(23)
<223> OTHER INFORMATION: wherein all the internucleotide linkages are
      phosphorothioate linkages with Sp Chirality

<400> SEQUENCE: 111
ttatcgatat cgatatcgat ggg                                               23

<210> SEQ ID NO 112
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (15)..(22)
<223> OTHER INFORMATION: wherein all the internucleotide linkages are
      phosphorothioate linkages with Sp Chirality

<400> SEQUENCE: 112
ttatcgatat cgatttaaag gg                                                22

<210> SEQ ID NO 113
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(24)
<223> OTHER INFORMATION: wherein all the internucleotide linkages are
      phosphorothioate linkages with Sp Chirality

<400> SEQUENCE: 113
```

```
tcatcgattt atcgatttga cgtt                                              24
```

<210> SEQ ID NO 114
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (7)..(9)
<223> OTHER INFORMATION: wherein all the internucleotide linkages are
      phosphorothioate linkages with Sp Chirality
<220> FEATURE:
<221> NAME/KEY: misc_feature
<222> LOCATION: (13)..(21)
<223> OTHER INFORMATION: wherein all the internucleotide linkages are
      phosphorothioate linkages with Sp Chirality

<400> SEQUENCE: 114

```
tcatcgatat cgatgacggg g                                                 21
```

<210> SEQ ID NO 115
<211> LENGTH: 17
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(9)
<223> OTHER INFORMATION: wherein all the internucleotide linkages are
      phosphorothioate linkages with Sp Chirality
<220> FEATURE:
<221> NAME/KEY: misc_feature
<222> LOCATION: (13)..(17)
<223> OTHER INFORMATION: wherein all the internucleotide linkages are
      phosphorothioate linkages with Sp Chirality

<400> SEQUENCE: 115

```
tcatcgatat cgatggg                                                      17
```

<210> SEQ ID NO 116
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (13)..(20)
<223> OTHER INFORMATION: wherein all the internucleotide linkages are
      phosphorothioate linkages with Sp Chirality

<400> SEQUENCE: 116

```
tcgtcgttgt cgttgacggg                                                   20
```

```
<210> SEQ ID NO 117
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(4)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(12)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(24)
<223> OTHER INFORMATION: wherein all the internucleotide linkages are
      phosphorothioate linkages with Sp Chirality

<400> SEQUENCE: 117
tcgtcgtttt gtcgttttga cggg                                          24

<210> SEQ ID NO 118
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (15)..(23)
<223> OTHER INFORMATION: wherein all the internucleotide linkages are
      phosphorothioate linkages with Sp Chirality

<400> SEQUENCE: 118
tcgtcgttgt cgttgacgac ggg                                           23

<210> SEQ ID NO 119
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(24)
<223> OTHER INFORMATION: wherein all the internucleotide linkages are
      phosphorothioate linkages with Sp Chirality

<400> SEQUENCE: 119
tcgtcgtttt gtcgttttgt cgtt                                          24
```